United States Patent
Sand et al.

(10) Patent No.: US 11,877,756 B2
(45) Date of Patent: Jan. 23, 2024

(54) SYSTEMS AND METHODS FOR DECORTICATING THE SACROILIAC JOINT

(71) Applicant: SI-Bone Inc., Santa Clara, CA (US)

(72) Inventors: Paul Sand, Redwood City, CA (US);
Bret Schneider, San Jose, CA (US);
Patrick Kahn, Livermore, CA (US);
Scott A. Yerby, Montara, CA (US);
Gerard Librodo, El Dorado, KS (US);
Khalid Sethi, Binghamton, NY (US);
Craig Meyer, Columbia, MO (US);
Michael Didinsky, Kenosha, WI (US);
Thomas A. McNally, Chicago, IL (US);
Robert McLain, Pepper Pike, OH (US); Nikolas Kerr, Milpitas, CA (US);
Eric Swick, Oconomowoc, WI (US);
Yale Van Dyne, Overland Park, KS (US); Jen Kasler, Chicago, IL (US)

(73) Assignee: SI-Bone Inc., Santa Clara, CA (US)

( * ) Notice: Subject to any disclaimer, the term of this patent is extended or adjusted under 35 U.S.C. 154(b) by 290 days.

(21) Appl. No.: 17/447,550

(22) Filed: Sep. 13, 2021

(65) Prior Publication Data

US 2022/0096098 A1 Mar. 31, 2022

Related U.S. Application Data

(63) Continuation of application No. 16/143,061, filed on Sep. 26, 2018, now Pat. No. 11,116,519.
(Continued)

(51) Int. Cl.
*A61B 17/16* (2006.01)
*A61B 17/17* (2006.01)
(Continued)

(52) U.S. Cl.
CPC .... *A61B 17/1615* (2013.01); *A61B 17/00234* (2013.01); *A61B 17/1617* (2013.01);
(Continued)

(58) Field of Classification Search
CPC combination set(s) only.
See application file for complete search history.

(56) References Cited

U.S. PATENT DOCUMENTS

| 1,951,278 A | 3/1934 | Ericsson |
| 2,136,471 A | 11/1938 | Schneider |

(Continued)

FOREIGN PATENT DOCUMENTS

| CN | 1128944 A | 8/1996 |
| CN | 1190882 A | 8/1998 |

(Continued)

OTHER PUBLICATIONS

Follini et al.; U.S. Appl. No. 17/777,679 entitled "Rod coupling assemblies for bone stabilization constructs," filed May 18, 2022.
(Continued)

*Primary Examiner* — Sameh R Boles
(74) *Attorney, Agent, or Firm* — Shay Glenn LLP

(57) ABSTRACT

A system for decorticating at least one bone surface includes an elongated soft tissue protector, an elongated drive shaft and a cutter. The elongated soft tissue protector has a bore extending therethrough. The bore has a non-circular lateral cross-section, a maximum lateral extent and a minimum lateral extent. The cutter may be located on or near a distal end of the drive shaft. The cutter has a non-circular lateral cross-section, a maximum lateral extent and a minimum lateral extent. The maximum lateral extent of the cutter is greater than the minimum lateral extent of the bore but is no greater than the maximum lateral extent of the bore. The bore of the soft tissue protector is configured to slidably
(Continued)

receive the cutter therethrough. Other systems and methods for decorticating at least one bone surface are also provided.

13 Claims, 36 Drawing Sheets

Related U.S. Application Data

(60) Provisional application No. 62/563,271, filed on Sep. 26, 2017.

(51) Int. Cl.
  *A61B 90/00* (2016.01)
  *A61B 17/00* (2006.01)
  *A61B 34/20* (2016.01)

(52) U.S. Cl.
  CPC ...... *A61B 17/1622* (2013.01); *A61B 17/1633* (2013.01); *A61B 17/1664* (2013.01); *A61B 17/1671* (2013.01); *A61B 17/1703* (2013.01); *A61B 90/39* (2016.02); *A61B 34/20* (2016.02); *A61B 2090/3937* (2016.02); *A61B 2090/3983* (2016.02)

(56) References Cited

U.S. PATENT DOCUMENTS

| | | |
|---|---|---|
| 2,243,717 A | 5/1941 | Moreira |
| 2,414,882 A | 7/1947 | Longfellow |
| 2,562,419 A | 7/1951 | Ferris |
| 2,675,801 A | 4/1954 | Bambara et al. |
| 2,697,433 A | 12/1954 | Zehnder |
| 3,076,453 A | 2/1963 | Tronzo |
| 3,506,982 A | 4/1970 | Steffee |
| 3,694,821 A | 10/1972 | Moritz |
| 3,709,218 A | 1/1973 | Halloran |
| 3,744,488 A | 7/1973 | Cox |
| 4,059,115 A | 11/1977 | Jumashev et al. |
| 4,156,943 A | 6/1979 | Collier |
| 4,197,645 A | 4/1980 | Scheicher |
| 4,292,964 A | 10/1981 | Ulrich |
| 4,341,206 A | 7/1982 | Perrett et al. |
| 4,344,190 A | 8/1982 | Lee et al. |
| 4,399,813 A | 8/1983 | Barber |
| 4,423,721 A | 1/1984 | Otte et al. |
| 4,475,545 A | 10/1984 | Ender |
| 4,501,269 A | 2/1985 | Bagby |
| 4,569,338 A | 2/1986 | Edwards |
| 4,612,918 A | 9/1986 | Slocum |
| 4,622,959 A | 11/1986 | Marcus |
| 4,630,601 A | 12/1986 | Harder et al. |
| 4,638,799 A | 1/1987 | Moore |
| 4,657,550 A | 4/1987 | Daher |
| 4,743,256 A | 5/1988 | Brantigan |
| 4,773,402 A | 9/1988 | Asher et al. |
| 4,787,378 A | 11/1988 | Sodhi |
| 4,790,303 A | 12/1988 | Steffee |
| 4,834,757 A | 5/1989 | Brantigan |
| 4,846,162 A | 7/1989 | Moehring |
| 4,877,019 A | 10/1989 | Vives |
| 4,878,915 A | 11/1989 | Brantigan |
| 4,898,186 A | 2/1990 | Ikada et al. |
| 4,904,261 A | 2/1990 | Dove et al. |
| 4,950,270 A | 8/1990 | Bowman et al. |
| 4,961,740 A | 10/1990 | Ray et al. |
| 4,969,888 A | 11/1990 | Scholten et al. |
| 4,981,481 A | 1/1991 | Kranz et al. |
| 5,034,011 A | 7/1991 | Howland |
| 5,034,013 A | 7/1991 | Kyle et al. |
| 5,035,697 A | 7/1991 | Frigg |
| 5,041,118 A | 8/1991 | Wasilewski |
| 5,053,035 A | 10/1991 | McLaren |
| 5,059,193 A | 10/1991 | Kuslich |
| 5,066,296 A | 11/1991 | Chapman et al. |
| 5,098,434 A | 3/1992 | Serbousek |
| 5,102,414 A | 4/1992 | Kirsch |
| 5,108,397 A | 4/1992 | White |
| 5,122,141 A | 6/1992 | Simpson et al. |
| 5,139,498 A | 8/1992 | Astudillo Ley |
| 5,139,500 A | 8/1992 | Schwartz |
| 5,147,367 A | 9/1992 | Ellis |
| 5,147,402 A | 9/1992 | Bohler et al. |
| 5,190,551 A | 3/1993 | Chin et al. |
| 5,197,961 A | 3/1993 | Castle |
| 5,242,444 A | 9/1993 | MacMillan |
| 5,298,254 A | 3/1994 | Prewett et al. |
| 5,334,205 A | 8/1994 | Cain |
| 5,380,325 A | 1/1995 | Lahille et al. |
| 5,390,683 A | 2/1995 | Pisharodi |
| 5,433,718 A | 7/1995 | Brinker |
| 5,443,466 A | 8/1995 | Shah |
| 5,458,638 A | 10/1995 | Kuslich et al. |
| 5,470,334 A | 11/1995 | Ross et al. |
| 5,480,402 A | 1/1996 | Kim |
| 5,569,249 A | 10/1996 | James et al. |
| 5,591,235 A | 1/1997 | Kuslich |
| 5,593,409 A | 1/1997 | Michelson |
| 5,607,424 A | 3/1997 | Tropiano |
| 5,609,635 A | 3/1997 | Michelson |
| 5,609,636 A | 3/1997 | Kohrs et al. |
| 5,626,616 A | 5/1997 | Speece |
| 5,643,264 A | 7/1997 | Sherman et al. |
| 5,645,599 A | 7/1997 | Samani |
| 5,658,337 A | 8/1997 | Kohrs et al. |
| 5,667,510 A | 9/1997 | Combs |
| 5,669,909 A | 9/1997 | Zdeblick et al. |
| 5,672,178 A | 9/1997 | Petersen |
| 5,683,391 A | 11/1997 | Boyd |
| 5,709,683 A | 1/1998 | Bagby |
| 5,713,904 A | 2/1998 | Errico et al. |
| 5,716,358 A | 2/1998 | Ochoa et al. |
| 5,725,581 A | 3/1998 | Brånemark |
| 5,743,912 A | 4/1998 | LaHille et al. |
| 5,759,035 A | 6/1998 | Ricci |
| 5,766,174 A | 6/1998 | Perry |
| 5,766,252 A | 6/1998 | Henry et al. |
| 5,766,261 A | 6/1998 | Neal et al. |
| 5,788,699 A | 8/1998 | Bobst et al. |
| 5,800,440 A | 9/1998 | Stead |
| 5,868,749 A | 2/1999 | Reed |
| 5,897,556 A | 4/1999 | Drewry et al. |
| 5,928,239 A | 7/1999 | Mirza |
| 5,941,885 A | 8/1999 | Jackson |
| 5,961,522 A | 10/1999 | Mehdizadeh |
| 5,961,554 A | 10/1999 | Janson et al. |
| 6,010,507 A | 1/2000 | Rudloff |
| 6,015,409 A | 1/2000 | Jackson |
| 6,030,162 A | 2/2000 | Huebner et al. |
| 6,053,916 A | 4/2000 | Moore |
| 6,056,749 A | 5/2000 | Kuslich |
| 6,066,175 A | 5/2000 | Henderson et al. |
| 6,086,589 A | 7/2000 | Kuslich et al. |
| 6,096,080 A | 8/2000 | Nicholson et al. |
| 6,120,292 A | 9/2000 | Buser et al. |
| 6,120,504 A | 9/2000 | Brumback et al. |
| 6,143,031 A | 11/2000 | Knothe et al. |
| 6,197,062 B1 | 3/2001 | Fenlin |
| 6,206,924 B1 | 3/2001 | Timm |
| 6,210,442 B1 | 4/2001 | Wing et al. |
| 6,214,049 B1 | 4/2001 | Gayer et al. |
| 6,221,074 B1 | 4/2001 | Cole et al. |
| 6,224,607 B1 | 5/2001 | Michelson |
| 6,241,732 B1 | 6/2001 | Overaker et al. |
| 6,264,657 B1 | 7/2001 | Urbahns et al. |
| 6,270,528 B1 | 8/2001 | McKay |
| 6,287,343 B1 | 9/2001 | Kuslich et al. |
| 6,302,885 B1 | 10/2001 | Essiger |
| 6,302,914 B1 | 10/2001 | Michelson |
| 6,306,140 B1 | 10/2001 | Siddiqui |
| 6,319,253 B1 | 11/2001 | Ackeret et al. |
| 6,406,498 B1 | 6/2002 | Tormala et al. |
| 6,409,768 B1 | 6/2002 | Tepic et al. |
| 6,436,139 B1 | 8/2002 | Shapiro et al. |

(56) References Cited

U.S. PATENT DOCUMENTS

| | | |
|---|---|---|
| 6,451,020 B1 | 9/2002 | Zucherman et al. |
| 6,471,707 B1 | 10/2002 | Miller et al. |
| 6,485,518 B1 | 11/2002 | Cornwall et al. |
| 6,497,707 B1 | 12/2002 | Bowman et al. |
| 6,517,541 B1 | 2/2003 | Sesic |
| 6,520,969 B2 | 2/2003 | Lambrecht et al. |
| 6,524,314 B1 | 2/2003 | Dean et al. |
| 6,527,775 B1 | 3/2003 | Warburton |
| 6,556,857 B1 | 4/2003 | Estes et al. |
| 6,558,386 B1 | 5/2003 | Cragg |
| 6,565,566 B1 | 5/2003 | Wagner et al. |
| 6,575,899 B1 | 6/2003 | Foley et al. |
| 6,575,991 B1 | 6/2003 | Chesbrough et al. |
| 6,579,293 B1 | 6/2003 | Chandran |
| 6,582,431 B1 | 6/2003 | Ray |
| 6,582,467 B1 | 6/2003 | Teitelbaum et al. |
| 6,595,998 B2 | 7/2003 | Johnson et al. |
| 6,602,293 B1 | 8/2003 | Biermann et al. |
| 6,605,090 B1 | 8/2003 | Trieu et al. |
| 6,607,530 B1 | 8/2003 | Carl et al. |
| 6,620,163 B1 | 9/2003 | Michelson |
| 6,635,059 B2 | 10/2003 | Randall et al. |
| 6,666,868 B2 | 12/2003 | Fallin |
| 6,669,529 B1 | 12/2003 | Scaries |
| 6,673,075 B2 | 1/2004 | Santilli |
| 6,692,501 B2 | 2/2004 | Michelson |
| 6,712,852 B1 | 3/2004 | Chung et al. |
| 6,723,099 B1 | 4/2004 | Goshert |
| 6,723,100 B2 | 4/2004 | Biedermann et al. |
| 6,740,118 B2 | 5/2004 | Eisermann et al. |
| 6,743,257 B2 | 6/2004 | Castro |
| D493,533 S | 7/2004 | Blain |
| 6,793,656 B1 | 9/2004 | Mathews |
| 6,827,740 B1 | 12/2004 | Michelson |
| 6,984,235 B2 | 1/2006 | Huebner |
| 6,989,033 B1 | 1/2006 | Schmidt |
| 6,991,461 B2 | 1/2006 | Gittleman |
| 6,993,406 B1 | 1/2006 | Cesarano et al. |
| 7,018,416 B2 | 3/2006 | Hanson et al. |
| 7,118,579 B2 | 10/2006 | Michelson |
| 7,147,666 B1 | 12/2006 | Grisoni |
| 7,175,663 B1 | 2/2007 | Stone |
| 7,211,085 B2 | 5/2007 | Michelson |
| 7,223,269 B2 | 5/2007 | Chappuis |
| 7,314,488 B2 | 1/2008 | Reiley |
| 7,335,205 B2 | 2/2008 | Aeschlimann et al. |
| 7,338,500 B2 | 3/2008 | Chappuis |
| 7,396,365 B2 | 7/2008 | Michelson |
| 7,452,359 B1 | 11/2008 | Michelson |
| 7,452,369 B2 | 11/2008 | Barry |
| 7,481,831 B2 | 1/2009 | Bonutt |
| 7,527,649 B1 | 5/2009 | Blain |
| 7,534,254 B1 | 5/2009 | Michelson |
| 7,537,616 B1 | 5/2009 | Branch et al. |
| 7,569,054 B2 | 8/2009 | Michelson |
| 7,569,059 B2 | 8/2009 | Cerundolo |
| 7,601,155 B2 | 10/2009 | Petersen |
| 7,608,097 B2 | 10/2009 | Kyle |
| 7,608,098 B1 | 10/2009 | Stone et al. |
| 7,648,509 B2 | 1/2010 | Stark |
| 7,686,805 B2 | 3/2010 | Michelson |
| 7,699,852 B2 | 4/2010 | Frankel et al. |
| 7,708,761 B2 | 5/2010 | Petersen |
| 7,727,235 B2 | 6/2010 | Contiliano et al. |
| 7,758,646 B2 | 7/2010 | Khandkar et al. |
| 7,780,704 B2 | 8/2010 | Markworth et al. |
| 7,846,162 B2 | 12/2010 | Nelson et al. |
| 7,850,732 B2 | 12/2010 | Heinz |
| 7,857,832 B2 | 12/2010 | Culbert et al. |
| 7,887,565 B2 | 2/2011 | Michelson |
| 7,892,265 B2 | 2/2011 | Perez-Cruet et al. |
| 7,901,439 B2 | 3/2011 | Horton |
| 7,909,832 B2 | 3/2011 | Michelson |
| 7,922,765 B2 | 4/2011 | Reiley |
| 7,942,879 B2 | 5/2011 | Christie et al. |
| 7,951,176 B2 | 5/2011 | Grady et al. |
| 8,052,728 B2 | 11/2011 | Hestad |
| 8,062,365 B2 | 11/2011 | Schwab |
| 8,066,705 B2 | 11/2011 | Michelson |
| 8,066,709 B2 | 11/2011 | Michelson |
| 8,092,505 B2 | 1/2012 | Sommers |
| 8,142,481 B2 | 3/2012 | Warnick |
| 8,202,305 B2 | 6/2012 | Reiley |
| 8,221,499 B2 | 7/2012 | Lazzara et al. |
| 8,257,398 B2 | 9/2012 | Jackson |
| 8,268,099 B2 | 9/2012 | O'Neill et al. |
| 8,308,779 B2 | 11/2012 | Reiley |
| 8,308,783 B2 | 11/2012 | Morris et al. |
| 8,317,862 B2 | 11/2012 | Troger et al. |
| 8,348,950 B2 | 1/2013 | Assell et al. |
| 8,350,186 B2 | 1/2013 | Jones et al. |
| 8,388,667 B2 | 3/2013 | Reiley et al. |
| 8,394,129 B2 | 3/2013 | Morgenstern Lopez |
| 8,398,635 B2 | 3/2013 | Vaidya |
| 8,398,682 B2 | 3/2013 | Jackson et al. |
| 8,414,648 B2 | 4/2013 | Reiley |
| 8,425,570 B2 | 4/2013 | Reiley |
| 8,430,930 B2 | 4/2013 | Hunt |
| 8,444,693 B2 | 5/2013 | Reiley |
| 8,449,585 B2 | 5/2013 | Wallenstein et al. |
| 8,467,851 B2 | 6/2013 | Mire et al. |
| 8,470,004 B2 | 6/2013 | Reiley |
| 8,475,505 B2 | 7/2013 | Nebosky et al. |
| 8,529,608 B2 | 9/2013 | Terrill et al. |
| 8,597,299 B2 | 12/2013 | Farr et al. |
| 8,608,802 B2 | 12/2013 | Bagga et al. |
| D697,209 S | 1/2014 | Walthall et al. |
| 8,641,737 B2 | 2/2014 | Matthis et al. |
| 8,663,332 B1 | 3/2014 | To et al. |
| 8,672,986 B2 | 3/2014 | Klaue et al. |
| 8,734,462 B2 | 5/2014 | Reiley et al. |
| 8,778,026 B2 | 7/2014 | Mauldin |
| 8,840,623 B2 | 9/2014 | Reiley |
| 8,840,651 B2 | 9/2014 | Reiley |
| 8,845,693 B2 | 9/2014 | Smith et al. |
| 8,858,601 B2 | 10/2014 | Reiley |
| 8,888,827 B2 | 11/2014 | Harper et al. |
| 8,894,685 B2 | 11/2014 | Mickiewicz et al. |
| 8,920,477 B2 | 12/2014 | Reiley |
| 8,926,670 B2 | 1/2015 | Jackson |
| 8,936,623 B2 | 1/2015 | Jackson |
| 8,945,190 B2 | 2/2015 | Culbert et al. |
| 8,945,193 B2 | 2/2015 | Kirschman |
| 8,951,254 B2 | 2/2015 | Mayer et al. |
| 8,951,293 B2 | 2/2015 | Glazer et al. |
| 8,951,295 B2 | 2/2015 | Matityahu et al. |
| 8,961,571 B2 | 2/2015 | Lee et al. |
| 8,979,911 B2 | 3/2015 | Martineau et al. |
| 8,986,348 B2 | 3/2015 | Reiley |
| RE45,484 E | 4/2015 | Foley et al. |
| 9,039,743 B2 | 5/2015 | Reiley |
| 9,044,321 B2 | 6/2015 | Mauldin et al. |
| 9,060,876 B1 | 6/2015 | To et al. |
| 9,089,371 B1 | 7/2015 | Faulhaber |
| D738,498 S | 9/2015 | Frey et al. |
| 9,131,955 B2 | 9/2015 | Swofford |
| 9,149,286 B1 | 10/2015 | Greenhalgh et al. |
| 9,198,676 B2 | 12/2015 | Pilgeram et al. |
| 9,220,535 B2 | 12/2015 | Röbling et al. |
| 9,314,286 B2 | 4/2016 | Bottlang et al. |
| 9,314,348 B2 | 4/2016 | Emstad |
| 9,358,047 B2 | 6/2016 | Mishra et al. |
| 9,358,057 B1 | 6/2016 | Whipple et al. |
| 9,375,243 B1 | 6/2016 | Vestgaarden |
| 9,375,323 B2 | 6/2016 | Reiley |
| 9,445,852 B2 | 9/2016 | Sweeney |
| 9,451,999 B2 | 9/2016 | Simpson et al. |
| 9,452,065 B1 | 9/2016 | Lawson |
| 9,486,264 B2 | 11/2016 | Reiley et al. |
| 9,492,201 B2 | 11/2016 | Reiley |
| 9,498,264 B2 | 11/2016 | Harshman et al. |
| 9,510,872 B2 | 12/2016 | Donner et al. |
| 9,517,095 B2 | 12/2016 | Vaidya |
| 9,526,548 B2 | 12/2016 | Asfora |

(56) References Cited

U.S. PATENT DOCUMENTS

| | | |
|---|---|---|
| 9,554,909 B2 | 1/2017 | Donner |
| 9,561,063 B2 | 2/2017 | Reiley |
| 9,566,100 B2 | 2/2017 | Asfora |
| 9,603,613 B2 | 3/2017 | Schoenefeld et al. |
| 9,603,644 B2 | 3/2017 | Sweeney |
| D783,821 S | 4/2017 | Folsom et al. |
| 9,615,856 B2 | 4/2017 | Arnett et al. |
| 9,622,783 B2 | 4/2017 | Reiley et al. |
| 9,655,656 B2 | 5/2017 | Whipple |
| 9,662,124 B2 | 5/2017 | Assell et al. |
| 9,662,128 B2 | 5/2017 | Reiley |
| 9,662,157 B2 | 5/2017 | Schneider et al. |
| 9,662,158 B2 | 5/2017 | Reiley |
| 9,675,394 B2 | 6/2017 | Reiley |
| 9,743,969 B2 | 8/2017 | Reiley |
| 9,757,154 B2 | 9/2017 | Donner et al. |
| 9,763,695 B2 | 9/2017 | Mirda |
| 9,763,802 B2 | 9/2017 | Baynham |
| 9,775,648 B2 | 10/2017 | Greenberg et al. |
| 9,788,961 B2 | 10/2017 | Donner et al. |
| 9,808,298 B2 | 11/2017 | Stroncek et al. |
| 9,808,299 B2 | 11/2017 | Goel et al. |
| 9,808,337 B2 | 11/2017 | Housman et al. |
| 9,820,789 B2 | 11/2017 | Reiley |
| 9,833,321 B2 | 12/2017 | Rindal et al. |
| 9,839,448 B2 | 12/2017 | Reckling et al. |
| 9,848,889 B2 | 12/2017 | Taylor et al. |
| 9,848,892 B2 | 12/2017 | Biedermann et al. |
| 9,883,874 B1 | 2/2018 | Vestgaarden |
| 9,888,911 B2 | 2/2018 | Siegal |
| 9,936,983 B2 | 4/2018 | Mesiwala et al. |
| 9,949,776 B2 | 4/2018 | Mobasser et al. |
| 9,949,843 B2 | 4/2018 | Reiley et al. |
| D816,843 S | 5/2018 | Lewis |
| 9,956,013 B2 | 5/2018 | Reiley et al. |
| 9,993,276 B2 | 6/2018 | Russell |
| 9,993,277 B2 | 6/2018 | Krinke et al. |
| 9,999,449 B2 | 6/2018 | Bonutti |
| 10,004,547 B2 | 6/2018 | Reiley |
| 10,034,676 B2 | 7/2018 | Donner |
| 10,058,430 B2 | 8/2018 | Donner et al. |
| 10,064,670 B2 | 9/2018 | Mootien et al. |
| D831,828 S | 10/2018 | Horton et al. |
| 10,166,022 B2 | 1/2019 | Early et al. |
| 10,166,033 B2 | 1/2019 | Reiley et al. |
| 10,179,014 B1 | 1/2019 | Menmuir et al. |
| 10,188,403 B2 | 1/2019 | Mirochinik et al. |
| 10,188,442 B2 | 1/2019 | Mazel |
| 10,194,951 B2 | 2/2019 | Jackson et al. |
| 10,194,962 B2 | 2/2019 | Schneider et al. |
| 10,201,427 B2 | 2/2019 | Mauldin et al. |
| 10,219,841 B1 | 3/2019 | Compton et al. |
| 10,219,885 B2 | 3/2019 | Mamo et al. |
| D846,977 S | 4/2019 | Williams et al. |
| D847,336 S | 4/2019 | Asfora et al. |
| 10,245,044 B2 | 4/2019 | Petersen |
| 10,245,076 B2 | 4/2019 | Fitzpatrick |
| 10,245,087 B2 | 4/2019 | Donner et al. |
| 10,258,380 B2 | 4/2019 | Sinha |
| 10,258,393 B2 | 4/2019 | Caploon et al. |
| 10,258,394 B2 | 4/2019 | Harshman et al. |
| 10,271,882 B2 | 4/2019 | Biedermann et al. |
| D847,994 S | 5/2019 | Asfora et al. |
| 10,278,737 B2 | 5/2019 | Smith |
| 10,285,745 B2 | 5/2019 | Cummins et al. |
| 10,292,778 B2 | 5/2019 | Kostrzewski et al. |
| D850,616 S | 6/2019 | Asfora et al. |
| 10,314,631 B2 | 6/2019 | Gonzalez Blohm et al. |
| 10,321,937 B2 | 6/2019 | Cormier et al. |
| 10,321,945 B2 | 6/2019 | Schifano et al. |
| 10,335,202 B2 | 7/2019 | Ziolo et al. |
| 10,335,204 B2 | 7/2019 | Matthis et al. |
| 10,335,206 B2 | 7/2019 | Nichols et al. |
| 10,335,211 B2 | 7/2019 | Chan et al. |
| 10,335,212 B2 | 7/2019 | Paolino et al. |
| 10,335,216 B2 | 7/2019 | Mari et al. |
| 10,335,217 B2 | 7/2019 | Lindner |
| 10,342,586 B2 | 7/2019 | Schneider |
| 10,349,983 B2 | 7/2019 | Purcell et al. |
| 10,349,986 B2 | 7/2019 | Wall et al. |
| 10,357,287 B2 | 7/2019 | Schlaepfer et al. |
| 10,363,070 B2 | 7/2019 | Jackson et al. |
| 10,363,073 B2 | 7/2019 | Raina et al. |
| 10,363,140 B2 | 7/2019 | Mauldin et al. |
| 10,363,143 B2 | 7/2019 | Neubardt |
| 10,368,919 B2 | 8/2019 | Pham et al. |
| 10,413,332 B2 | 9/2019 | Schumacher et al. |
| 10,426,533 B2 | 10/2019 | Mauldin et al. |
| 10,426,539 B2 | 10/2019 | Schifano et al. |
| 10,433,880 B2 | 10/2019 | Donner et al. |
| 10,456,268 B2 | 10/2019 | Mercier et al. |
| 10,463,402 B2 | 11/2019 | Biester et al. |
| 10,478,227 B2 | 11/2019 | Leff et al. |
| 10,485,596 B2 | 11/2019 | Koller et al. |
| 10,492,841 B2 | 12/2019 | Hartdegen et al. |
| 10,492,921 B2 | 12/2019 | McShane, III et al. |
| 10,517,734 B2 | 12/2019 | Donner |
| 10,531,898 B2 | 1/2020 | Boulot |
| 10,531,904 B2 | 1/2020 | Kolb |
| 10,537,340 B2 | 1/2020 | Mirochinik et al. |
| D875,931 S | 2/2020 | Asfora et al. |
| 10,555,758 B2 | 2/2020 | Magee et al. |
| 10,588,676 B2 | 3/2020 | Kang et al. |
| 10,588,677 B2 | 3/2020 | McDonnell |
| 10,595,917 B2 | 3/2020 | Loftus |
| 10,596,003 B2 | 3/2020 | Donner et al. |
| 10,603,054 B2 | 3/2020 | Asfora et al. |
| 10,603,055 B2 | 3/2020 | Donner et al. |
| 10,603,087 B2 | 3/2020 | Brenzel et al. |
| 10,603,176 B2 | 3/2020 | Arnold et al. |
| 10,610,275 B2 | 4/2020 | Brianza |
| 10,610,276 B2 | 4/2020 | Lutz |
| 10,610,370 B2 | 4/2020 | Baynham |
| 10,610,728 B2 | 4/2020 | Fano et al. |
| 10,617,453 B2 | 4/2020 | Beckett et al. |
| 10,653,454 B2 | 5/2020 | Frey et al. |
| 10,653,455 B2 | 5/2020 | Lehman et al. |
| 10,660,657 B2 | 5/2020 | Slobitker et al. |
| 10,660,679 B2 | 5/2020 | Kang et al. |
| 10,660,684 B2 | 5/2020 | Kang et al. |
| 10,667,923 B2 | 6/2020 | Sullivan et al. |
| 10,682,131 B2 | 6/2020 | Fallin et al. |
| 10,682,150 B2 | 6/2020 | Stark |
| 10,682,437 B2 | 6/2020 | Roth |
| 10,711,334 B2 | 7/2020 | Patel et al. |
| 10,729,475 B2 | 8/2020 | Childs |
| 10,729,482 B2 | 8/2020 | Fantigrossi et al. |
| 10,743,995 B2 | 8/2020 | Fallin et al. |
| D895,111 S | 9/2020 | Frey et al. |
| 10,758,283 B2 | 9/2020 | Frey et al. |
| 10,758,285 B2 | 9/2020 | Geist et al. |
| 10,792,074 B2 | 10/2020 | Jackson |
| 10,799,277 B2 | 10/2020 | Kulper et al. |
| 10,799,367 B2 | 10/2020 | Vrionis et al. |
| 10,806,597 B2 | 10/2020 | Soumac et al. |
| 10,842,511 B2 | 11/2020 | Patel et al. |
| 10,842,634 B2 | 11/2020 | Pasini et al. |
| D904,615 S | 12/2020 | Asfora et al. |
| D905,232 S | 12/2020 | Schifano et al. |
| 10,856,922 B2 | 12/2020 | Loke et al. |
| 10,864,029 B2 | 12/2020 | Redmond et al. |
| 10,898,333 B2 | 1/2021 | Cordaro |
| 10,905,472 B2 | 2/2021 | Mari et al. |
| 10,912,654 B2 | 2/2021 | Scheland |
| 10,932,838 B2 | 3/2021 | Mehl et al. |
| 10,939,944 B2 | 3/2021 | Wapner et al. |
| 10,959,758 B2 | 3/2021 | Mesiwala et al. |
| 10,959,830 B2 | 3/2021 | Williams et al. |
| 10,987,142 B2 | 4/2021 | Poelstra et al. |
| 10,993,754 B2 | 5/2021 | Kuntz et al. |
| 10,993,757 B2 | 5/2021 | Schifano et al. |
| 11,006,985 B2 | 5/2021 | Caploon et al. |
| D921,898 S | 6/2021 | Schifano et al. |
| D922,568 S | 6/2021 | Schifano et al. |

(56) References Cited

U.S. PATENT DOCUMENTS

| | | |
|---|---|---|
| 11,033,309 B2 | 6/2021 | Zadeh |
| 11,052,229 B2 | 7/2021 | Althoff et al. |
| 11,058,443 B2 | 7/2021 | Siccardi et al. |
| 11,071,573 B2 | 7/2021 | Schneider et al. |
| 11,116,519 B2 | 9/2021 | Sand et al. |
| 11,116,557 B2 | 9/2021 | Zander et al. |
| 11,147,591 B2 | 10/2021 | Jackson |
| 11,147,597 B2 | 10/2021 | Jackson |
| 11,147,688 B2 | 10/2021 | Reckling et al. |
| D935,025 S | 11/2021 | Schifano et al. |
| 11,172,939 B2 | 11/2021 | Donner et al. |
| 11,224,467 B2 | 1/2022 | Peterson et al. |
| 11,259,854 B2 | 3/2022 | Thores et al. |
| 11,266,767 B2 | 3/2022 | Roth et al. |
| 11,273,043 B1 | 3/2022 | Abbasi |
| 11,284,798 B2 | 3/2022 | Donner et al. |
| 11,284,887 B2 | 3/2022 | Hartdegen et al. |
| 11,298,747 B2 | 4/2022 | Klein et al. |
| D951,455 S | 5/2022 | Ginn |
| 11,419,653 B2 | 8/2022 | Castro |
| 11,419,654 B2 | 8/2022 | Castro |
| 11,452,548 B2 | 9/2022 | Harshman et al. |
| 2001/0012942 A1 | 8/2001 | Estes et al. |
| 2001/0046518 A1 | 11/2001 | Sawhney |
| 2001/0047207 A1 | 11/2001 | Michelson |
| 2001/0049529 A1 | 12/2001 | Cachia et al. |
| 2002/0019637 A1 | 2/2002 | Frey et al. |
| 2002/0029043 A1 | 3/2002 | Ahrens et al. |
| 2002/0038123 A1 | 3/2002 | Visotsky et al. |
| 2002/0049497 A1 | 4/2002 | Mason |
| 2002/0077641 A1 | 6/2002 | Michelson |
| 2002/0082598 A1 | 6/2002 | Teitelbaum |
| 2002/0120275 A1 | 8/2002 | Schmieding et al. |
| 2002/0120335 A1 | 8/2002 | Angelucci et al. |
| 2002/0128652 A1 | 9/2002 | Ferree |
| 2002/0143334 A1 | 10/2002 | von Hoffmann et al. |
| 2002/0143335 A1 | 10/2002 | von Hoffmann et al. |
| 2002/0151903 A1 | 10/2002 | Takei et al. |
| 2002/0169507 A1 | 11/2002 | Malone |
| 2002/0183858 A1 | 12/2002 | Contiliano et al. |
| 2002/0198527 A1 | 12/2002 | Mückter |
| 2003/0018336 A1 | 1/2003 | Vandewalle |
| 2003/0032961 A1 | 2/2003 | Pelo et al. |
| 2003/0050642 A1 | 3/2003 | Schmieding et al. |
| 2003/0065332 A1 | 4/2003 | TenHuisen et al. |
| 2003/0074000 A1 | 4/2003 | Roth et al. |
| 2003/0078660 A1 | 4/2003 | Clifford et al. |
| 2003/0083668 A1 | 5/2003 | Rogers et al. |
| 2003/0083688 A1 | 5/2003 | Simonson |
| 2003/0088251 A1 | 5/2003 | Braun et al. |
| 2003/0097131 A1 | 5/2003 | Schon et al. |
| 2003/0139815 A1 | 7/2003 | Grooms et al. |
| 2003/0181979 A1 | 9/2003 | Ferree |
| 2003/0181982 A1 | 9/2003 | Kuslich |
| 2003/0199983 A1 | 10/2003 | Michelson |
| 2003/0229358 A1 | 12/2003 | Errico et al. |
| 2003/0233146 A1 | 12/2003 | Grinberg et al. |
| 2003/0233147 A1 | 12/2003 | Nicholson et al. |
| 2004/0010315 A1 | 1/2004 | Song |
| 2004/0024458 A1 | 2/2004 | Senegas et al. |
| 2004/0034422 A1 | 2/2004 | Errico et al. |
| 2004/0073216 A1 | 4/2004 | Lieberman |
| 2004/0073314 A1 | 4/2004 | White et al. |
| 2004/0082955 A1 | 4/2004 | Zirkle |
| 2004/0087948 A1 | 5/2004 | Suddaby |
| 2004/0097927 A1 | 5/2004 | Yeung et al. |
| 2004/0106925 A1 | 6/2004 | Culbert |
| 2004/0117022 A1 | 6/2004 | Marnay et al. |
| 2004/0127990 A1 | 7/2004 | Bartish, Jr. et al. |
| 2004/0138750 A1 | 7/2004 | Mitchell |
| 2004/0138753 A1 | 7/2004 | Ferree |
| 2004/0147929 A1 | 7/2004 | Biedermann et al. |
| 2004/0158324 A1 | 8/2004 | Lange |
| 2004/0176287 A1 | 9/2004 | Harrison et al. |
| 2004/0176853 A1 | 9/2004 | Sennett et al. |
| 2004/0181282 A1 | 9/2004 | Zucherman et al. |
| 2004/0186572 A1 | 9/2004 | Lange et al. |
| 2004/0210221 A1 | 10/2004 | Kozak et al. |
| 2004/0225360 A1 | 11/2004 | Malone |
| 2004/0230305 A1 | 11/2004 | Gorensek et al. |
| 2004/0260286 A1 | 12/2004 | Ferree |
| 2004/0267369 A1 | 12/2004 | Lyons et al. |
| 2005/0015059 A1 | 1/2005 | Sweeney |
| 2005/0015146 A1 | 1/2005 | Louis et al. |
| 2005/0033435 A1 | 2/2005 | Belliard et al. |
| 2005/0037319 A1 | 2/2005 | Bulard et al. |
| 2005/0049590 A1 | 3/2005 | Alleyne et al. |
| 2005/0055023 A1 | 3/2005 | Sohngen et al. |
| 2005/0070905 A1 | 3/2005 | Donnelly et al. |
| 2005/0071004 A1 | 3/2005 | Re et al. |
| 2005/0075641 A1 | 4/2005 | Singhatat et al. |
| 2005/0080415 A1 | 4/2005 | Keyer et al. |
| 2005/0107878 A1 | 5/2005 | Conchy |
| 2005/0112397 A1 | 5/2005 | Rolfe et al. |
| 2005/0113919 A1 | 5/2005 | Cragg et al. |
| 2005/0124993 A1 | 6/2005 | Chappuis |
| 2005/0131409 A1 | 6/2005 | Chervitz et al. |
| 2005/0137605 A1 | 6/2005 | Assell et al. |
| 2005/0143837 A1 | 6/2005 | Ferree |
| 2005/0149192 A1 | 7/2005 | Zucherman et al. |
| 2005/0159749 A1 | 7/2005 | Levy et al. |
| 2005/0159812 A1 | 7/2005 | Dinger et al. |
| 2005/0165398 A1 | 7/2005 | Reiley |
| 2005/0192572 A1 | 9/2005 | Abdelgany et al. |
| 2005/0216082 A1 | 9/2005 | Wilson et al. |
| 2005/0228384 A1 | 10/2005 | Zucherman et al. |
| 2005/0246021 A1 | 11/2005 | Ringeisen et al. |
| 2005/0251146 A1 | 11/2005 | Martz et al. |
| 2005/0273101 A1 | 12/2005 | Schumacher |
| 2005/0277940 A1 | 12/2005 | Neff |
| 2006/0004396 A1 | 1/2006 | Easley et al. |
| 2006/0036247 A1 | 2/2006 | Michelson |
| 2006/0036251 A1 | 2/2006 | Reiley |
| 2006/0036252 A1 | 2/2006 | Baynham et al. |
| 2006/0054171 A1 | 3/2006 | Dall |
| 2006/0058793 A1 | 3/2006 | Michelson |
| 2006/0058800 A1 | 3/2006 | Ainsworth et al. |
| 2006/0062825 A1 | 3/2006 | Maccecchini |
| 2006/0084986 A1 | 4/2006 | Grinberg et al. |
| 2006/0089656 A1 | 4/2006 | Allard et al. |
| 2006/0111779 A1 | 5/2006 | Petersen |
| 2006/0129247 A1 | 6/2006 | Brown et al. |
| 2006/0142772 A1 | 6/2006 | Ralph et al. |
| 2006/0161163 A1 | 7/2006 | Shino |
| 2006/0178673 A1 | 8/2006 | Curran |
| 2006/0195094 A1 | 8/2006 | McGraw et al. |
| 2006/0217717 A1 | 9/2006 | Whipple |
| 2006/0241600 A1 | 10/2006 | Ensign et al. |
| 2006/0241776 A1 | 10/2006 | Brown et al. |
| 2006/0271054 A1 | 11/2006 | Sucec et al. |
| 2006/0293662 A1 | 12/2006 | Boyer, II et al. |
| 2007/0027544 A1 | 2/2007 | McCord et al. |
| 2007/0038219 A1 | 2/2007 | Matthis et al. |
| 2007/0049933 A1 | 3/2007 | Ahn et al. |
| 2007/0066977 A1 | 3/2007 | Assell et al. |
| 2007/0083265 A1 | 4/2007 | Malone |
| 2007/0088362 A1 | 4/2007 | Bonutti et al. |
| 2007/0093841 A1 | 4/2007 | Hoogland |
| 2007/0093898 A1 | 4/2007 | Schwab et al. |
| 2007/0106383 A1 | 5/2007 | Abdou |
| 2007/0149976 A1 | 6/2007 | Hale et al. |
| 2007/0156144 A1 | 7/2007 | Ulrich et al. |
| 2007/0156241 A1 | 7/2007 | Reiley et al. |
| 2007/0156246 A1 | 7/2007 | Meswania et al. |
| 2007/0161985 A1 | 7/2007 | Demakas et al. |
| 2007/0161989 A1 | 7/2007 | Heinz et al. |
| 2007/0173820 A1 | 7/2007 | Trieu |
| 2007/0219634 A1 | 9/2007 | Greenhalgh et al. |
| 2007/0233080 A1 | 10/2007 | Na et al. |
| 2007/0233146 A1 | 10/2007 | Henniges et al. |
| 2007/0233247 A1 | 10/2007 | Schwab |
| 2007/0250166 A1 | 10/2007 | McKay |
| 2007/0270833 A1 | 11/2007 | Bonutti et al. |
| 2007/0270879 A1 | 11/2007 | Isaza et al. |

(56) References Cited

U.S. PATENT DOCUMENTS

| | | |
|---|---|---|
| 2007/0282443 A1 | 12/2007 | Globerman et al. |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0021461 A1 | 1/2008 | Barker et al. |
| 2008/0021480 A1 | 1/2008 | Chin et al. |
| 2008/0065093 A1 | 3/2008 | Assell et al. |
| 2008/0065215 A1 | 3/2008 | Reiley |
| 2008/0071356 A1 | 3/2008 | Greenhalgh et al. |
| 2008/0109083 A1 | 5/2008 | Van Hoeck et al. |
| 2008/0125868 A1 | 5/2008 | Branemark et al. |
| 2008/0132901 A1 | 6/2008 | Recoules-Arche et al. |
| 2008/0140082 A1 | 6/2008 | Erdem et al. |
| 2008/0147079 A1 | 6/2008 | Chin et al. |
| 2008/0154374 A1 | 6/2008 | Labrom |
| 2008/0161810 A1 | 7/2008 | Melkent |
| 2008/0183204 A1 | 7/2008 | Greenhalgh et al. |
| 2008/0234758 A1 | 9/2008 | Fisher et al. |
| 2008/0255562 A1 | 10/2008 | Gil et al. |
| 2008/0255618 A1 | 10/2008 | Fisher et al. |
| 2008/0255622 A1 | 10/2008 | Mickiewicz et al. |
| 2008/0255664 A1 | 10/2008 | Hogendijk et al. |
| 2008/0255666 A1 | 10/2008 | Fisher et al. |
| 2008/0255667 A1 | 10/2008 | Horton |
| 2008/0275454 A1 | 11/2008 | Geibel |
| 2008/0294202 A1 | 11/2008 | Peterson et al. |
| 2008/0306554 A1 | 12/2008 | McKinley |
| 2009/0012529 A1 | 1/2009 | Blain et al. |
| 2009/0018660 A1 | 1/2009 | Roush |
| 2009/0024174 A1 | 1/2009 | Stark |
| 2009/0036927 A1 | 2/2009 | Vestgaarden |
| 2009/0037148 A1 | 2/2009 | Lin et al. |
| 2009/0043393 A1 | 2/2009 | Duggal et al. |
| 2009/0082810 A1 | 3/2009 | Bhatnagar et al. |
| 2009/0082869 A1 | 3/2009 | Slemker et al. |
| 2009/0099602 A1 | 4/2009 | Aflatoon |
| 2009/0099610 A1 | 4/2009 | Johnson et al. |
| 2009/0105770 A1 | 4/2009 | Berrevooets et al. |
| 2009/0118771 A1 | 5/2009 | Gonzalez-Hernandez |
| 2009/0131986 A1 | 5/2009 | Lee et al. |
| 2009/0138053 A1 | 5/2009 | Assell et al. |
| 2009/0157119 A1 | 6/2009 | Hale |
| 2009/0163920 A1 | 6/2009 | Hochschuler et al. |
| 2009/0171394 A1 | 7/2009 | Adbou |
| 2009/0187247 A1 | 7/2009 | Metcalf, Jr. et al. |
| 2009/0216238 A1 | 8/2009 | Stark |
| 2009/0270929 A1 | 10/2009 | Suddaby |
| 2009/0287254 A1 | 11/2009 | Nayet et al. |
| 2009/0312798 A1 | 12/2009 | Varela |
| 2009/0319043 A1 | 12/2009 | McDevitt et al. |
| 2009/0324678 A1 | 12/2009 | Thorne et al. |
| 2010/0003638 A1 | 1/2010 | Collins et al. |
| 2010/0022535 A1 | 1/2010 | Lee et al. |
| 2010/0076502 A1 | 3/2010 | Guyer et al. |
| 2010/0081107 A1 | 4/2010 | Bagambisa et al. |
| 2010/0094290 A1 | 4/2010 | Vaidya |
| 2010/0094295 A1 | 4/2010 | Schnieders et al. |
| 2010/0094420 A1 | 4/2010 | Grohowski |
| 2010/0106194 A1 | 4/2010 | Bonutti et al. |
| 2010/0106195 A1 | 4/2010 | Serhan et al. |
| 2010/0114174 A1 | 5/2010 | Jones et al. |
| 2010/0114317 A1 | 5/2010 | Lambrecht et al. |
| 2010/0131011 A1 | 5/2010 | Stark |
| 2010/0137990 A1 | 6/2010 | Apatsidis et al. |
| 2010/0145461 A1 | 6/2010 | Landry et al. |
| 2010/0160977 A1 | 6/2010 | Gephart et al. |
| 2010/0168798 A1 | 7/2010 | Clineff et al. |
| 2010/0191292 A1 | 7/2010 | DeMeo et al. |
| 2010/0262242 A1 | 10/2010 | Chavatte et al. |
| 2010/0268228 A1 | 10/2010 | Petersen |
| 2010/0280619 A1 | 11/2010 | Yuan et al. |
| 2010/0280622 A1 | 11/2010 | McKinley |
| 2010/0286778 A1 | 11/2010 | Eisermann et al. |
| 2010/0331851 A1 | 12/2010 | Huene |
| 2010/0331893 A1 | 12/2010 | Geist et al. |
| 2011/0009869 A1 | 1/2011 | Marino et al. |
| 2011/0009966 A1 | 1/2011 | Michelson |
| 2011/0022089 A1 | 1/2011 | Assell et al. |
| 2011/0029019 A1 | 2/2011 | Ainsworth et al. |
| 2011/0040362 A1 | 2/2011 | Godara et al. |
| 2011/0046737 A1 | 2/2011 | Teisen |
| 2011/0060373 A1 | 3/2011 | Russell et al. |
| 2011/0060375 A1 | 3/2011 | Bonutti |
| 2011/0066190 A1 | 3/2011 | Schaller et al. |
| 2011/0082551 A1 | 4/2011 | Kraus |
| 2011/0093020 A1 | 4/2011 | Wu |
| 2011/0098747 A1 | 4/2011 | Donner et al. |
| 2011/0098816 A1 | 4/2011 | Jacob et al. |
| 2011/0098817 A1 | 4/2011 | Eckhardt et al. |
| 2011/0106175 A1 | 5/2011 | Rezach |
| 2011/0153018 A1 | 6/2011 | Walters et al. |
| 2011/0160866 A1 | 6/2011 | Laurence et al. |
| 2011/0178561 A1 | 7/2011 | Roh |
| 2011/0184417 A1 | 7/2011 | Kitch et al. |
| 2011/0184518 A1 | 7/2011 | Trieu |
| 2011/0184519 A1 | 7/2011 | Trieu |
| 2011/0184520 A1 | 7/2011 | Trieu |
| 2011/0196372 A1 | 8/2011 | Murase |
| 2011/0213432 A1 | 9/2011 | Geist et al. |
| 2011/0230966 A1 | 9/2011 | Trieu |
| 2011/0238074 A1 | 9/2011 | Ek |
| 2011/0238124 A1 | 9/2011 | Richelsoph |
| 2011/0238181 A1 | 9/2011 | Trieu |
| 2011/0245930 A1 | 10/2011 | Alley et al. |
| 2011/0257755 A1 | 10/2011 | Bellemere et al. |
| 2011/0264229 A1 | 10/2011 | Donner |
| 2011/0276098 A1 | 11/2011 | Biedermann et al. |
| 2011/0295272 A1 | 12/2011 | Assell et al. |
| 2011/0295370 A1 | 12/2011 | Suh et al. |
| 2011/0313471 A1 | 12/2011 | McLean et al. |
| 2011/0313532 A1 | 12/2011 | Hunt |
| 2011/0319995 A1 | 12/2011 | Voellmicke et al. |
| 2012/0004730 A1 | 1/2012 | Castro |
| 2012/0035667 A1 | 2/2012 | Van Nortwick et al. |
| 2012/0083887 A1 | 4/2012 | Purcell et al. |
| 2012/0095560 A1 | 4/2012 | Donner |
| 2012/0179256 A1 | 7/2012 | Reiley |
| 2012/0191191 A1 | 7/2012 | Trieu |
| 2012/0215315 A1 | 8/2012 | Hochschuler et al. |
| 2012/0226318 A1 | 9/2012 | Wenger et al. |
| 2012/0253398 A1 | 10/2012 | Metcalf et al. |
| 2012/0259372 A1 | 10/2012 | Glazer et al. |
| 2012/0271424 A1 | 10/2012 | Crawford |
| 2012/0277866 A1 | 11/2012 | Kalluri et al. |
| 2012/0296428 A1 | 11/2012 | Donner |
| 2012/0323285 A1 | 12/2012 | Assell et al. |
| 2013/0018427 A1 | 1/2013 | Pham et al. |
| 2013/0030456 A1 | 1/2013 | Assell et al. |
| 2013/0030529 A1 | 1/2013 | Hunt |
| 2013/0035727 A1 | 2/2013 | Datta |
| 2013/0053852 A1 | 2/2013 | Greenhalgh et al. |
| 2013/0053854 A1 | 2/2013 | Schoenefeld et al. |
| 2013/0053902 A1 | 2/2013 | Trudeau |
| 2013/0053963 A1 | 2/2013 | Davenport |
| 2013/0072984 A1 | 3/2013 | Robinson |
| 2013/0085535 A1 | 4/2013 | Greenhalgh et al. |
| 2013/0096683 A1 | 4/2013 | Kube |
| 2013/0116793 A1 | 5/2013 | Kloss |
| 2013/0123850 A1 | 5/2013 | Schoenefeld et al. |
| 2013/0123935 A1 | 5/2013 | Hunt et al. |
| 2013/0131678 A1 | 5/2013 | Dahners |
| 2013/0144343 A1 | 6/2013 | Arnett et al. |
| 2013/0158609 A1 | 6/2013 | Mikhail et al. |
| 2013/0172736 A1 | 7/2013 | Abdou |
| 2013/0197590 A1 | 8/2013 | Assell et al. |
| 2013/0203088 A1 | 8/2013 | Baerlecken et al. |
| 2013/0218215 A1 | 8/2013 | Ginn et al. |
| 2013/0218282 A1 | 8/2013 | Hunt |
| 2013/0231746 A1 | 9/2013 | Ginn et al. |
| 2013/0237988 A1 | 9/2013 | Mauldin |
| 2013/0245703 A1 | 9/2013 | Warren et al. |
| 2013/0245763 A1 | 9/2013 | Mauldin |
| 2013/0267836 A1 | 10/2013 | Mauldin et al. |
| 2013/0267961 A1 | 10/2013 | Mauldin et al. |

(56) References Cited

U.S. PATENT DOCUMENTS

| | | |
|---|---|---|
| 2013/0267989 A1 | 10/2013 | Mauldin et al. |
| 2013/0274890 A1 | 10/2013 | McKay |
| 2013/0325129 A1 | 12/2013 | Huang |
| 2014/0012334 A1 | 1/2014 | Armstrong et al. |
| 2014/0012340 A1 | 1/2014 | Beck et al. |
| 2014/0012384 A1 | 1/2014 | Kana et al. |
| 2014/0031934 A1 | 1/2014 | Trieu |
| 2014/0031935 A1 | 1/2014 | Donner et al. |
| 2014/0031938 A1 | 1/2014 | Lechmann et al. |
| 2014/0031939 A1 | 1/2014 | Wolfe et al. |
| 2014/0046380 A1 | 2/2014 | Asfora |
| 2014/0074175 A1 | 3/2014 | Ehler et al. |
| 2014/0088596 A1 | 3/2014 | Assell et al. |
| 2014/0088707 A1 | 3/2014 | Donner et al. |
| 2014/0121776 A1 | 5/2014 | Hunt |
| 2014/0135927 A1 | 5/2014 | Pavlov et al. |
| 2014/0142700 A1 | 5/2014 | Donner et al. |
| 2014/0172027 A1 | 6/2014 | Biedermann et al. |
| 2014/0200618 A1 | 7/2014 | Donner et al. |
| 2014/0207240 A1 | 7/2014 | Stoffman et al. |
| 2014/0257294 A1 | 9/2014 | Gedet et al. |
| 2014/0257408 A1 | 9/2014 | Trieu et al. |
| 2014/0276846 A1* | 9/2014 | Mauldin ............ A61B 17/1664 606/80 |
| 2014/0276851 A1 | 9/2014 | Schneider et al. |
| 2014/0277139 A1 | 9/2014 | Vrionis et al. |
| 2014/0277165 A1 | 9/2014 | Katzman et al. |
| 2014/0277460 A1 | 9/2014 | Schifano et al. |
| 2014/0277462 A1 | 9/2014 | Yerby et al. |
| 2014/0277463 A1 | 9/2014 | Yerby et al. |
| 2014/0288649 A1 | 9/2014 | Hunt |
| 2014/0288650 A1 | 9/2014 | Hunt |
| 2014/0296982 A1 | 10/2014 | Cheng |
| 2014/0330382 A1 | 11/2014 | Mauldin |
| 2014/0364917 A1 | 12/2014 | Sandstrom et al. |
| 2015/0012051 A1 | 1/2015 | Warren et al. |
| 2015/0039037 A1 | 2/2015 | Donner et al. |
| 2015/0080951 A1 | 3/2015 | Yeh |
| 2015/0080972 A1 | 3/2015 | Chin et al. |
| 2015/0094765 A1 | 4/2015 | Donner et al. |
| 2015/0112444 A1 | 4/2015 | Aksu |
| 2015/0147397 A1 | 5/2015 | Altschuler |
| 2015/0150683 A1 | 6/2015 | Donner et al. |
| 2015/0173805 A1 | 6/2015 | Donner et al. |
| 2015/0173904 A1 | 6/2015 | Stark |
| 2015/0182268 A1 | 7/2015 | Donner et al. |
| 2015/0190149 A1 | 7/2015 | Assell et al. |
| 2015/0190187 A1 | 7/2015 | Parent et al. |
| 2015/0209094 A1 | 7/2015 | Anderson |
| 2015/0216566 A1 | 8/2015 | Mikhail et al. |
| 2015/0238203 A1 | 8/2015 | Asfora |
| 2015/0250513 A1 | 9/2015 | De Lavigne Sainte |
| 2015/0250611 A1 | 9/2015 | Schifano et al. |
| 2015/0250612 A1 | 9/2015 | Schifano et al. |
| 2015/0257892 A1 | 9/2015 | Lechmann et al. |
| 2015/0313720 A1 | 11/2015 | Lorio |
| 2015/0320450 A1 | 11/2015 | Mootien et al. |
| 2015/0320451 A1 | 11/2015 | Mootien et al. |
| 2015/0320469 A1 | 11/2015 | Biedermann et al. |
| 2015/0342753 A1 | 12/2015 | Donner et al. |
| 2016/0000488 A1 | 1/2016 | Cross, III |
| 2016/0022429 A1 | 1/2016 | Greenhalgh et al. |
| 2016/0095711 A1 | 4/2016 | Castro |
| 2016/0095721 A1 | 4/2016 | Schell et al. |
| 2016/0100870 A1 | 4/2016 | Lavigne et al. |
| 2016/0106477 A1 | 4/2016 | Hynes et al. |
| 2016/0106479 A1 | 4/2016 | Hynes et al. |
| 2016/0120661 A1 | 5/2016 | Schell et al. |
| 2016/0143671 A1 | 5/2016 | Jimenez |
| 2016/0016630 A1 | 6/2016 | Papangelou et al. |
| 2016/0157908 A1 | 6/2016 | Cawley et al. |
| 2016/0166301 A1 | 6/2016 | Papangelou et al. |
| 2016/0175113 A1 | 6/2016 | Lins |
| 2016/0184103 A1 | 6/2016 | Fonte et al. |
| 2016/0213487 A1 | 7/2016 | Wilson et al. |
| 2016/0242820 A1 | 8/2016 | Whipple et al. |
| 2016/0242912 A1 | 8/2016 | Lindsey et al. |
| 2016/0249940 A1 | 9/2016 | Stark |
| 2016/0287171 A1 | 10/2016 | Sand et al. |
| 2016/0287301 A1 | 10/2016 | Mehl et al. |
| 2016/0310188 A1 | 10/2016 | Marino et al. |
| 2016/0310197 A1 | 10/2016 | Black et al. |
| 2016/0324643 A1 | 11/2016 | Donner et al. |
| 2016/0324656 A1 | 11/2016 | Morris et al. |
| 2016/0374727 A1 | 12/2016 | Greenhalgh et al. |
| 2017/0014235 A1 | 1/2017 | Jones et al. |
| 2017/0020573 A1 | 1/2017 | Cain et al. |
| 2017/0020585 A1 | 1/2017 | Harshman et al. |
| 2017/0049488 A1 | 2/2017 | Vestgaarden |
| 2017/0086885 A1 | 3/2017 | Duncan et al. |
| 2017/0128083 A1 | 5/2017 | Germain |
| 2017/0128214 A1 | 5/2017 | Mayer |
| 2017/0135733 A1 | 5/2017 | Donner et al. |
| 2017/0135737 A1 | 5/2017 | Krause |
| 2017/0143513 A1 | 5/2017 | Sandstrom et al. |
| 2017/0156879 A1 | 6/2017 | Janowski |
| 2017/0156880 A1 | 6/2017 | Halverson et al. |
| 2017/0202511 A1 | 7/2017 | Chang et al. |
| 2017/0209155 A1 | 7/2017 | Petersen |
| 2017/0216036 A1 | 8/2017 | Cordaro |
| 2017/0224393 A1 | 8/2017 | Lavigne et al. |
| 2017/0246000 A1 | 8/2017 | Pavlov et al. |
| 2017/0258498 A1 | 9/2017 | Redmond et al. |
| 2017/0258506 A1 | 9/2017 | Redmond et al. |
| 2017/0258606 A1 | 9/2017 | Afzal |
| 2017/0266007 A1 | 9/2017 | Gelaude et al. |
| 2017/0296344 A1 | 10/2017 | Souza et al. |
| 2017/0303938 A1 | 10/2017 | Rindal et al. |
| 2017/0333205 A1 | 11/2017 | Joly et al. |
| 2017/0348034 A1 | 12/2017 | LaPierre et al. |
| 2017/0360570 A1 | 12/2017 | Berndt et al. |
| 2018/0008256 A1 | 1/2018 | Fallin et al. |
| 2018/0036041 A1 | 2/2018 | Pham et al. |
| 2018/0042652 A1 | 2/2018 | Mari et al. |
| 2018/0042735 A1 | 2/2018 | Schell et al. |
| 2018/0104063 A1 | 4/2018 | Asaad |
| 2018/0104068 A1 | 4/2018 | Sack |
| 2018/0110624 A1 | 4/2018 | Arnone |
| 2018/0110626 A1 | 4/2018 | McShane, III et al. |
| 2018/0200063 A1 | 7/2018 | Kahmer et al. |
| 2018/0214192 A1 | 8/2018 | Roby et al. |
| 2018/0228613 A1 | 8/2018 | Jones et al. |
| 2018/0228617 A1 | 8/2018 | Srour et al. |
| 2018/0228621 A1 | 8/2018 | Reiley et al. |
| 2018/0235643 A1 | 8/2018 | Lins et al. |
| 2018/0243097 A1 | 8/2018 | Jones et al. |
| 2018/0256232 A1 | 9/2018 | Russell |
| 2018/0256351 A1 | 9/2018 | Bishop et al. |
| 2018/0256352 A1 | 9/2018 | Nyahay et al. |
| 2018/0256361 A1 | 9/2018 | Bishop et al. |
| 2018/0280139 A1 | 10/2018 | Jones et al. |
| 2018/0280140 A1 | 10/2018 | Jones et al. |
| 2018/0289504 A1 | 10/2018 | Arthurs et al. |
| 2018/0296227 A1 | 10/2018 | Meek et al. |
| 2018/0296347 A1 | 10/2018 | Hamzey et al. |
| 2018/0296363 A1 | 10/2018 | Berry |
| 2018/0303520 A1 | 10/2018 | Rajpal |
| 2018/0303623 A1 | 10/2018 | Shoshtaev |
| 2018/0303624 A1 | 10/2018 | Shoshtaev |
| 2018/0317971 A1 | 11/2018 | Prevost |
| 2018/0360512 A1 | 12/2018 | Mari |
| 2018/0368894 A1 | 12/2018 | Wieland et al. |
| 2019/0000636 A1 | 1/2019 | Kim et al. |
| 2019/0008562 A1 | 1/2019 | Melton et al. |
| 2019/0046684 A1 | 2/2019 | Roth |
| 2019/0076258 A1 | 3/2019 | Black et al. |
| 2019/0076266 A1 | 3/2019 | Trudeau et al. |
| 2019/0083270 A1 | 3/2019 | Milz et al. |
| 2019/0091027 A1 | 3/2019 | Asaad et al. |
| 2019/0117827 A1 | 4/2019 | Roth |
| 2019/0125371 A1 | 5/2019 | Asfora et al. |
| 2019/0125408 A1 | 5/2019 | Asfora et al. |
| 2019/0133613 A1 | 5/2019 | Reiley et al. |
| 2019/0133769 A1 | 5/2019 | Tetsworth et al. |

(56) References Cited

U.S. PATENT DOCUMENTS

| | | |
|---|---|---|
| 2019/0133783 A1 | 5/2019 | Unger et al. |
| 2019/0142606 A1 | 5/2019 | Freudenberger |
| 2019/0150910 A1 | 5/2019 | Jones et al. |
| 2019/0151113 A1 | 5/2019 | Sack |
| 2019/0151114 A1 | 5/2019 | Sack |
| 2019/0159901 A1 | 5/2019 | Mauldin et al. |
| 2019/0183653 A1 | 6/2019 | Gregersen et al. |
| 2019/0231554 A1 | 8/2019 | Bishop et al. |
| 2019/0239935 A1 | 8/2019 | Willis et al. |
| 2019/0247094 A1 | 8/2019 | Yacoub et al. |
| 2019/0254840 A1 | 8/2019 | Gray et al. |
| 2019/0262048 A1 | 8/2019 | Sutika |
| 2019/0262049 A1 | 8/2019 | Tempco et al. |
| 2019/0290441 A1 | 9/2019 | Tong et al. |
| 2019/0298528 A1 | 10/2019 | Lindsey et al. |
| 2019/0298542 A1 | 10/2019 | Kloss |
| 2019/0328546 A1 | 10/2019 | Palagi et al. |
| 2019/0343564 A1 | 11/2019 | Tempco et al. |
| 2019/0343565 A1 | 11/2019 | Tempco et al. |
| 2019/0343566 A1 | 11/2019 | Tempco et al. |
| 2019/0343567 A1 | 11/2019 | Tempco et al. |
| 2019/0343640 A1 | 11/2019 | Donner et al. |
| 2019/0343641 A1 | 11/2019 | Mauldin et al. |
| 2019/0343644 A1 | 11/2019 | Ryan et al. |
| 2019/0343645 A1 | 11/2019 | Miccio et al. |
| 2019/0343652 A1 | 11/2019 | Petersheim et al. |
| 2019/0343653 A1 | 11/2019 | McKay |
| 2019/0388131 A1 | 12/2019 | Mehl et al. |
| 2019/0388228 A1 | 12/2019 | Donner et al. |
| 2019/0388242 A1 | 12/2019 | Harris et al. |
| 2020/0000595 A1 | 1/2020 | Jones et al. |
| 2020/0008817 A1 | 1/2020 | Reiley et al. |
| 2020/0008850 A1 | 1/2020 | Mauldin et al. |
| 2020/0022817 A1 | 1/2020 | Crossgrove et al. |
| 2020/0038069 A1 | 2/2020 | Jones et al. |
| 2020/0046512 A1 | 2/2020 | Newman et al. |
| 2020/0069431 A1 | 3/2020 | Boehm et al. |
| 2020/0100822 A1 | 4/2020 | Lipow |
| 2020/0129214 A1 | 4/2020 | Pepper et al. |
| 2020/0146721 A1 | 5/2020 | Sadiq |
| 2020/0149137 A1 | 5/2020 | Roth |
| 2020/0222195 A1 | 7/2020 | Assell et al. |
| 2020/0246158 A1 | 8/2020 | Bergey |
| 2020/0261240 A1 | 8/2020 | Mesiwala et al. |
| 2020/0268525 A1 | 8/2020 | Mesiwala et al. |
| 2020/0315647 A1 | 10/2020 | Fojtik et al. |
| 2020/0315666 A1 | 10/2020 | Nichols et al. |
| 2020/0315669 A1 | 10/2020 | Dejardin |
| 2020/0345507 A1 | 11/2020 | Reiley |
| 2020/0345508 A1 | 11/2020 | Reiley |
| 2020/0345509 A1 | 11/2020 | Reiley |
| 2020/0345510 A1 | 11/2020 | Reiley |
| 2020/0375750 A1 | 12/2020 | Abbasi et al. |
| 2020/0397491 A1 | 12/2020 | Frey et al. |
| 2021/0022882 A1 | 1/2021 | Dang et al. |
| 2021/0107093 A1 | 4/2021 | Tempco |
| 2021/0153911 A1 | 5/2021 | Stuart et al. |
| 2021/0169660 A1 | 6/2021 | Reckling et al. |
| 2021/0212734 A1 | 7/2021 | Mesiwala et al. |
| 2021/0228360 A1 | 7/2021 | Hunt et al. |
| 2021/0236146 A1 | 8/2021 | Donner et al. |
| 2021/0338454 A1 | 11/2021 | Afzal |
| 2021/0353337 A1 | 11/2021 | Kaufmann et al. |
| 2021/0393408 A1 | 12/2021 | Ginn |
| 2021/0393409 A1 | 12/2021 | Ginn |
| 2022/0031474 A1 | 2/2022 | Reckling et al. |
| 2022/0151668 A1 | 5/2022 | Mauldin et al. |
| 2022/0273446 A1 | 9/2022 | Stuart et al. |
| 2022/0273447 A1 | 9/2022 | Ginn |
| 2022/0273448 A1 | 9/2022 | Ginn et al. |
| 2022/0280303 A1 | 9/2022 | Mauldin et al. |
| 2022/0296377 A1 | 9/2022 | Ginn et al. |
| 2022/0296378 A1 | 9/2022 | Ginn |
| 2022/0304813 A1 | 9/2022 | Ginn et al. |
| 2022/0304814 A1 | 9/2022 | Ginn |

FOREIGN PATENT DOCUMENTS

| | | |
|---|---|---|
| CN | 1909848 A | 2/2007 |
| CN | 101795632 A | 8/2010 |
| CN | 102361601 A | 2/2012 |
| DE | 102011001264 A1 | 9/2012 |
| DE | 102012106336 A1 | 1/2014 |
| EP | 1287796 A1 | 3/2003 |
| EP | 2070481 B1 | 2/2012 |
| EP | 2796104 A1 | 10/2014 |
| EP | 2590576 B1 | 10/2015 |
| EP | 2749238 B1 | 3/2017 |
| EP | 2887899 B1 | 8/2017 |
| EP | 2341852 B1 | 8/2018 |
| EP | 2496162 B1 | 10/2018 |
| EP | 3484387 A1 | 5/2019 |
| EP | 3593745 A2 | 1/2020 |
| EP | 3616634 A1 | 3/2020 |
| EP | 3661441 A1 | 6/2020 |
| EP | 2408389 B1 | 4/2021 |
| JP | 59200642 A | 11/1984 |
| JP | 05-176942 A | 7/1993 |
| JP | 05184615 A | 7/1993 |
| JP | 09149906 A | 10/1997 |
| JP | 10-85231 A | 4/1998 |
| JP | 11318931 A | 11/1999 |
| JP | 2002509753 A | 4/2002 |
| JP | 2003511198 A | 3/2003 |
| JP | 2003533329 A | 11/2003 |
| JP | 2003534046 A | 11/2003 |
| JP | 2004121841 | 4/2004 |
| JP | 2004512895 | 4/2004 |
| JP | 2004516866 | 6/2004 |
| JP | 2006506181 | 2/2006 |
| JP | 2007535973 A | 12/2007 |
| JP | 2008540036 A | 11/2008 |
| JP | 2009521990 A | 6/2009 |
| JP | 2009533159 A | 9/2009 |
| JP | 2010137016 A | 6/2010 |
| JP | 2015150506 A | 4/2015 |
| WO | WO97/31517 A2 | 8/1997 |
| WO | WO01/17445 A1 | 3/2001 |
| WO | WO02/38054 | 5/2002 |
| WO | WO03/007839 A2 | 1/2003 |
| WO | WO04/02344 | 1/2004 |
| WO | WO2004/043277 A1 | 5/2004 |
| WO | WO2005/009729 A2 | 2/2005 |
| WO | WO2006/003316 | 1/2006 |
| WO | WO2006/023793 A2 | 3/2006 |
| WO | WO2006/074321 A2 | 7/2006 |
| WO | WO2006/116850 A1 | 11/2006 |
| WO | WO2009/025884 A2 | 2/2009 |
| WO | WO2009/029074 A1 | 3/2009 |
| WO | WO2010/105196 A1 | 9/2010 |
| WO | WO2011/010463 A1 | 1/2011 |
| WO | WO2011/110865 A2 | 9/2011 |
| WO | WO2011/124874 A1 | 10/2011 |
| WO | WO2011/149557 A1 | 12/2011 |
| WO | WO2012/015976 A1 | 2/2012 |
| WO | WO2012/048008 A1 | 4/2012 |
| WO | WO2013/000071 A1 | 1/2013 |
| WO | WO2013/052807 A2 | 4/2013 |
| WO | WO2013/119907 A1 | 8/2013 |
| WO | WO2014/145902 A1 | 9/2014 |
| WO | WO2017/147140 A1 | 8/2017 |
| WO | WO2017/147537 A1 | 8/2017 |

OTHER PUBLICATIONS

Stuart et al.; U.S. Appl. No. 17/812,945 entitled "Sacro-iliac joint stabilizing implants and methods of implantation," filed Jul. 15, 2022.

Mauldin et al.; U.S. Appl. No. 17/805,165 entitled "Systems, device, and methods for joint fusion," filed Jun. 2, 2022.

Mauldin et al.; U.S. Appl. No. 17/822,360 entitled "Fenestrated implant," filed Aug. 25, 2022.

Acumed: Acutrak Headless Compressioin Screw (product information); 12 pgs; © 2005; retrieved Sep. 25, 2014 from http://www.

(56) References Cited

OTHER PUBLICATIONS rcsed.ac.uk/fellows/Ivanrensburg/classification/surgtech/acumed/manuals/acutrak-brochure%200311.pdf.

Al-Khayer et al.; Percutaneous sacroiliac joint arthrodesis, a novel technique; J Spinal Disord Tech; vol. 21; No. 5; pp. 359-363; Jul. 2008.

Khurana et al.; Percutaneous fusion of the sacroiliac joint with hollow modular anchorage screws, clinical and radiological outcome; J Bone Joint Surg; vol. 91-B; No. 5; pp. 627-631; May 2009.

Lu et al.; Mechanical properties of porous materials; Journal of Porous Materials; 6(4); pp. 359-368; Nov. 1, 1999.

Peretz et al.; The internal bony architecture of the sacrum; Spine; 23(9); pp. 971-974; May 1, 1998.

Richards et al.; Bone density and cortical thickness in normal, osteopenic, and osteoporotic sacra; Journal of Osteoporosis; 2010(ID 504078); 5 pgs; Jun. 9, 2010.

Wise et al.; Minimally invasive sacroiliac arthrodesis, outcomes of a new technique; J Spinal Disord Tech; vol. 21; No. 8; pp. 579-584; Dec. 2008.

Schneider et al.; U.S. Appl. No. 17/443,388 entitled "Matrix implant," filed Jul. 26, 2021.

Lindsey et al.; U.S. Appl. No. 18/066,872 entitled "Threaded implants and methods of use across bone segments," filed Dec. 15, 2022.

Mesiwala et al.; U.S. Appl. No. 17/649,265 entitled "Implants for spinal fixation and or fusion," filed Jan. 28, 2022.

Mesiwala et al.; U.S. Appl. No. 17/649,296 entitled "Implants for spinal fixation and or fusion," filed Jan. 28, 2022.

Mauldin et al.; U.S. Appl. No. 17/650,473 entitled "Fenestrated implant," filed Feb. 9, 2022.

\* cited by examiner

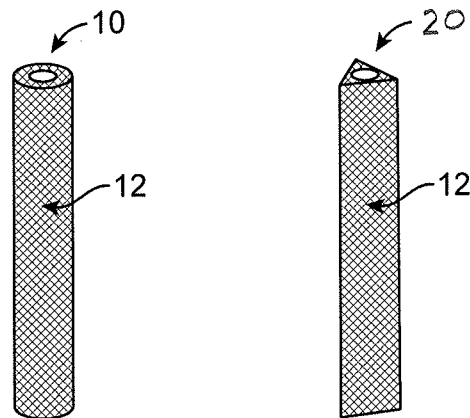
FIG. 3
(PRIOR ART)
FIG. 4
(PRIOR ART)
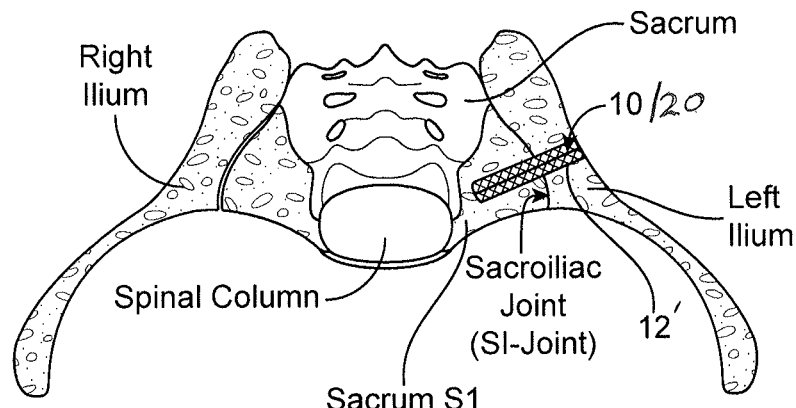
FIG. 5
(PRIOR ART)
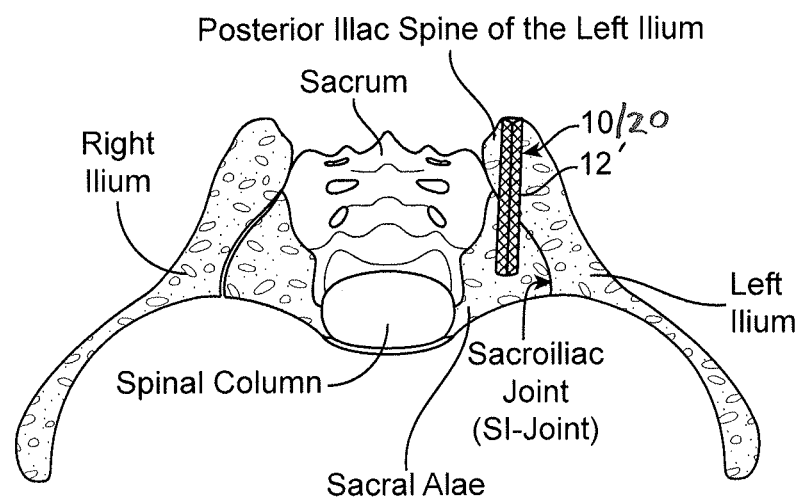
FIG. 6
(PRIOR ART)

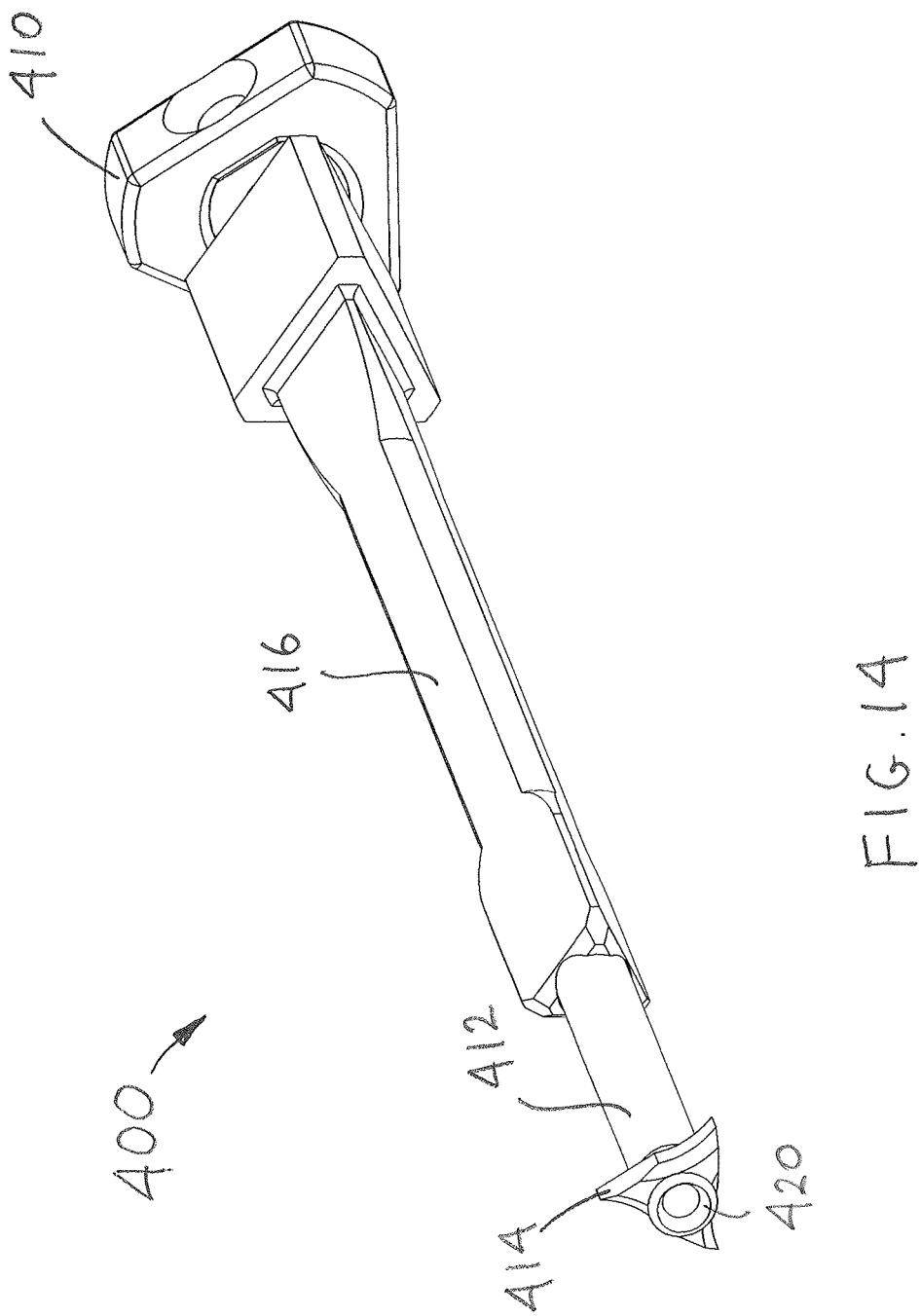

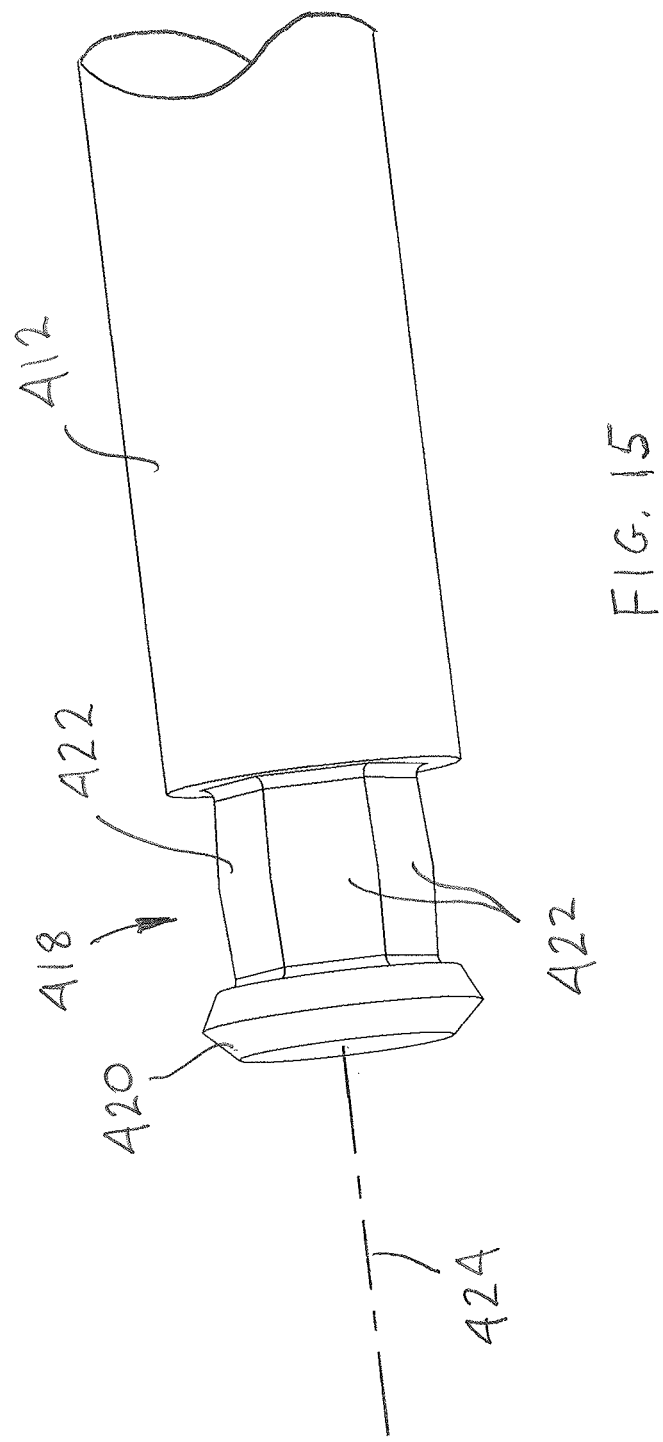

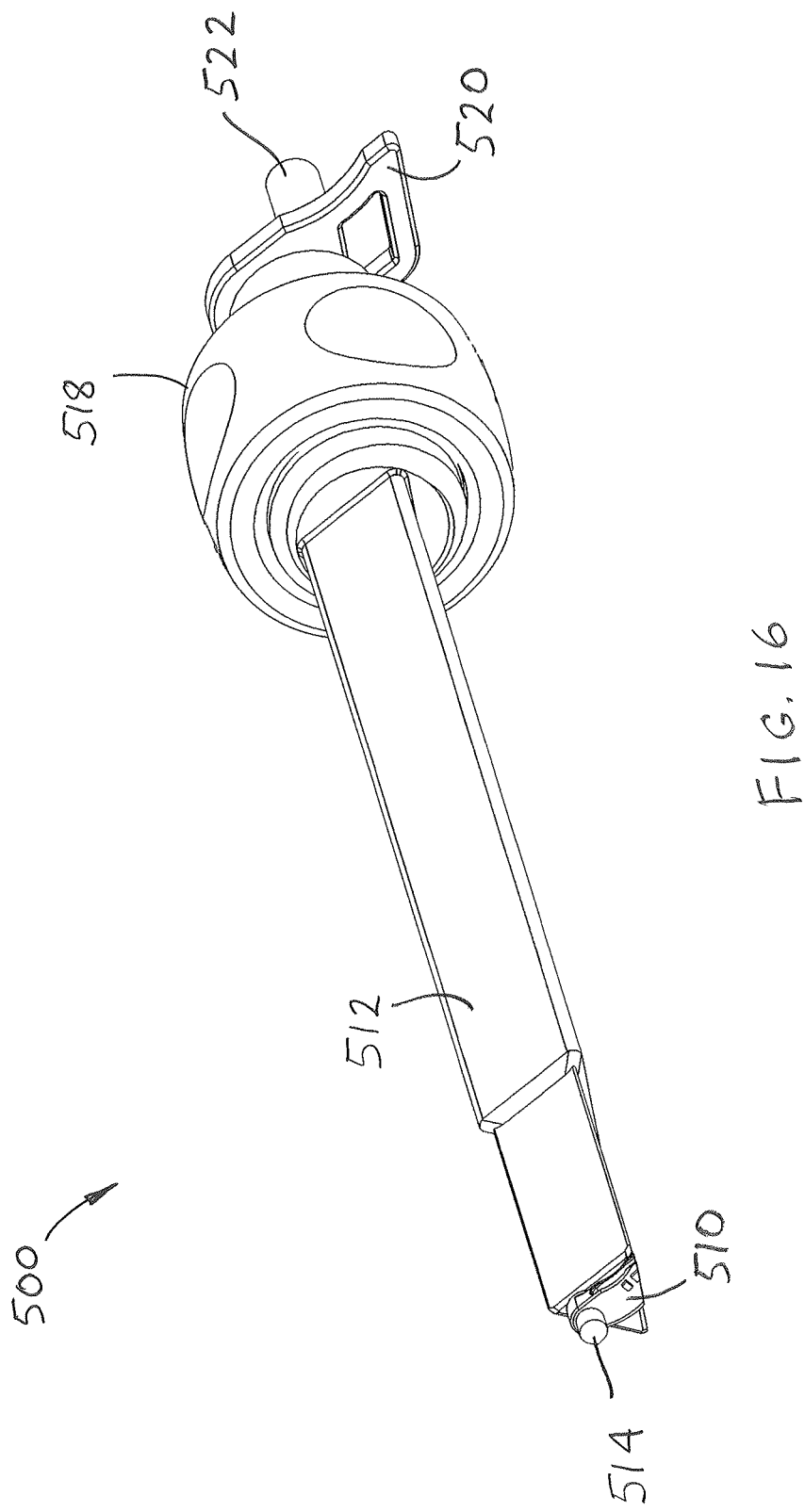

SYSTEMS AND METHODS FOR DECORTICATING THE SACROILIAC JOINT

CROSS REFERENCE TO RELATED APPLICATIONS

This application is a continuation of U.S. application Ser. No. 16/143,061, filed Sep. 26, 2018, which claims the benefit of U.S. Provisional Application No. 62/563,271, filed Sep. 26, 2017, each of which is herein incorporated by reference in its entirety.

INCORPORATION BY REFERENCE

All publications and patent applications mentioned in this specification are herein incorporated by reference for all intents and purposes to the same extent as if each individual publication or patent application was specifically and individually indicated to be incorporated by reference.

FIELD

Embodiments of the disclosure relate generally to fixation or fusion of a bone joint, and more specifically, to decorticating a joint in preparation for joint fixation or fusion.

BACKGROUND

Sacroiliac joint (SI-Joint) fusion is a surgical procedure that is performed to alleviate pain coming from the SI-Joint in patients who have failed to receive adequate pain relief with non-surgical treatments of the SI-Joint. Some conditions of the SI-Joint that may be treated with SI-Joint fusion (arthrodesis) are: degenerative sacroiliitis, inflammatory sacroiliitis, iatrogenic instability of the sacroiliac joint, osteitis condensans ilii, or traumatic fracture dislocation of the pelvis. Historically, screws and screws with plates were used as the standard instrumentation for sacro-iliac fusion. An SI-Joint fusion consisted of an open surgical approach to the SI-Joint from an anterior, a posterior, or a lateral direction. The surgeon would then debride (remove) the cartilage from the articular portion of the joint and the interosseous ligament from the fibrous portion of the joint. These open approaches require a large incision and deep soft tissue dissection to approach the damaged, subluxed, dislocated, fractured, or degenerative SI-Joint.

With more recent advancements in SI-Joint surgery, a typical technique for placing implants involves placement of one or multiple implants from a lateral to medial direction across the SI-Joint. These implants are placed with a starting point on the lateral aspect of the ilium. The implants are then directed across the ilium, across the sacroiliac joint and into the sacrum.

No debridement or decortication of the articular surfaces of the SI-Joint is done in many SI-Joint fusion procedures performed today. However, some surgeons believe that decortication of the joint would promote faster and stronger fusion of the joint.

Accordingly, it would be desirable to provide systems and methods for decorticating portions of the SI-Joint in a minimally invasive fashion during SI-Joint fusion surgery.

SUMMARY

According to aspects of the disclosure, systems and methods for decorticating at least one bone surface are provided. In some embodiments, the systems include an elongated soft tissue protector, an elongated drive shaft and a cutter. The elongated soft tissue protector has a bore extending therethrough. The bore has a non-circular lateral cross-section, a maximum lateral extent and a minimum lateral extent. The elongated drive shaft has a proximal and a distal end. The cutter may be located on or near the distal end of the drive shaft. The cutter has a non-circular lateral cross-section, a maximum lateral extent and a minimum lateral extent. The maximum lateral extent of the cutter is greater than the minimum lateral extent of the bore but is no greater than the maximum lateral extent of the bore. The bore of the soft tissue protector is configured to slidably receive the cutter therethrough. The minimum lateral extent of the bore prevents the maximum lateral extent of the cutter from rotating when inside the bore but allows the drive shaft to rotate when the cutter is extended from a distal end of the bore.

In some embodiments, the bore of the soft tissue protector has a rectilinear lateral cross-sectional profile. The rectilinear lateral cross-sectional profile may be generally triangular in shape. The system may further include a body that is provided with a cylindrical bore therethrough, wherein the cylindrical bore is configured to slidably and rotatably receive the drive shaft. The body may be configured to be slidably received within the bore of soft tissue protector. In some embodiments, the drive shaft and cutter are provided with a longitudinal bore sized to slide over a guide pin.

In some embodiments, the proximal end of the drive shaft is provided with a handle configured to allow the drive shaft to be manually rotated and moved longitudinally relative to the soft tissue protector. The proximal end of the drive shaft may be provided with an indexing feature configured to show a rotational orientation of the drive shaft and the cutter relative to the soft tissue protector so that the cutter can be aligned with and retracted into the soft tissue protector. In some embodiments, the system includes a navigation array mounted near the proximal end of the drive shaft. The array includes a plurality of emitters or reflectors located at predetermined and unique distances from one another to generate a signal to aid in navigation of the cutter with regard to a reference frame associated with a patient on an imaging system.

In some embodiments, a method of decorticating at least one bone surface includes the steps of forming an implant bore across a first bone into a space between the first bone and an adjacent second bone, inserting a cutter of a decorticating device through the implant bore, and rotating the cutter. In this embodiment, the implant bore has a non-circular lateral cross-section, a maximum lateral extent and a minimum lateral extent. The cutter has a non-circular lateral cross-section, a maximum lateral extent and a minimum lateral extent. The maximum lateral extent of the cutter is greater than the minimum lateral extent of the implant bore but no greater than the maximum lateral extent of the implant bore. In the cutter rotating step, the maximum lateral extent of the cutter extends laterally beyond the implant bore and decorticates a surface of at least one of the first and second bones.

In some embodiments of the above methods, the first bone is an ilium and the second bone is a sacrum. The method may further include withdrawing the cutter from the implant bore and placing an implant into the implant bore. In some embodiments, the implant bore has a rectilinear lateral cross-sectional profile. The rectilinear lateral cross-sectional profile may be generally triangular in shape. In some embodiments, the method further includes inserting a guide pin across the first bone and into the second bone, and sliding the cutter of the decortication device over the guide pin.

In some embodiments, the decorticating device further comprises a handle and a drive shaft interconnecting the handle to the cutter. The method may further include manually manipulating the handle to rotate the cutter and to move the cutter longitudinally relative to the implant bore. The handle or a proximal end of the drive shaft may be provided with an indexing feature configured to show a rotational orientation of the drive shaft and the cutter relative to the implant bore. In some embodiments, the method further includes manipulating the handle to align the cutter with and retract the cutter through the non-circular implant bore.

In some embodiments, systems for decorticating at least one bone surface include an elongated drive shaft, an elongated body and a non-symmetrical offset cutter. The elongated body has a central longitudinal axis and a bore extending therethrough. The bore is parallel to and laterally offset from the central longitudinal axis and is configured to slidably and rotatably receive the drive shaft therethrough. The non-symmetrical offset cutter is located on or near a distal end of the drive shaft. The cutter has a profile that fits within a lateral cross-section of the elongated body in at least one orientation and extends laterally outside of the cross-section when the drive shaft and cutter are rotated.

In some embodiments of the above systems, the lateral cross-section of the elongated body has a rectilinear profile. The rectilinear profile may be generally triangular in shape. In some embodiments, the system further includes a navigation array mounted near a proximal end of the drive shaft. The array includes a plurality of emitters or reflectors located at predetermined and unique distances from one another to generate a signal to aid in navigation of the cutter with regard to a reference frame associated with a patient on an imaging system.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying drawings of which:

FIGS. 3 and 4 are embodiments of various implants that can be used for the fusion or fixation of a joint or two bone segments.

FIG. 5 illustrates an axial section view of the SI-Joint with an implant for the fixation of the SI-Joint using a lateral approach that goes laterally through the ilium, the SI-Joint, and into the sacrum S1.

FIG. 6 illustrates an axial section view of the SI-Joint with an implant for the fixation of the SI-Joint using a posterolateral approach entering from the posterior iliac spine of the ilium, angling through the SI-Joint, and terminating in the sacral alae.

FIG. 14 is a perspective view showing another exemplary embodiment of a decorticating system.

FIG. 15 is an enlarged perspective view showing the distal end of the system of FIG. 14.

FIG. 16 is a perspective view showing another exemplary embodiment of a decorticating system.

DETAILED DESCRIPTION

A joint of a patient can be decorticated or selectively decorticated in order to promote bone regeneration and fusion at the implant site. Many types of hardware are available both for the fixation of bones that are fractured and for the fixation of bones that are to be fused (arthrodesed). While the following examples focus on the SI-Joint, the methods, instrumentation and implants disclosed herein may be used for decortication of other body joints as well.

Figure 1:
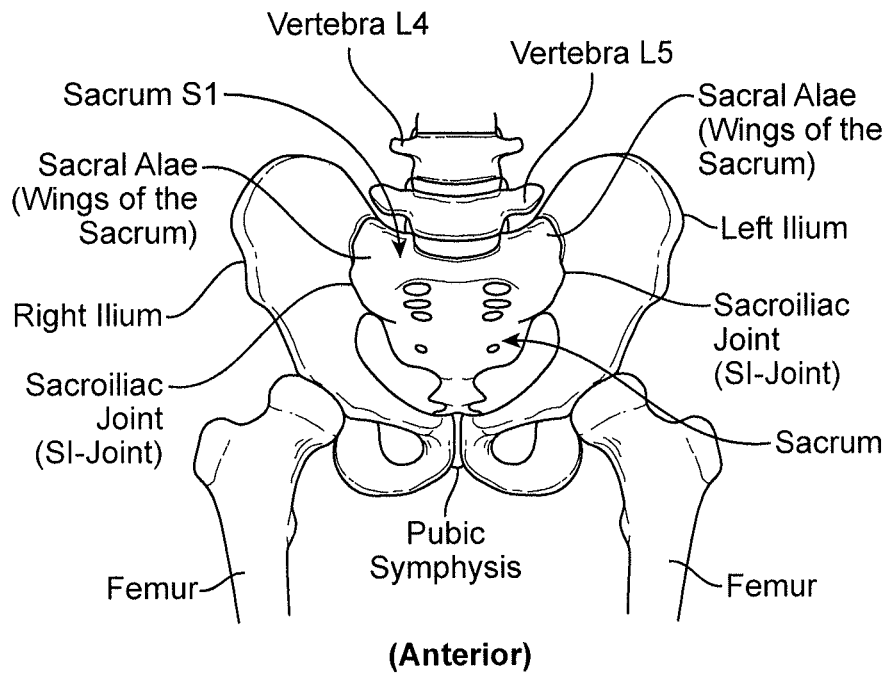
FIGS. 1 and 2 are, respectively, anterior and posterior anatomic views of the human hip girdle comprising the sacrum and the hip bones (the right ilium, and the left ilium), the sacrum being connected with both hip bones at the sacroiliac joint (in shorthand, the SI-Joint).
Figure 2:
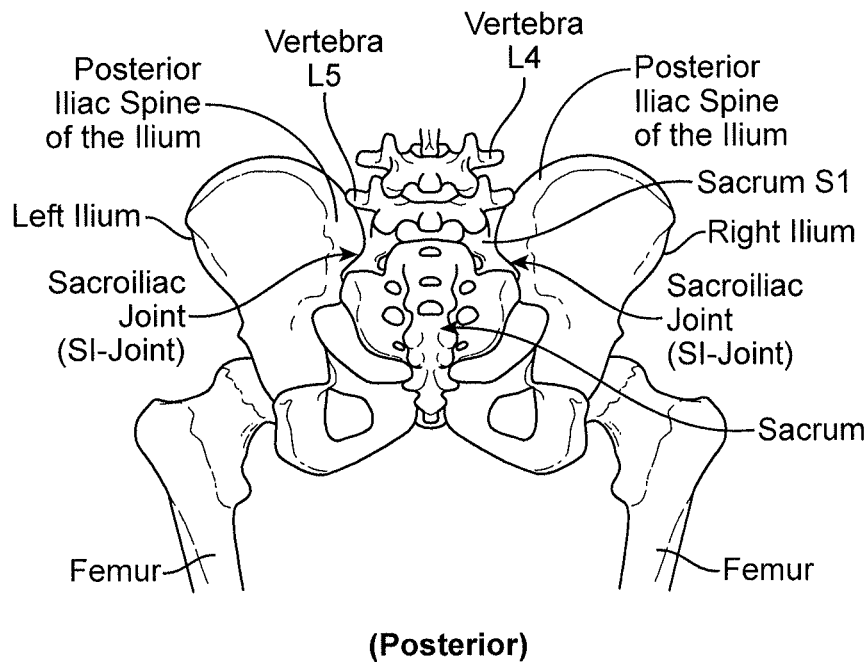

Referring to FIGS. 1 and 2, the human hip girdle is made up of three large bones joined by three relatively immobile joints. One of the bones is called the sacrum and it lies at the bottom of the lumbar spine, where it connects with the L5 vertebra. The other two bones are commonly called "hip bones" and are technically referred to as the right ilium and-the left ilium. The sacrum connects with both hip bones at the sacroiliac joint (in shorthand, the SI-Joint).

The SI-Joint functions in the transmission of forces from the spine to the lower extremities, and vice-versa. The SI-Joint has been described as a pain generator for up to 22% of lower back pain patients.

To relieve pain generated from the SI-Joint, sacroiliac joint fusion is typically indicated as surgical treatment, e.g., for degenerative sacroiliitis, inflammatory sacroiliitis, iatrogenic instability of the sacroiliac joint, osteitis condensans ilii, or traumatic fracture dislocation of the pelvis. In some currently performed procedures, screws or screws with plates are used for sacro-iliac fusion. At the time of the procedure, articular cartilage may be removed from the "synovial joint" portion of the SI-Joint. This can require a large incision to approach the damaged, subluxed, dislocated, fractured, or degenerated joint. The large incision and removal of tissue can cause significant trauma to the patient, resulting in pain and increasing the time to heal after surgery.

In addition, screw type implants tend to be susceptible to rotation and loosening, especially in joints that are subjected to torsional forces, such as the SI-Joint. Excessive movement of the implant after implantation may result in the failure of the implant to incorporate and fuse with the bone, which may result in the need to remove and replace the failed implant.

FIG. 3 and FIG. 4 illustrate straight implants 10 and 20, respectively, with a solid elongate body 12 or 12' that can be used for the fixation or fusion of two bone segments. The implant 10 shown in FIG. 3 is cylindrical and can optionally have screw threads along the exterior of the implant body. As mentioned above, cylindrical screw type implants can suffer from excessive rotation. One solution to this problem is the implant 20 in FIG. 4, which has a non-cylindrical cross-sectional area. For example, as shown, the implant 20 can have a triangular cross-sectional area, although other rectilinear cross-sectional profiles may be used as well, including rectangular, hexagonal and the like. Non-cylindrical implants need not have a strict rectilinear cross-sectional profile in order to resist rotation. A cross-sectional area that is non-circular will generally suffice. For example, a tear drop shaped cross-sectional area, or a cross-sectional area with at least one apex, can resist rotation. Other non-circular cross-sectional geometries that may not have a rectilinear component can also work, such as oval cross-sections.

FIG. 5 illustrates insertion of the implant 10 or 20 of FIG. 3 or FIG. 4 across the SI-Joint using a lateral approach that goes laterally through the ilium, across the SI-Joint, and into the sacrum. FIG. 6 illustrates insertion of the same implant across the SI-Joint using a postero-lateral approach entering from the posterior iliac spine of the ilium, angling through the SI-Joint, and terminating in the sacral alae. The implants and instrumentation described herein typically can be inserted across the SI-Joint according to one of these two approaches, or with a similar approach.

Referring to FIGS. 7-10, an exemplary method for fixation of the SI-Joint will be described. Elongated, stem-like implant structures 10 or 20 like those shown in FIGS. 3 and 4 make possible the fixation of the SI-Joint in a minimally invasive manner. These implant structures can be effectively implanted through the use a lateral surgical approach (as shown in FIG. 5). The procedure may be aided by conventional lateral, inlet, and outlet visualization techniques, e.g., using X-ray image intensifiers such as a C-arms or fluoroscopes to produce a live image feed, which is displayed on a TV screen.

Figure 9:
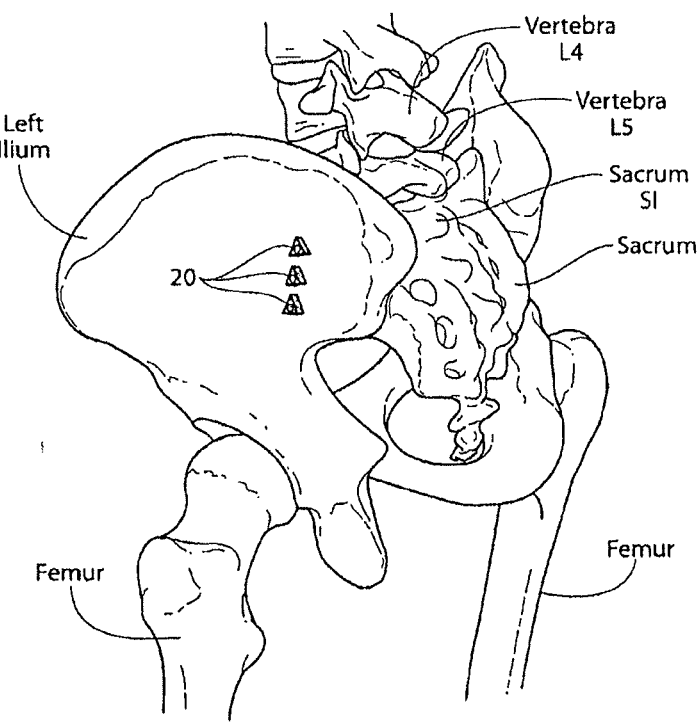
Figure 10:
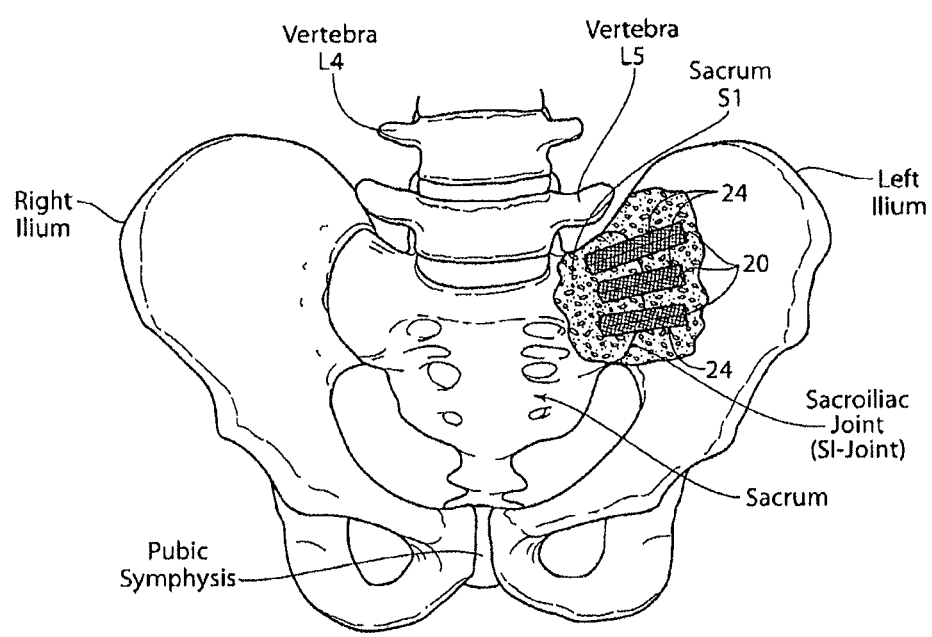

In this exemplary embodiment, one or more implant structures 20 are introduced laterally through the ilium, the SI-Joint, and into the sacrum. This path and resulting placement of the implant structure(s) 20 are best shown in FIGS. 9 and 10. In the illustrated embodiment, three implant structures 20 are placed in this manner. Also in the illustrated embodiment, the implant structures 20 are rectilinear in cross section and triangular in this case, but it should be appreciated that implant structures 20 of other rectilinear cross sections can be used. Additionally, in some procedures (not discussed in further detail herein), implants may be introduced into the SI-Joint from an anterior direction. Further information on anterior techniques may be found in co-pending U.S. patent application Pub. No. 2015/0105828 filed Oct. 15, 2014 and entitled "Implant Placement". The decortication instruments and methods disclosed herein and variants thereof may also be utilized in these anterior procedures.

Before undertaking a lateral implantation procedure, the physician diagnoses the SI-Joint segments that are to be fixated or fused (arthrodesed) using, e.g., the Fortin finger test, thigh thrust, FABER, Gaenslen's, compression, distraction, and or diagnostic SI-Joint injection.

Aided by lateral, inlet, and outlet C-arm views, and with the patient lying in a prone position, the physician aligns the greater sciatic notches and then the alae (using lateral visualization) to provide a true lateral position. A 3 cm incision is made starting aligned with the posterior cortex of the sacral canal, followed by blunt tissue separation to the ilium. From the lateral view, the guide pin 38 (with pin sleeve (not shown)) (e.g., a Steinmann Pin) is started resting on the ilium at a position inferior to the sacrum end plate and just anterior to the sacral canal. In the outlet view, the guide pin 38 should be parallel to the sacrum end plate at a shallow angle anterior (e.g., 15 degree to 20 degree off the floor, as FIG. 10 shows). In a lateral view, the guide pin 38 should be posterior to the sacrum anterior wall. In the outlet view, the guide pin 38 should be superior to the first sacral foramen and lateral of mid-line. This corresponds generally to the sequence shown diagrammatically in FIGS. 7A and 7B. A soft tissue protector (not shown), and a drill sleeve (not shown) within the soft tissue protector, may be slipped over the guide pin 38 and firmly against the ilium before removing the guide pin sleeve (not shown).

Figure 7A:
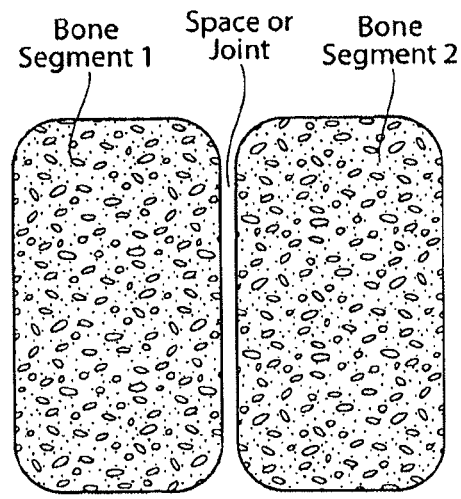
FIGS. 7A-7D are side section views of the formation of a broached bore in bone according to one embodiment of the disclosure.
Figure 7B:
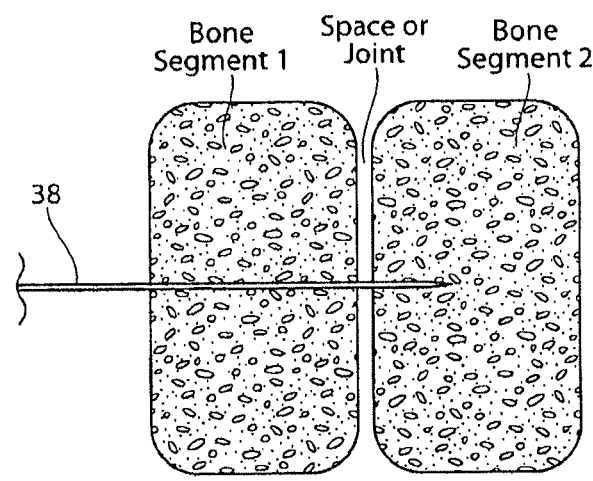
Figure 7C:
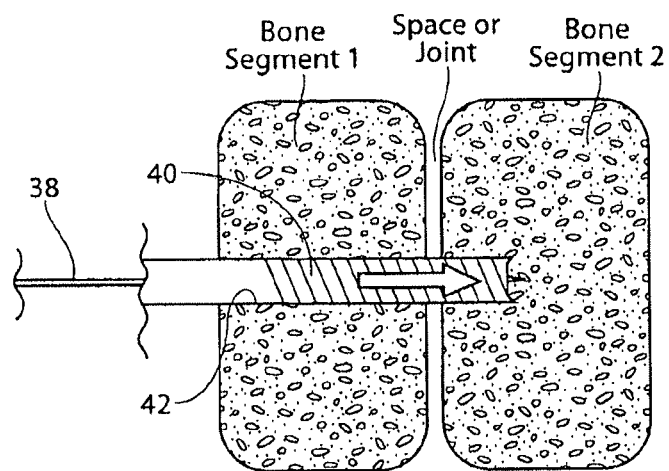

Over the guide pin 38 (and through the soft tissue protector and drill sleeve), a pilot bore 42 may be drilled with cannulated drill bit 40, as is diagrammatically shown in FIG. 7C. The pilot bore 42 may extend through the ilium, through the SI-Joint, and into the sacrum. The drill bit 40 and drill sleeve (not shown) are then removed.

A shaped broach 44 may be tapped into the pilot bore 42 over the guide pin 38 (and through the soft tissue protector, not shown) to create a broached bore 48 with the desired profile for the implant structure 20, which, in the illustrated embodiment, is triangular. This generally corresponds to the sequence shown diagrammatically in FIG. 7D. The triangular profile of the broached bore 48 is also shown in FIG. 8.

Figure 7D:
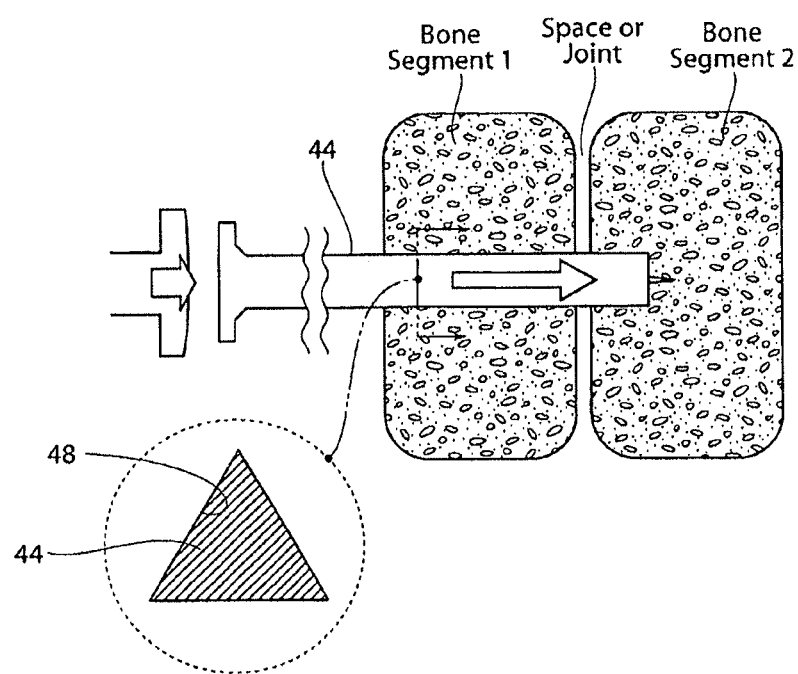
Figure 7E:
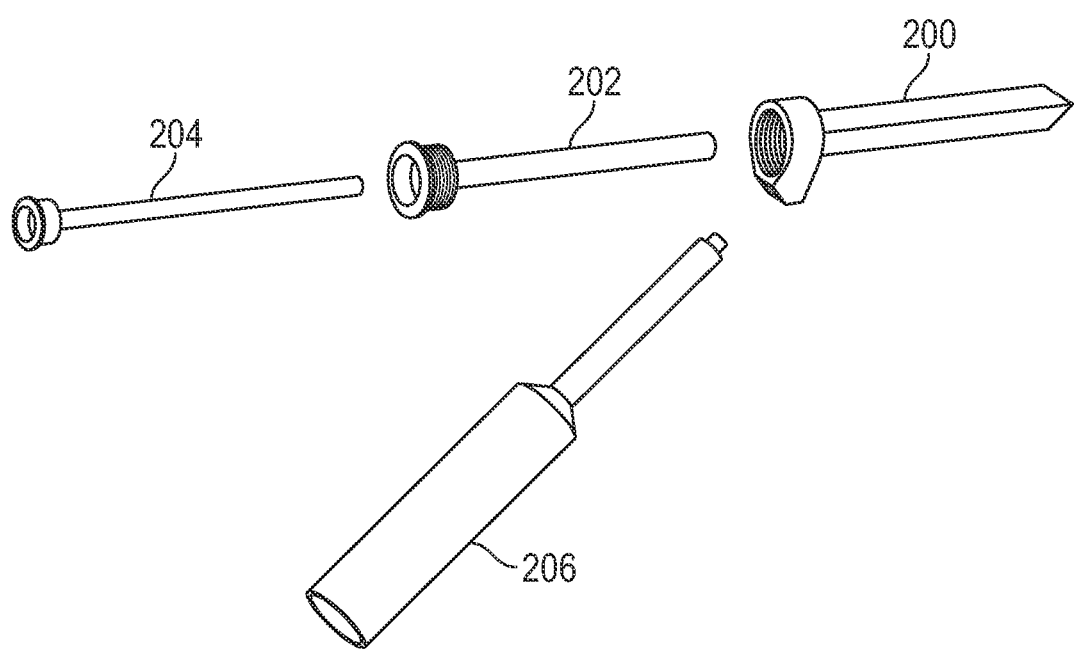
FIGS. 7E and 7F illustrate the assembly of a soft tissue protector system for placement over a guide wire.
Figure 7F:
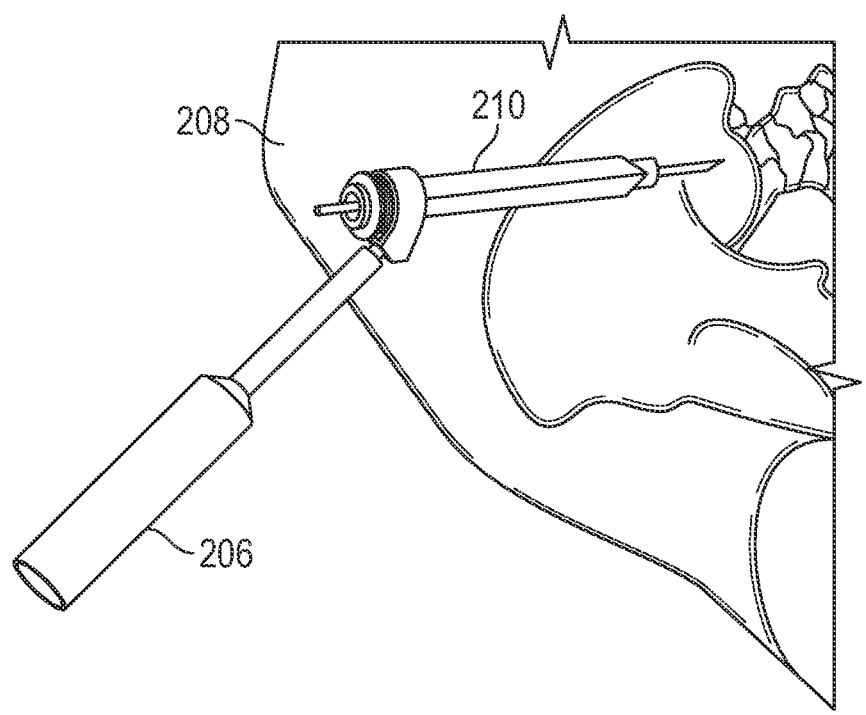

FIGS. 7E and 7F illustrate an embodiment of the assembly of a soft tissue protector or dilator or delivery sleeve 200 with a drill sleeve 202, a guide pin sleeve 204 and a handle 206. In some embodiments, the drill sleeve 202 and guide pin sleeve 204 can be inserted within the soft tissue protector 200 to form a soft tissue protector assembly 210 that can slide over the guide pin 208 until bony contact is achieved. The soft tissue protector 200 can be any one of the soft tissue protectors or dilators or delivery sleeves disclosed herein. In some embodiments, an expandable dilator or delivery sleeve 200 can be used in place of a conventional soft tissue dilator. In the case of the expandable dilator, in some embodiments, the expandable dilator can be slid over the guide pin and then expanded before the drill sleeve 202 and/or guide pin sleeve 204 are inserted within the expandable dilator. In other embodiments, insertion of the drill sleeve 202 and/or guide pin sleeve 204 within the expandable dilator can be used to expand the expandable dilator.

In some embodiments, a dilator can be used to open a channel though the tissue prior to sliding the soft tissue protector assembly 210 over the guide pin. The dilator(s) can be placed over the guide pin, using for example a plurality of sequentially larger dilators or using an expandable dilator. After the channel has been formed through the tissue, the dilator(s) can be removed and the soft tissue protector assembly can be slid over the guide pin. In some embodiments, the expandable dilator can serve as a soft tissue protector after being expanded. For example, after expansion the drill sleeve and guide pin sleeve can be inserted into the expandable dilator.

Figure 8:
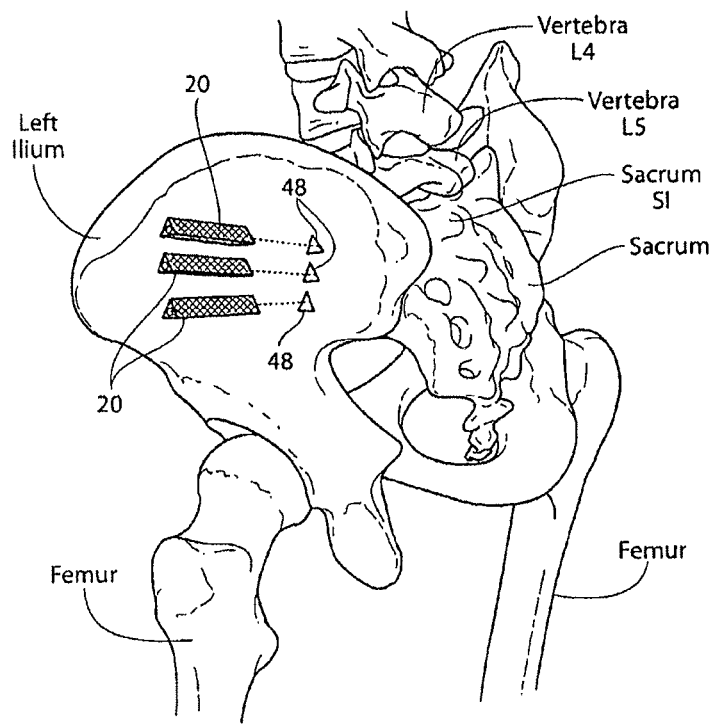
FIGS. 8 to 10 are anatomic views showing, respectively, a pre-implanted perspective, implanted perspective, and implanted anterior view, the implantation of three implant structures for the fixation of the SI-Joint using a lateral approach through the ilium, the SI-Joint, and into the sacrum.

As shown in FIGS. 8 and 9, a triangular implant structure 20 can be now tapped through the soft tissue protector over the guide pin 38 through the ilium, across the SI-Joint, and into the sacrum, until the proximal end of the implant structure 20 is flush against the lateral wall of the ilium (see also FIGS. 5 and 10). The guide pin 38 and soft tissue protector are withdrawn, leaving the implant structure 20 residing in the broached passageway, flush with the lateral wall of the ilium (see FIGS. 5 and 10). In the illustrated embodiment, two additional implant structures 20 are implanted in this manner, as FIG. 9 best shows. In other embodiments, the proximal ends of the implant structures 20 are left proud of the lateral wall of the ilium, such that they extend 1, 2, 3 or 4 mm outside of the ilium. This ensures that the implants 20 engage the hard cortical portion of the ilium rather than just the softer cancellous portion, through which they might migrate if there was no structural support from hard cortical bone. The hard cortical bone can also bear the loads or forces typically exerted on the bone by the implant 20.

The implant structures 20 are sized according to the local anatomy. For the SI-Joint, representative implant structures 20 can range in size, depending upon the local anatomy, from about 35 mm to about 60 mm in length, and about a 7 mm inscribed diameter (i.e. a triangle having a height of about 10.5 mm and a base of about 12 mm). The morphology of the local structures can be generally understood by medical professionals using textbooks of human skeletal anatomy along with their knowledge of the site and its disease or injury. The physician is also able to ascertain the dimensions of the implant structure 20 based upon prior analysis of the morphology of the targeted bone using, for example, plain film x-ray, fluoroscopic x-ray, or MM or CT scanning.

Using a lateral approach, one or more implant structures 20 can be individually inserted in a minimally invasive fashion across the SI-Joint, as has been described. Conventional tissue access tools, obturators, cannulas, and/or drills can be used for this purpose. Alternatively, the novel tissue access tools described above and in U.S. Provisional Patent Application No. 61/609,043, titled "TISSUE DILATOR AND PROTECTOR" and filed Mar. 9, 2012, and in U.S. Published Application No. 2017/0007409, titled "SYSTEMS, DEVICES, AND METHODS FOR JOINT FUSION" and filed Jul. 12, 2016, can also be used. No joint preparation, removal of cartilage, or scraping are required before formation of the insertion path or insertion of the implant structures 20, so a minimally invasive insertion path sized approximately at or about the maximum outer diameter of the implant structures 20 can be formed.

The implant structures 20 can obviate the need for autologous bone graft material, additional pedicle screws and/or rods, hollow modular anchorage screws, cannulated compression screws, threaded cages within the joint, or fracture fixation screws. Still, in the physician's discretion, bone graft material and other fixation instrumentation can be used in combination with the implant structures 20.

In a representative procedure, one to six, or perhaps up to eight, implant structures 20 can be used, depending on the size of the patient and the size of the implant structures 20. After installation, the patient would be advised to prevent or reduce loading of the SI-Joint while fusion occurs. This could be about a six to twelve week period or more, depending on the health of the patient and his or her adherence to post-op protocol.

The implant structures 20 make possible surgical techniques that are less invasive than traditional open surgery with no extensive soft tissue stripping. The lateral approach to the SI-Joint provides a straightforward surgical approach that complements the minimally invasive surgical techniques. The profile and design of the implant structures 20 minimize or reduce rotation and micromotion. Rigid implant structures 20 made from titanium provide immediate post-op SI-Joint stability. A bony in-growth region 24 comprising a porous plasma spray coating with irregular surface supports stable bone fixation/fusion. The implant structures 20 and surgical approaches make possible the placement of larger fusion surface areas designed to maximize post-surgical weight bearing capacity and provide a biomechanically rigorous implant designed specifically to stabilize the heavily loaded SI-Joint. In some embodiments, a fenestrated matrix implant may be used, providing cavities in which to pack bone growth material, and or providing additional surface area for bone on-growth, in-growth and or through-growth.

To improve the stability and weight bearing capacity of the implant, the implant can be inserted across three or more cortical walls. For example, after insertion the implant can traverse two cortical walls of the ilium and at least one cortical wall of the sacrum. The cortical bone is much denser and stronger than cancellous bone and can better withstand the large stresses found in the SI-Joint. By crossing three or more cortical walls, the implant can spread the load across more load bearing structures, thereby reducing the amount of load borne by each structure. In addition, movement of the implant within the bone after implantation is reduced by providing structural support in three locations around the implant versus two locations.

Further details of bone joint implants and methods of use can be found in U.S. Pat. No. 8,308,779 entitled "SYSTEMS AND METHODS FOR THE FIXATION OR FUSION OF BONE" filed Feb. 25, 2008, U.S. Pat. No. 7,922,765 entitled "SYSTEMS AND METHODS FOR THE FIXATION OR FUSION OF BONE" filed Mar. 24, 2005, U.S. Pat. No. 8,986,348 entitled "SYSTEMS AND METHODS FOR THE FUSION OF THE SACRAL-ILIAC JOINT" filed Oct. 5, 2010, and U.S. Pat. No. 8,414,648 entitled "APPARATUS, SYSTEMS, AND METHODS FOR ACHIEVING TRANS-ILIAC LUMBAR FUSION" filed Dec. 6, 2010

In the previously described methods, the implant(s) 10 or 20 (FIGS. 3 and 4) may be placed in the implant bore(s) 48 (FIG. 8) with no additional preparation of the SI-Joint. In other embodiments, according to aspects of the present disclosure, all or portions of the articulating surfaces of the SI-Joint may be decorticated, typically prior to placing the implant(s), as will now be described.

Figure 11A:
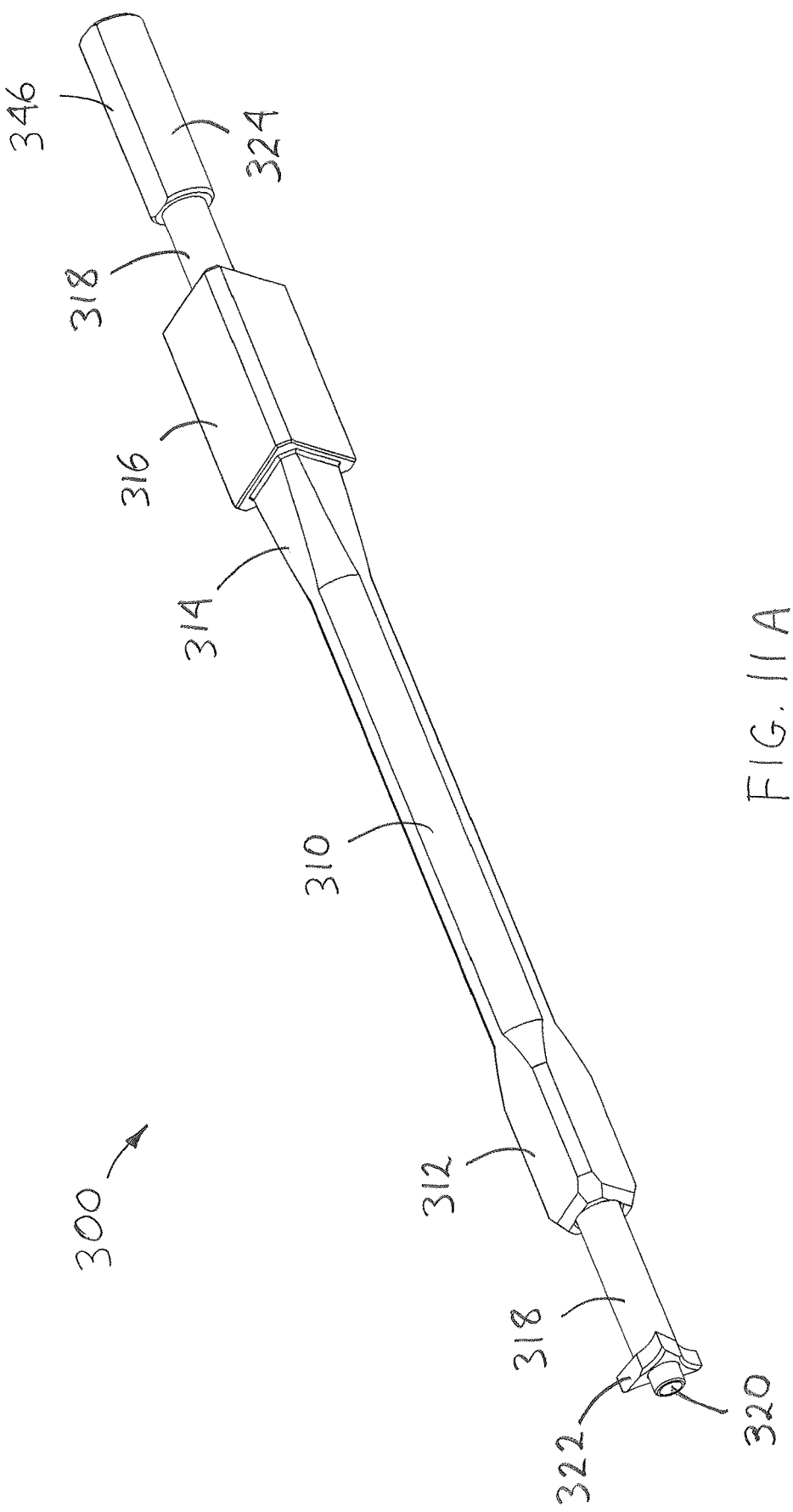
FIG. 11A is a perspective view showing an exemplary embodiment of a decorticating system constructed according to aspects of the present disclosure.

Referring to FIG. 11A, an exemplary embodiment of a decorticating system and method is shown. Cutting instrument 300 is provided with a main body 310 which has triangular portions 312 and 314 at its distal and proximal ends, respectively. Triangular portions 312 and 314 are configured to be slidably received within the triangular bore of the soft tissue protector 200 shown in FIG. 7E and prevent body 310 from rotating within soft tissue protector 200. A stop 316 may be located proximal to the proximal triangular portion 314. Stop 316 is configured to abut against the proximal end of soft tissue protector 200 to limit the distal travel of body 310 into soft tissue protector 200.

Body 310 is provided with a cylindrical bore therethrough along its longitudinal axis for slidably and rotatably receiving drive shaft 318. Drive shaft 318 may be provided with a longitudinal bore 320 sized to slide over guide pin 208 (shown in FIG. 7E.) Cutter 322 may be located on or near the distal end of drive shaft 318, and affixed thereto by threading, welding, press fitting, adhesive, or other suitable attachment means such that cutter 322 rotates in unison with drive shaft 318. A handle 324 may be provided at the proximal end of drive shaft 318 to allow an operator to manually rotate cutter 322. In some embodiments, a motor or other drive mechanism (not shown) may be coupled to drive shaft 318 to allow automatic rotation.

In the embodiment illustrated in FIG. 11A, cutter 322 is provided with three radially extending cutting tips, each extending the same distance from bore 320 and the axis of rotation. Cutter 322 is shaped and sized to fit through the triangular bore of soft tissue protector 200 (shown in FIG. 7E) and through the triangular bore 48 broached in the bone (shown in FIG. 7D.) During operation, handle 324 (shown in FIG. 11A) may be used to distally advance cutter 322 through the distal end of the soft tissue protector 200, through broached bore 48 in Bone Segment 1 (such as the ilium, depicted in FIG. 7D), and into the space or joint between the bone segments (such as generally between the articulating surfaces of the SI-Joint, as depicted in FIG. 7D.) Once cutter 322 is no longer constrained by soft tissue protector 200 and broached bore 48, it may be rotated in the space or joint between bone segments by rotating handle 324 (FIG. 11A.) When rotated, cutter 322 will cut into the face of Bone Segment 1 (e.g. the ilium) and or the face of Bone Segment 2 (e.g. the sacrum), creating a circular region of decortication.

Figure 11B:
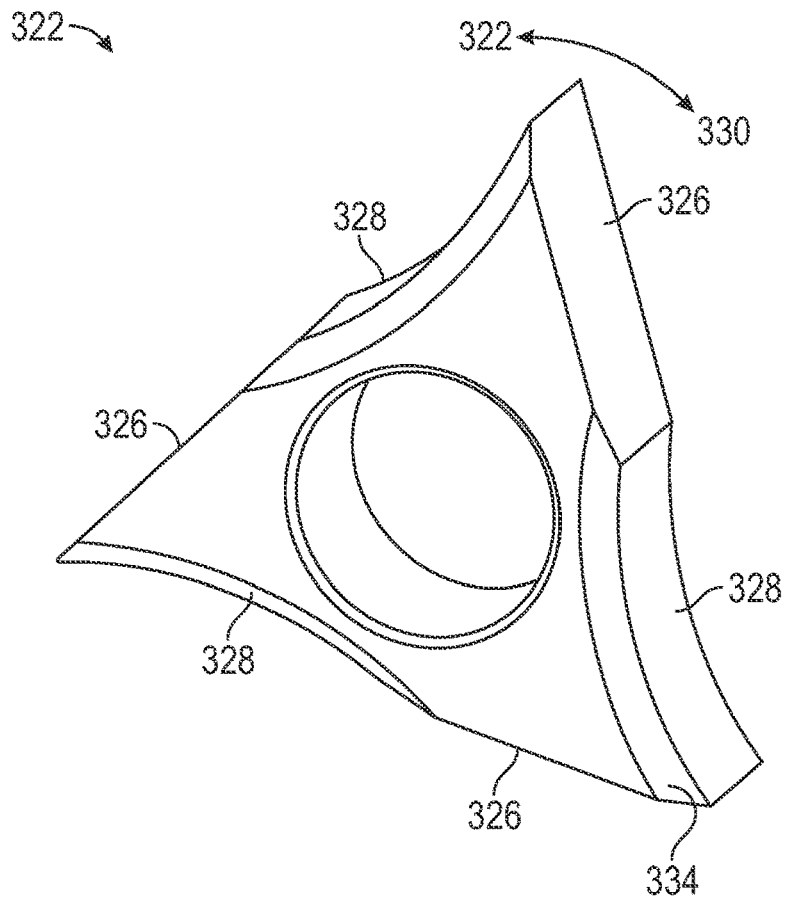
FIG. 11B is an enlarged perspective view showing the cutter of the system of FIG. 11A.

Referring to FIG. 11B, at least one edge of cutter 322 may be provided with a flat portion 326 and a curved portion 328. When cutter 322 is rotated in a first direction 330, flat portion(s) 326 engage with the bone to decorticate, and when rotated in as second direction 332, curved portion(s) 328 engage with the bone to decorticate. In some embodiments, a generally radially extending edge of curved portion(s) 328 may be provided with a chamfer 334 and an opposite generally radially extending edge may be left sharp, as shown in FIG. 11B. In other embodiments (not shown), the radially extending edges on both sides of curved portion(s) 328 may be left sharp. While the illustrated embodiment shows a cutter 322 having three teeth or cutting extensions, other embodiments (not shown) may have one, two or more than three teeth.

Figure 12:
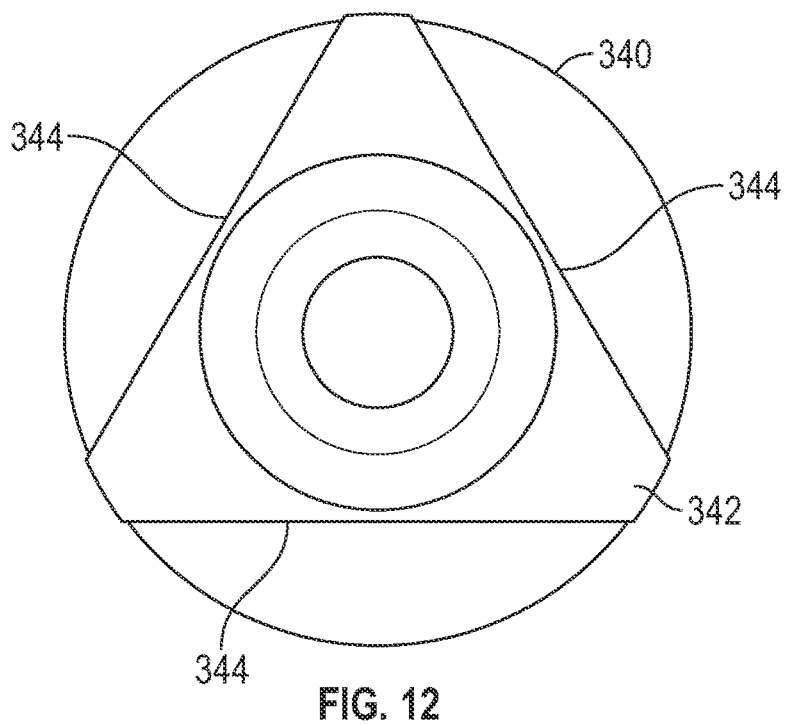
FIG. 12 is an end view depicting an exemplary decortication area provided by the system of FIG. 11A.

Cutter 322 may be sized to completely fill the interior cross-section of the soft tissue protector 200 so that the reach of its cutting tips when rotated outside of this cross-section can be maximized. The outer circle 340 in FIG. 12 depicts the area reached by cutter 322. The generally triangular area 342 within circle 340 represents the cross-sectional area of broached bore 48 formed in the bone, and the cross-sectional area of the implant. The three shaded segments 344 represent the decorticated area of the bone face (i.e. the area of outer circle 340 minus the area of triangle 342.) In some embodiments, the total decorticated area of the three segments 344 is about 0.64 cm$^2$ (on one side of the joint.) In typical procedures wherein both sides of the joint are decorticated, this area is generally the same on both joint surfaces. In some embodiments, the cross sectional area of the triangular working channel of the soft tissue protector 200 is also about 0.64 cm$^2$ (having a base of 1.05 cm and a height of 1.212 cm.) Accordingly, the decorticated area of the joint provided by this exemplary instrument may be about equal to the working channel it passes through.

In some embodiments, the axial thickness of cutter 322 is 3 mm. In some embodiments, the axial thickness of cutter 322 may be sized to be thicker than the space or joint between the bone segments so that the surfaces of both bone segments can be decorticated at the same time. In other embodiments, the axial thickness of cutter 322 may be sized to be thinner than the space or joint between the bone segments so that only one of the surfaces of the bone segments can be decorticated, or so that one surface can first be decorticated, cutter 322 can be moved axially, and then the other surface can be decorticated. In such embodiments, the surgeon is provided with the ability to decorticate each surface independently, with different depths of decortication, different amounts of force applied, etc.

As shown in FIG. 11A, handle 324 may be provided with one or more flat portions 346 and or other clocking/indexing features showing the rotational orientation of drive shaft 318 and cutter 322 relative to soft tissue protector 200. By aligning flat portion 346 with one of the flat sides of stop 316, the surgeon can see that cutter 322 is rotationally lined up with the triangular bore of soft tissue protector 200 so that cutter 322 may be withdrawn through the triangular bore. In some embodiments, a ball detent feature, magnets, lights and or sound may be provided to aid in determining when cutter 322 is properly aligned for withdrawal.

According to aspects of the present disclosure, cutting instrument 300 may be used to decorticate bone surface(s) as follows. As previously described, an incision through soft tissue may be made and a guide pin 208 (shown in FIG. 7F) may be placed along a desired path where an implant is to be inserted. A pin sleeve 204, drill sleeve 202 and soft tissue protector 200 (shown in FIG. 7E) may be placed over the guide pin 208 until the distal end of soft tissue protector 200 contacts an outer bone surface (such as a lateral surface of an ilium.) Pin sleeve 204 may then be removed and replaced with a cannulated drill bit over the guide pin 208 to begin forming a bore through the first bone segment (e.g. ilium) and into the second bone segment (e.g. sacrum) for receiving an implant. The drill bit and drill sleeve 202 may then be removed and a triangular shaped broach may be passed over the guide pin and through soft tissue protector 200 to complete the bore. The broach may then be removed and cutter instrument 300 inserted over guide wire 322 such that cutter 322 passes through soft tissue protector 200, through the first bone segment and into the space or joint between the bone segments (e.g. the SI-Joint.) Imaging, such as a fluoroscope, may be used to confirm that cutter 322 is located in the desired location within the joint. Handle 324 may then be rotated in one or both directions to decorticate one or both surfaces of the joint. During the decortication process, cutter 322 may be further advanced distally and or retracted proximally. Cutting instrument 300 may then be removed and a triangular shaped implant passed over guide wire 322, through soft tissue protector 200, and tapped into place across the joint. After the implant placement is confirmed with imaging, guide wire 322 and soft tissue protector 200 may be removed and the incision closed. In some embodiments, a guide pin is not used, is placed later in the procedure, and or is removed earlier than described above. In some embodiments, the drill bit is not cannulated or is not used. In some embodiments, bone graft such as autograft and/or other bone growth inducing material may be placed in the decorticated area, before and/or after an implant is placed.

In an embodiment similar to system 300 shown in FIG. 11A, a triangular component (not shown) may be provided distal to the cutting element for guiding the cutting element toward the implant bore formed on the opposite side of the bone joint, and or for stabilizing the cutting element during operation.

Figure 13A:
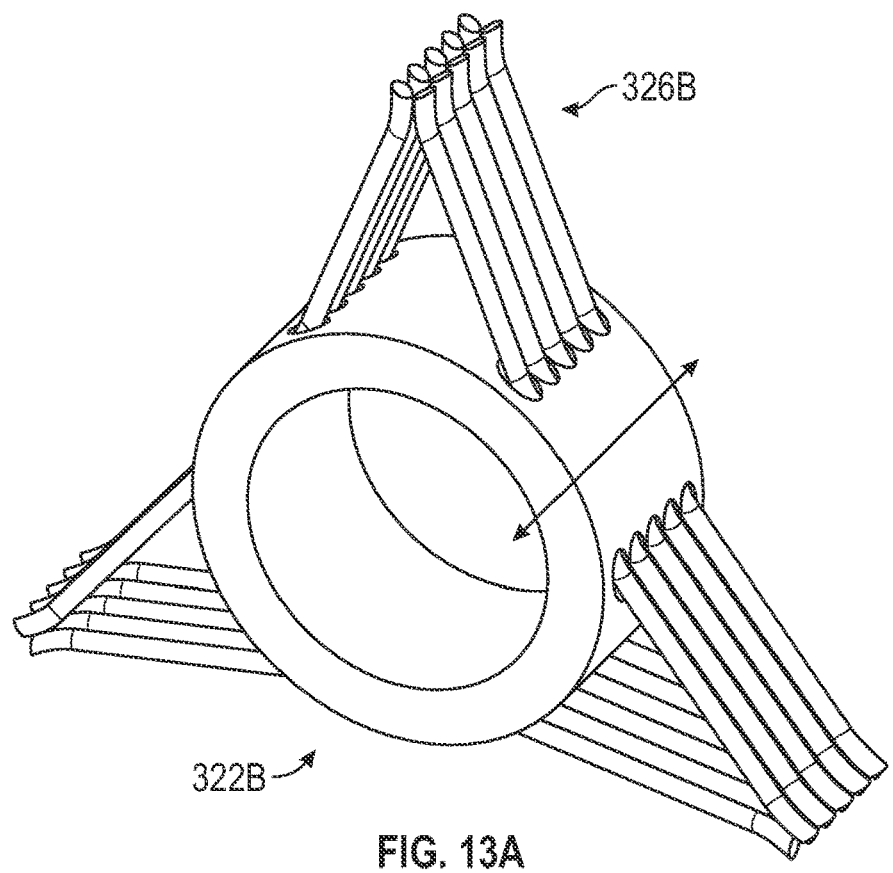
FIG. 13A is a perspective view showing another exemplary cutter that may be used with the system of FIG. 11A.
Figure 13B:
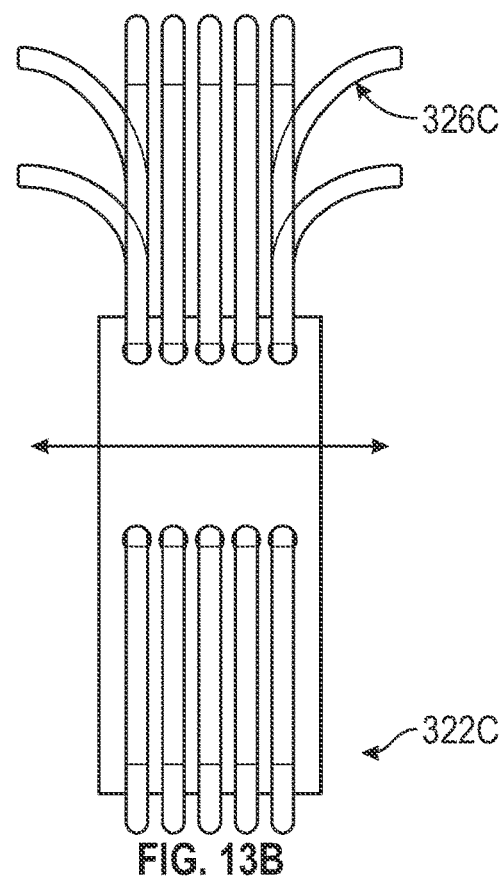
FIG. 13B is a perspective view showing another exemplary cutter that may be used with the system of FIG. 11A.

Referring to FIG. 13A, another exemplary cutter 322B is shown which may be used instead of cutter 322 on instrument 300 as previously described. Cutter 322B may be provided with curved and or straight, flexible metal bristles, ribbons, or blades 326B. As cutter 322B is rotated the bristles are able to deflect/flex to conform to the SI-Joint's irregular surfaces. The flexible bristles can scrape through the joint cartilage, scratch the cortical bone, but not cut away the cortical bone. This leaves the cortical wall intact for better implant support. Also, as the flexible bristles scratch away the cartilage, the cartilage is captured by the bristles like a whisk and can be removed by re-aligning the cutter with the implant bore and removing the instrument from the bone. While the illustrated embodiment shows cutter 322B having bristles all in a line, other embodiments, such as cutter 322C shown in FIG. 13B, may have multiple bristles that point in other directions while still maintaining a substantially triangular shape.

Referring to FIG. 14, another exemplary embodiment of a decorticating system and method is shown. The construction and use of cutting instrument 400 illustrated in FIG. 14 is similar to that of cutting instrument 300 illustrated in FIG. 11A. As shown in FIG. 14, cutting instrument 400 is provided with a larger knob 410 at the proximal end of drive shaft 412 in order to allow the surgeon to apply more torque to cutter 414 at the distal end of drive shaft 412. Knob 410 may be generally triangular in shape as shown, to more easily identify the angular orientation of cutter 414 when aligning it with the main body 416 prior to retracting cutter 414 through the soft tissue protector, as previously described.

Referring to FIG. 15, an enlarged view of the distal end of drive shaft 412 of cutting instrument 400 is shown with cutter 414 removed. Cutter 414 (shown in FIG. 14) is provided with a central hexagonal through bore (not shown.) The distal end of drive shaft 412 is provided with a mating hexagonal rod portion 418 as shown in FIG. 15, configured to be slidably received through the hexagonal bore in cutter 414. Retainer ring 420 is attached to hexagonal rod portion 418 as shown in FIG. 15 to retain cutter 414 in place on rod portion 418.

If the outer surfaces 422 of hexagonal rod portion 418 were parallel to the central longitudinal axis 424 of drive shaft 412, cutter 414 of cutting instrument 400 would rotate in the same way as cutter 322 of cutting instrument 300 shown in FIG. 11A (i.e. would remain in a plane perpendicular to the axis of rotation 422.) However, in this embodiment the outer surfaces 422 of hexagonal rod portion 418 each have a convex curvature. In other words, hexagonal rod portion 418 is thicker at its center than at its proximal and distal ends. This arrangement allows cutter 414 to tip in either direction relative to axis 424. In some embodiments, cutter 414 may tip up to plus or minus 5 degrees from perpendicular. In other embodiments (not shown), cutter 414 may tip more than 5 degrees. Allowing cutter 414 to assume an angle that is not perpendicular to the axis of rotation 424 can be beneficial in situations where the implant bore is not formed perpendicular to the bone joint. For example, if an implant bore in made across an SI-Joint such that the bore crosses the joint's articulating surfaces at an 85 degree angle, allowing cutter 414 to tip to a matching angle of 85 degrees allows cutter 414 to more uniformly decorticate the surfaces of the SI-Joint around the bore implant.

In other embodiments (not shown), the hexagonal rod portion 418 and the hexagonal bore in cutter 414 may be replaced with a resilient material (such as Tygon® or other biocompatible polymer) at the distal end of the drive shaft 412 and or central hub section of cutter 414. Such an arrangement allows the cutter to have a passively compliant angle, as described above.

In other embodiments (not shown), the angle of the cutter may be actively controlled or adjusted. In some embodiments, one or more movable pins may be provided through the main body of the cutting instrument. When a pin is pushed distally against the proximal side of the cutter, that side of the cutter is angled away from the pin and the cutter's angle relative to the axis of rotation is actively changed from being perpendicular to non-perpendicular. As the cutter rotates, it maintains this set angle, even if forces from the bone joint may be urging it back towards perpendicular. In some embodiments, the distal end of the pin(s) directly contact a circular race located on the proximal side of the cutter. In other embodiments, the distal end of the pin(s) contact a ring that is set to a desired angle, and the ring in turn urges the cutter to the desired angle. If the pin(s) are connected to the ring, they may be pushed or pulled by the surgeon to change the angle of the ring and cutter.

Figure 17:
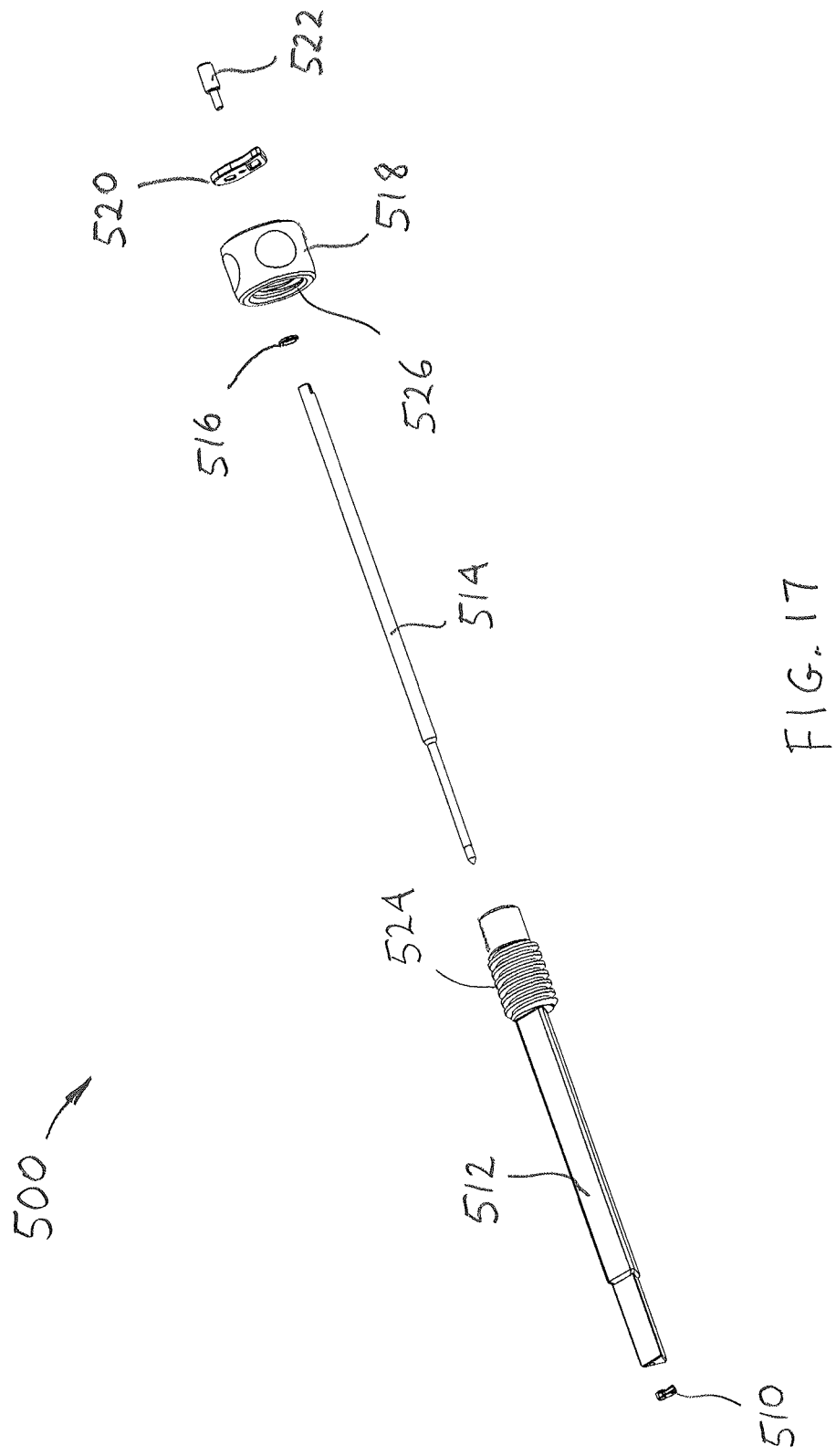
FIG. 17 is an exploded view showing the components of the system of FIG. 16.
Figure 18:
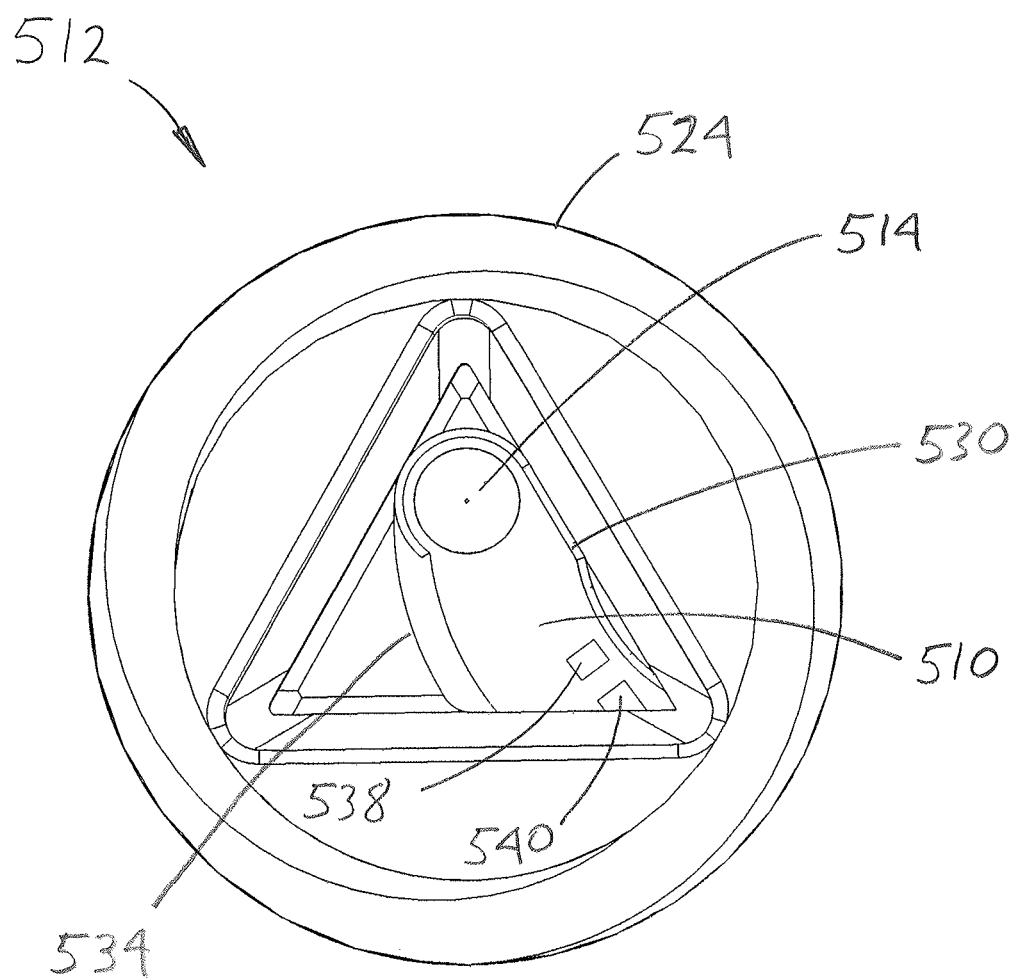
FIG. 18 is an enlarged end view showing the distal end of the system of FIG. 16.

Referring now to FIGS. 16-18, another exemplary embodiment of a decorticating system and method is shown. FIG. 16 is a perspective view showing cutting instrument 500, FIG. 17 is an exploded view showing individual components of the instrument, and FIG. 18 is an enlarged end view showing the distal end of instrument 500. Cutting instrument 500 is similar in construction and use to the previously described instruments. Cutting instrument 500 may be provided with a cutter 510, main body 512, drive shaft 514, washer 516, adjustable stop 518, handle 520 and set screw 522.

Triangularly shaped main body 512 may have a reduced cross-section near its distal end to enable it to more freely pass through an implant bore in bone, while the larger cross-section at the proximal end maintains a sliding fit with a soft tissue protector (not shown), as previously described. Similarly, drive shaft 514 may be stepped down at its distal end as shown in FIG. 17. Drive shaft 514 is received through a bore in main body 512 that is off-axis or laterally displaced from the longitudinal centerline of main body 512, as best seen in FIG. 18. Non-symmetrical cutter 510 is attached to the distal end of drive shaft 514 such that its profile fits within the cross-section of the soft tissue protector and implant bore in at least one orientation. This arrangement of an off-axis drive shaft 514 and non-symmetrical cutter 510 allows the cutter to reach farther away laterally from main body 512 into the bone joint when the drive shaft and cutter are rotated. As can be seen in FIG. 18, when cutter 510 is rotated in one direction, its leading edge comprises a concave or scooped cutting edge, and when rotated in the opposite direction the leading edge comprises a convex cutting edge.

As best seen in FIG. 17, main body 512 may be provided with external threads 524 configured to mate with internal threads 526 within adjustable stop 518. Rotation of stop 518 then causes the stop to move proximally or distally with respect to main body 512, such that the depth that cutter 510 can travel may be adjusted.

Handle 520 may be attached to the proximal end of drive shaft 514 to allow a surgeon to rotate cutter 510. Handle 520 may also be shaped and angularly oriented similar to cutter 510 so the surgeon has a visual indication of what cutter 510 is doing inside the implant bore. In some embodiments, the proximal end of drive shaft 514 is provided with a flat portion on one side which protrudes from the proximal end of main body 524, through washer 516 and into a D-shaped mating hole in handle 520 to maintain a proper orientation between drive shaft 514 and handle 520. Similar features (not shown) may be provided between cutter 510 and the distal end of drive shaft 514 to maintain a desired angular orientation between the two.

Set screw 522 may be threadably engaged with handle 520, offset from the axis of rotation of drive shaft 514 and handle 520. A detent bore (not shown) may be provided in the proximal end of main body 512 for receiving the distal end of set screw 522 when it is distally advanced through handle 520. With this arrangement, a surgeon may lock the angular orientation of cutter 510 by threading set screw 522 into its detent so that the cutter is aligned for passing through the soft tissue protector and into the implant bore in the bone segment(s). Once the cutter is in position within the joint, set screw 522 may be unscrewed until it is withdrawn from the detent bore in main body 512, thereby allowing cutter 510 to be rotated by handle 520. Before cutter 510 is withdrawn from the joint along with main body 512 through the soft tissue protector, set screw 522 can be aligned with the detent bore so that set screw 522 may be threaded into it. In other embodiments (not shown), an indicia line or other marking may be used instead of or in addition to handle 520 to indicate when cutter 510 is in a proper orientation for removal.

In some embodiments (not shown), off-axis cutting instrument 500 may be cannulated so as to slide over a guide wire that has been placed into the joint. In such embodiments, a handle at the proximal end of drive shaft 514 may be configured so that it may be rotated without interfering with the guide wire. In some embodiments (cannulated or non-cannulated), a removable wrench may be provided such that additional torque may be applied to the cutter.

Figure 19:
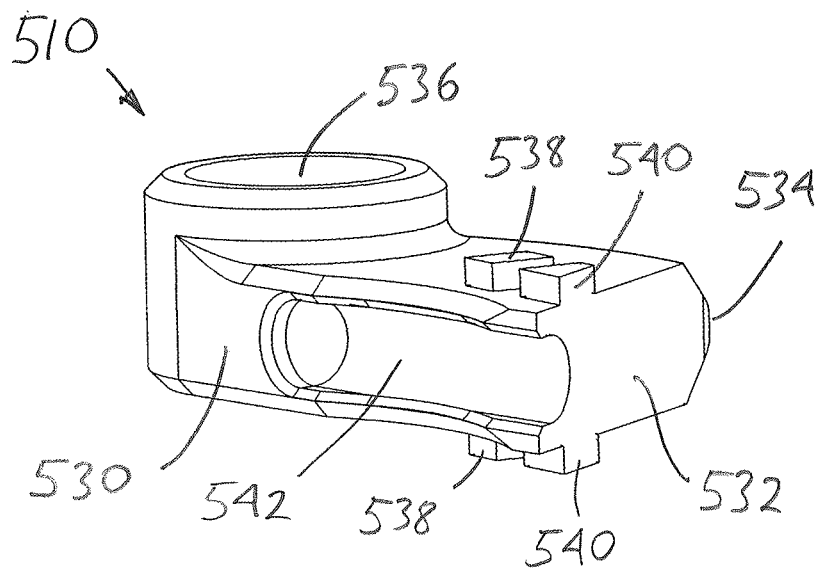
FIG. 19 is an enlarged perspective view showing the concave side and radially outward side of the cutter of FIG. 16.
Figure 20:
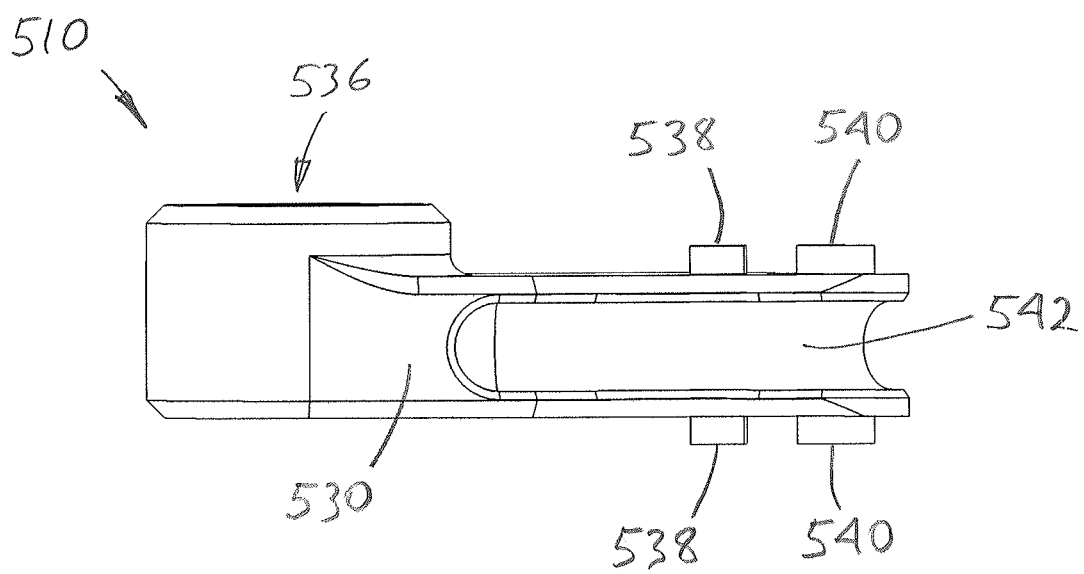
FIG. 20 is an enlarged side view showing the concave side of the cutter of FIG. 16.
Figure 21:
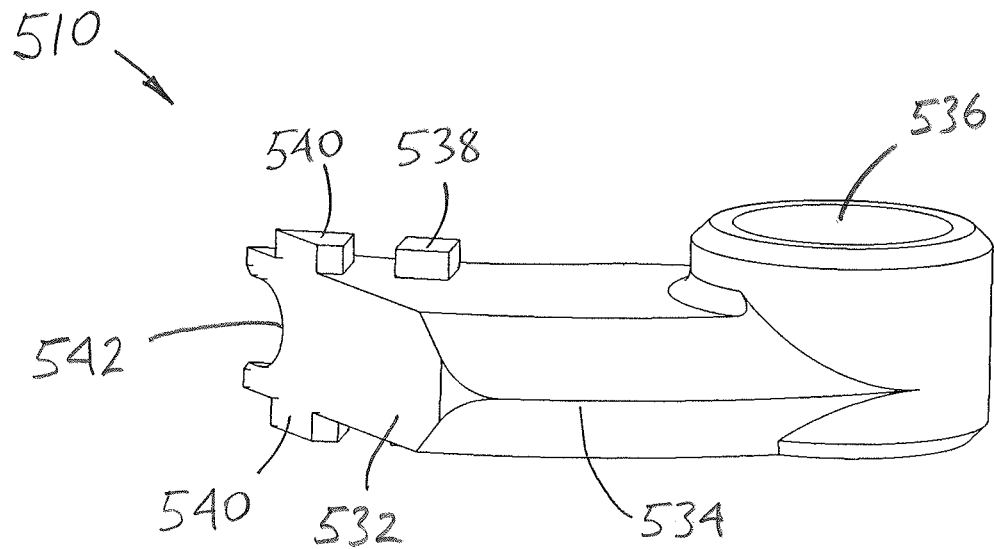
FIG. 21 is an enlarged perspective view showing the convex side and radially outward side of the cutter of FIG. 16.
Figure 22:
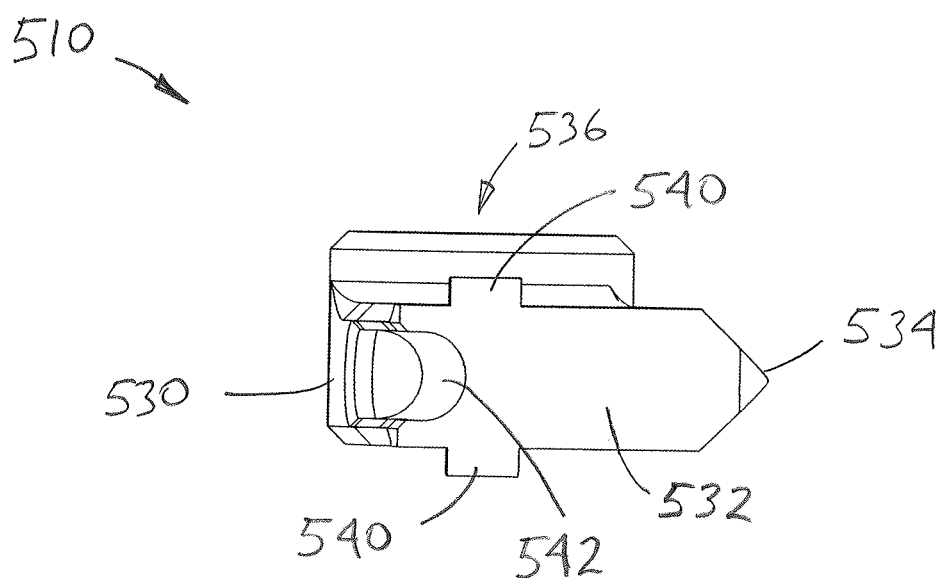
FIG. 22 is an enlarged end view showing the radially outward side of the cutter of FIG. 16.

Referring to FIGS. 19-22, various enlarged views of cutter 510 are shown. In each view, the proximal side of cutter 510 is facing generally up. FIG. 19 is a perspective view showing the concave side 530 and radially outward side 532 of cutter 510, FIG. 20 is a side view showing concave side 530, FIG. 21 is perspective view showing the convex side 534 and radially outward side 532, and FIG. 22 is an end view showing the radially outward side 532.

Cutter 510 may be provided with a bore 536 for receiving the distal end of the drive shaft, as previously described. The proximal (top) and distal (bottom) faces of cutter 510 may each be provided with an inner scraper 538 and an outer scraper 540 (also shown in FIG. 18.) In some embodiments, the main arm of cutter 510 that protrudes radially outward from bore 536 is 2 mm thick, and scrapers 538 and 540 each protrude axially 0.5 mm from the arm, resulting in a maximum cutter arm thickness of 3 mm.

The concave side 530 of cutter 510 may be provided with flat section and a curved section radially outward from the flat section (best seen in FIG. 18.) Concave side 530 may also be provided with a round-bottom channel or scoop 542 extending along a portion of its length, with beveled cutting edges located above and below channel 542. On the opposite side of the cutting arm, convex side 534 may be configured with a single, large, curved bevel, as best seen in FIGS. 21 and 22.

In some implementations, cutter tool 500 is first operated in a counterclockwise direction such that convex side 534 is the leading edge of cutter 510, then operated in a clockwise direction such that concave side 530 becomes the leading edge. This allows convex side 534 to first cut through the cartilage of the joint, then allows concave side 530 to scrape the cartilage from the bone faces. Scrapers or teeth 538 and 540 on both ends of cutter 510 allow for further scraping of cartilage. In some embodiments the scooped side of the cutter when rotated directs cartilage and or bone tissue into the implant bore.

Figure 23:
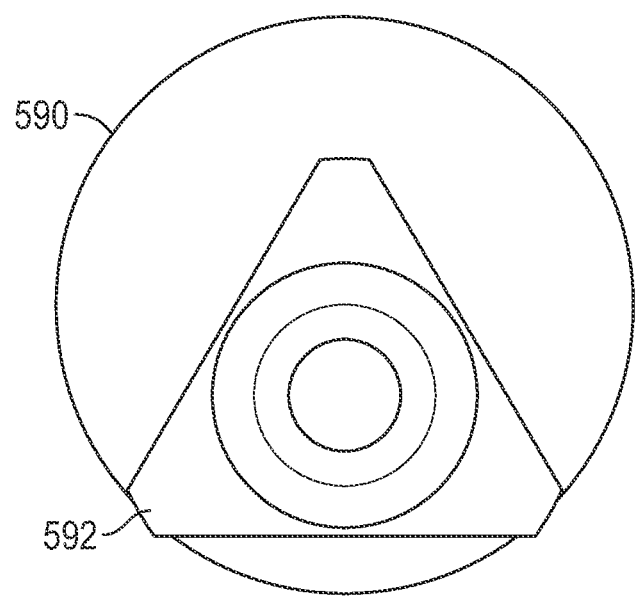
FIG. 23 is an end view depicting an exemplary decortication area provided by the system of FIG. 16 when used in a single apex of a triangular soft tissue protector.
Figure 24:
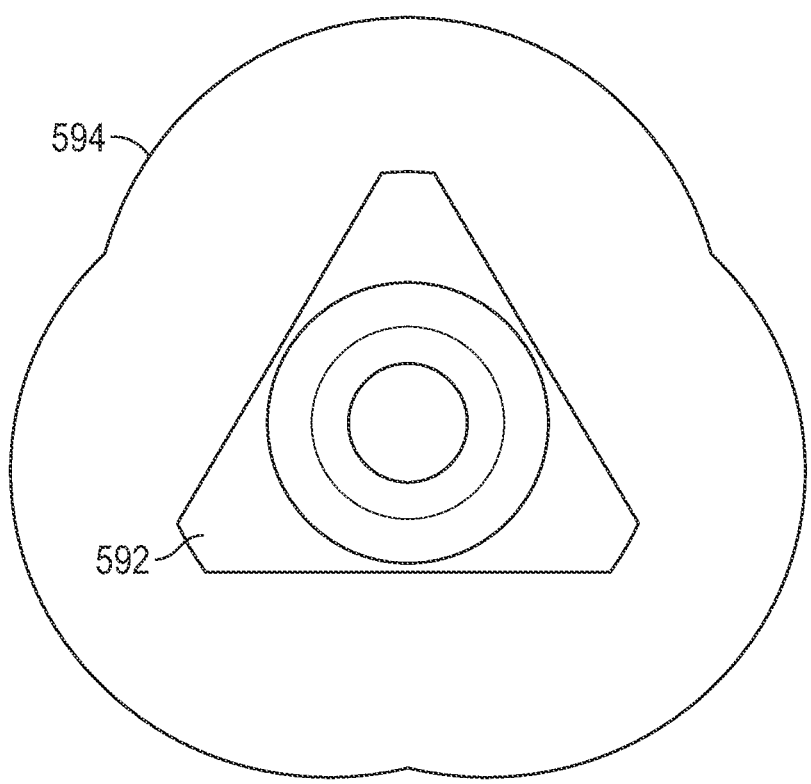
FIG. 24 is an end view depicting an exemplary decortication area provided by the system of FIG. 16 when used in all three apexes of a triangular soft tissue protector.

Referring to FIGS. 23 and 24, the decortication area produced by off-axis cutter system 500 is shown. The outer circle 590 in FIG. 23 depicts the area reached by cutter 510 when it is located in the upper apex of main body 512. The generally triangular area 592 within circle 590 represents the cross-sectional area of broached bore 48 formed in the bone, and the cross-sectional area of the implant. The shaded area (i.e. the area inside circle 590 but outside triangular area 592) represents the decorticated area of the bone. In some embodiments, this decorticated area is about 1.48 cm2 (on one side of the joint.) In typical procedures wherein both sides of the joint are decorticated, this area is generally the same on both joint surfaces. These areas are more than double those depicted in FIG. 12 for on-axis cutting instrument 300. In some embodiments, the cross sectional area of the triangular working channel of the soft tissue protector 200 is also about 0.64 cm2 (having a base of 1.05 cm and a height of 1.212 cm.) Accordingly, the decorticated area of the joint provided by this exemplary instrument may be more than double that of the working channel it passes through.

In some procedures, off-axis cutter 510 may be operated in all three apices of the soft tissue protector to achieve an even larger area of decortication. In other words, main body 512 of instrument 500 may be introduced into a soft tissue protector in one orientation as described above to achieve the decortication pattern depicted in FIG. 23. Then main body 512 is withdrawn, rotated 120 degrees, and reinserted into the soft tissue protector to decorticate around another apex of the soft tissue protector. This procedure is repeated until the area around all three apexes is decorticated, as depicted by the 3-lobed area 594 in FIG. 24. The shaded area (i.e. the area inside perimeter 594 but outside triangular area 592) represents the decorticated area of the bone. In some embodiments, this decorticated area is about 2.81 cm2 (on one side of the joint.) In typical procedures wherein both sides of the joint are decorticated, this area is generally the same on both joint surfaces. These areas are almost double the areas depicted in FIG. 23 when cutting instrument 500 is used in only one apex of the soft tissue protector. In some embodiments, the cross sectional area of the triangular working channel of the soft tissue protector 200 is also about 0.64 cm2 (having a base of 1.05 cm and a height of 1.212 cm.) Accordingly, the decorticated area of the joint provided by this exemplary instrument may be more than four times that of the working channel it passes through.

Figure 25:
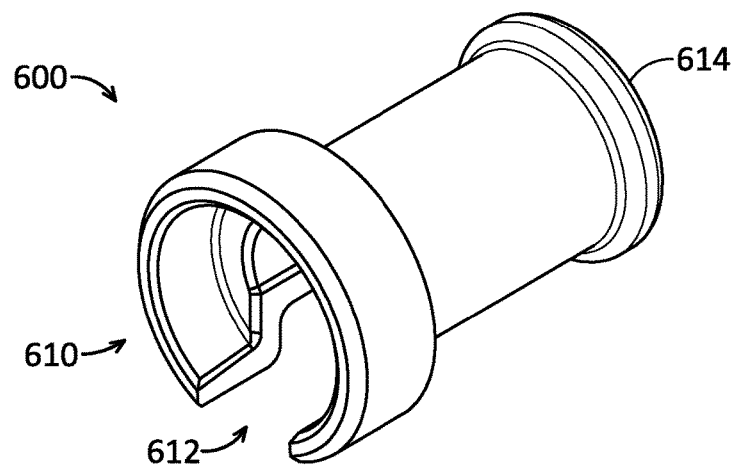
FIG. 25 is a perspective view showing an impactor tool configured for use with the system of FIG. 16.

Referring to FIG. 25, an impactor tool 600 is shown for use with off-axis cutter system 500. Impactor 600 may be provided with a cupped distal end 610 as shown, for mating with the proximal end of adjustable stop 518 (shown in FIG. 16.) A cutout portion 612 may be provided in the cupped distal end 610 so that impactor 600 may be slid on to the proximal end of cutter instrument 500 from the side before moving the cupped end distally over stop 518. Cutout portion 612 may also be configured to allow handle 520 (also shown in FIG. 16) to extend therethrough. The proximal end 614 of impactor 600 may be provided with an enlarged impact surface against which a hammer may be used. With this arrangement, the distal end of cutter instrument 500 may be tapped into place through the implant bore in the bone using a hammer, without damaging the components located on the proximal end of main body 512.

Figure 26:
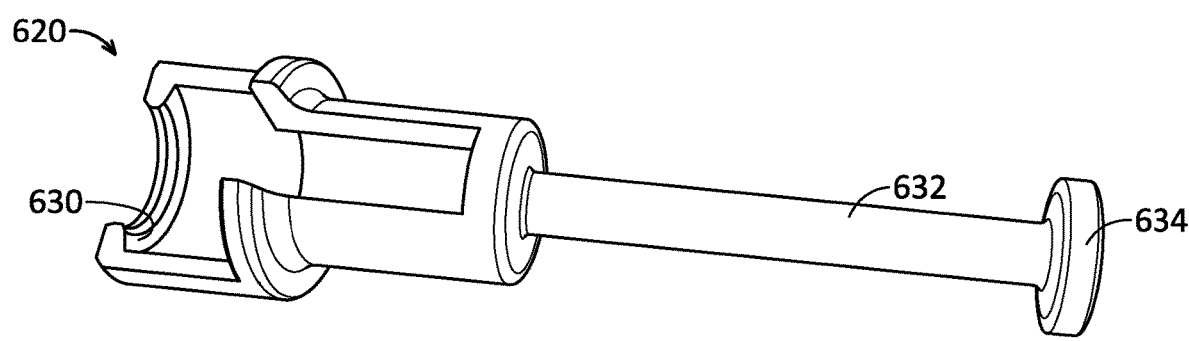
FIG. 26 is a perspective view showing a removal tool configured for use with the system of FIG. 16.

Referring to FIG. 26, a removal tool 620 is shown for use with off-axis cutter system 500. The distal end of removal tool 620 may be half-cylinder shaped so that it may be slid onto adjustable stop 518 (shown in FIG. 16) from the side. The distal end of removal tool 620 may be provided with a radially inwardly extending lip 630 configured to engage the distal underside of adjustable stop 518. The middle of removal tool 620 may comprise a rod portion 632 configured to slidably receive a weighted handle member (not shown.) An enlarged head portion 634 may be provided at the proximal end of rod portion 632 as shown, to captivate the weighted handle member on the rod portion and provide it with an impact surface. With this arrangement, removal tool 620 may be operated as a slide hammer (also known as a slap hammer) to apply impact force to the distal side of stop 518 so that cutter tool 500 may be pulled out from the implant bore formed in the bone.

Figure 27:
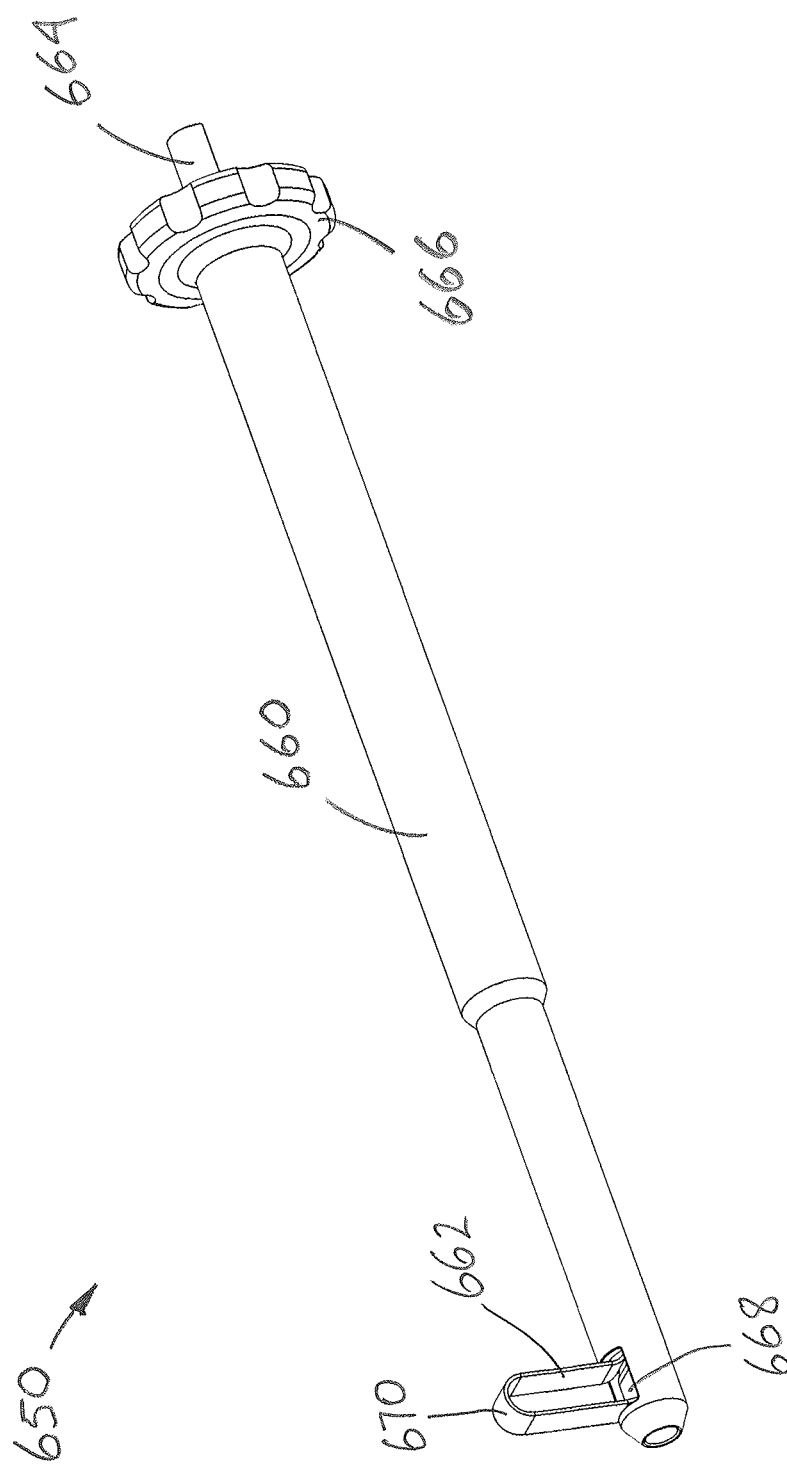
FIG. 27 is a perspective view showing another exemplary embodiment of a decorticating system.
Figure 28:
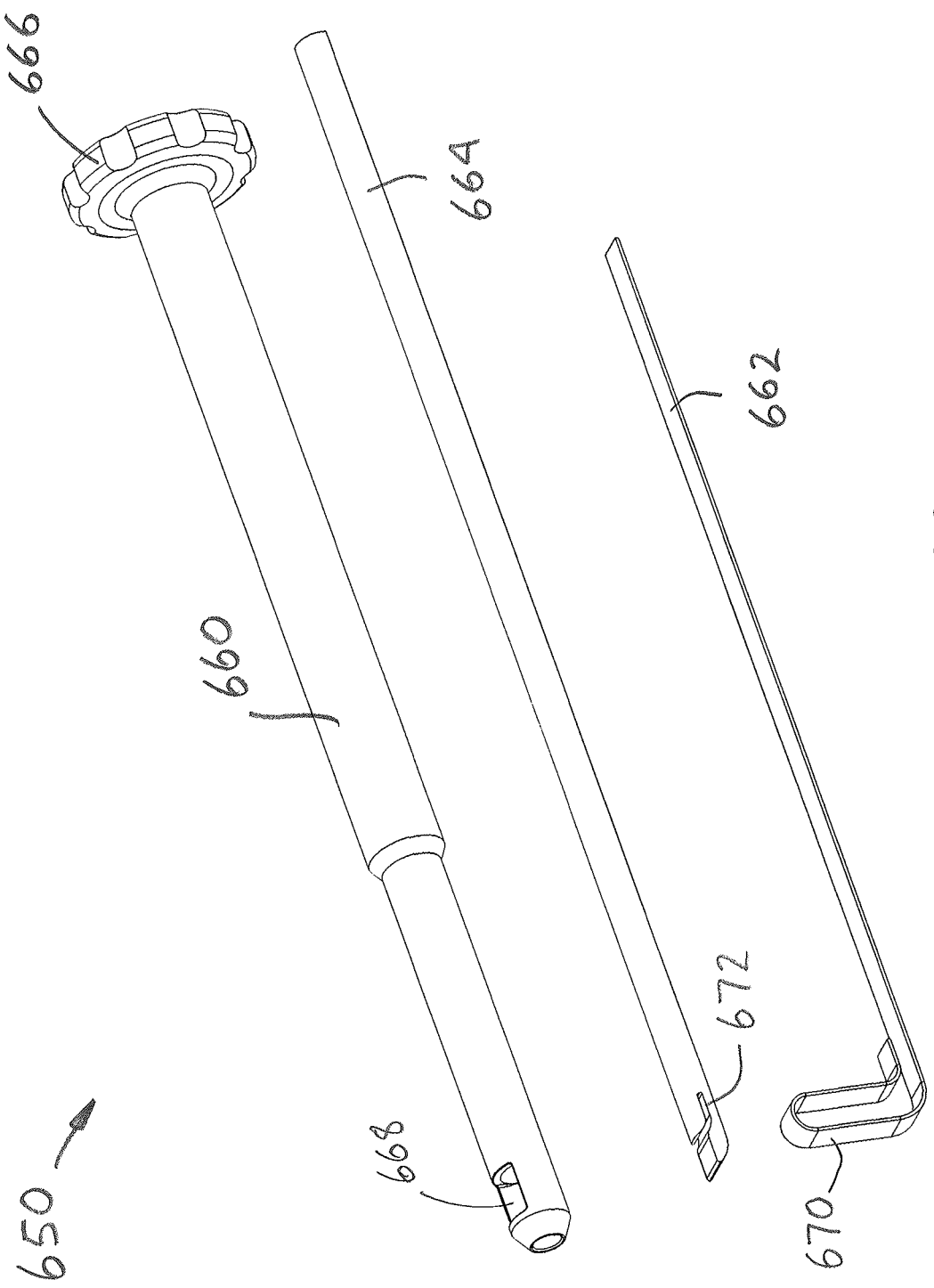
FIG. 28 is an exploded view showing the components of the system of FIG. 27.

Referring now to FIGS. 27-28, another exemplary embodiment of a decorticating system and method is shown. FIG. 27 is a perspective view showing cutting instrument 650, and FIG. 28 is an exploded view showing components of the instrument. Cutting instrument 650 is similar in construction and use to the previously described instruments. Cutting instrument 650 may be provided with a main tube 660, a nitinol strip 662, and a cap rod 664. Main tube 660 may be provided with a handle 666 at its proximal end for rotating the instrument about its longitudinal axis. At the distal end of main tube 660, a window 668 may be provided to allow a distal loop 670 of the nitinol strip 662 to be alternately extended and retracted through the window 668.

In this embodiment, cap rod 664 has a semi-circular cross-section, with the flat side facing down (not seen in the figures.) When instrument 650 is assembled, nitinol strip 662 extends along the flat bottom side of cap rod 664, up along the rounded distal end of cap rod 664, and into slot 672. Cap rod 664 and strip 662 are received within a central bore (not shown) in tube 660. An upwardly curved surface (not shown) may be provided at the distal end of the central bore to help guide strip 662 from the end of the central bore out through window 668. In some embodiments one or both edges of the distal loop 670 of strip 662 are left square, and in other embodiments one or both edges are sharpened.

In operation, the distal end of instrument 650 may be advanced through a soft tissue protector as with previously described embodiments and into a bone joint of a patient. Loop 670 of strip 662 remains retracted within tube 660 (or only slightly protruding through window 668) as instrument 650 is being advanced. Once window 668 is positioned within the joint space, a proximal portion of strip 662 may be distally advanced, such as with a handle or other means (not shown.) In this embodiment, the radial extension of loop 670 may be varied depending on how far strip 662 is distally advanced, but the width of loop 670 is held to a predetermined constant width by the proximal and distal edges of window 668. After loop 670 has been extended to a desired length, handle 666 is turned in one or both directions to decorticate one or both sides of the joint. The proximal portion of strip 662 is then retracted proximally to retract loop 670 into window 668 so that instrument 650 may be withdrawn.

In some embodiments, instrument 650 may be used in conjunction with a guidewire (not shown.) With the guidewire in place across a bone joint, main tube 660 may be advanced along the guidewire without nitinol strip 662 and cap rod 664 in place inside the tube. The guidewire may then be removed from the joint and nitinol strip 662 and cap rod 664 inserted through main tube 660. Alternatively, instrument 650 may be configured to allow nitinol strip 662 and cap rod 664 to be inserted into main tube 660 before it is placed over the guidewire and into the bone joint.

Figure 29:
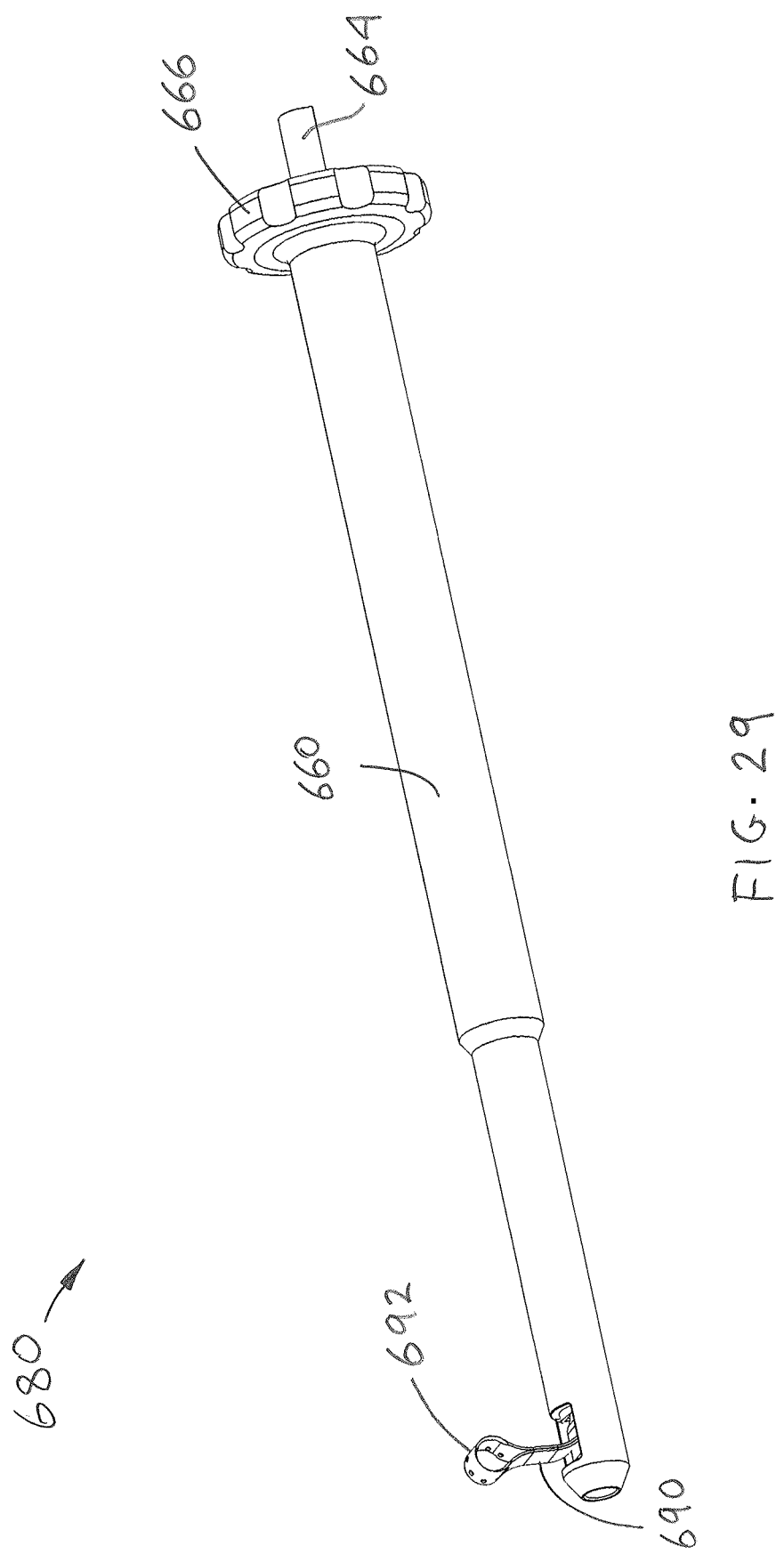
FIG. 29 is a perspective view showing another exemplary embodiment of a decorticating system.

Referring now to FIG. 29, another exemplary embodiment of a decorticating system and method is shown. Cutting instrument 680 is very similar in construction and use to decorticating system 650 shown in FIGS. 27 and 28.

However, instead of having a nitinol strip 662 with a U-shaped distal end 670 (as best seen in FIG. 28), cutting instrument 680 is provided with a nitinol strip 690 having a lollipop-shaped distal end 692. One or both edges of distal end 692 may be sharpened as shown. A series of holes and or protrusions may also be provided such as those shown to allow distal end 692 to have a rasp-like action. With this arrangement, an annular-shaped decorticated area is formed when distal end 692 is rotated about the longitudinal axis of instrument 680. Leaving non-decorticated bone directly adjacent to the implant may increase the stability of the implant. By making a full revolution with distal end 692, a donut-shaped cut is made around the implant bore. Alternatively, a partial revolution may be made, leaving an arc of decorticated area, with a central non-decorticated region connected to an outward non-decorticated region. In some embodiments, this arc extends 120 degrees. In other embodiments, distal end 692 may be extended, rotated a partial revolution, retracted and further rotated (so that it is no longer decorticating bone), extended again, and further rotated, to create multiple arcs of decorticated area. Using such a method, the central non-decorticated region may be connected to the outward non-decorticated region by two or more spokes of non-decorticated bone.

Figure 30:
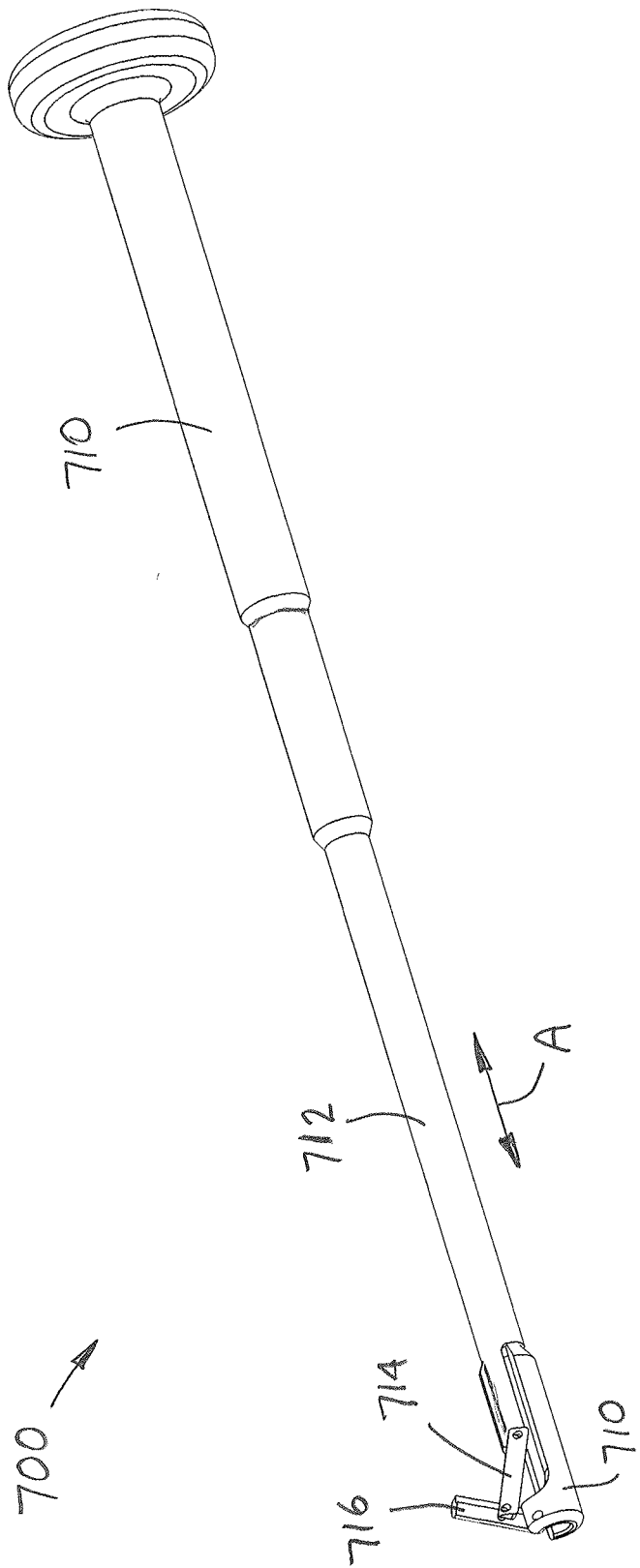
FIG. 30 is a perspective view showing another exemplary embodiment of a decorticating system.
Figure 31:
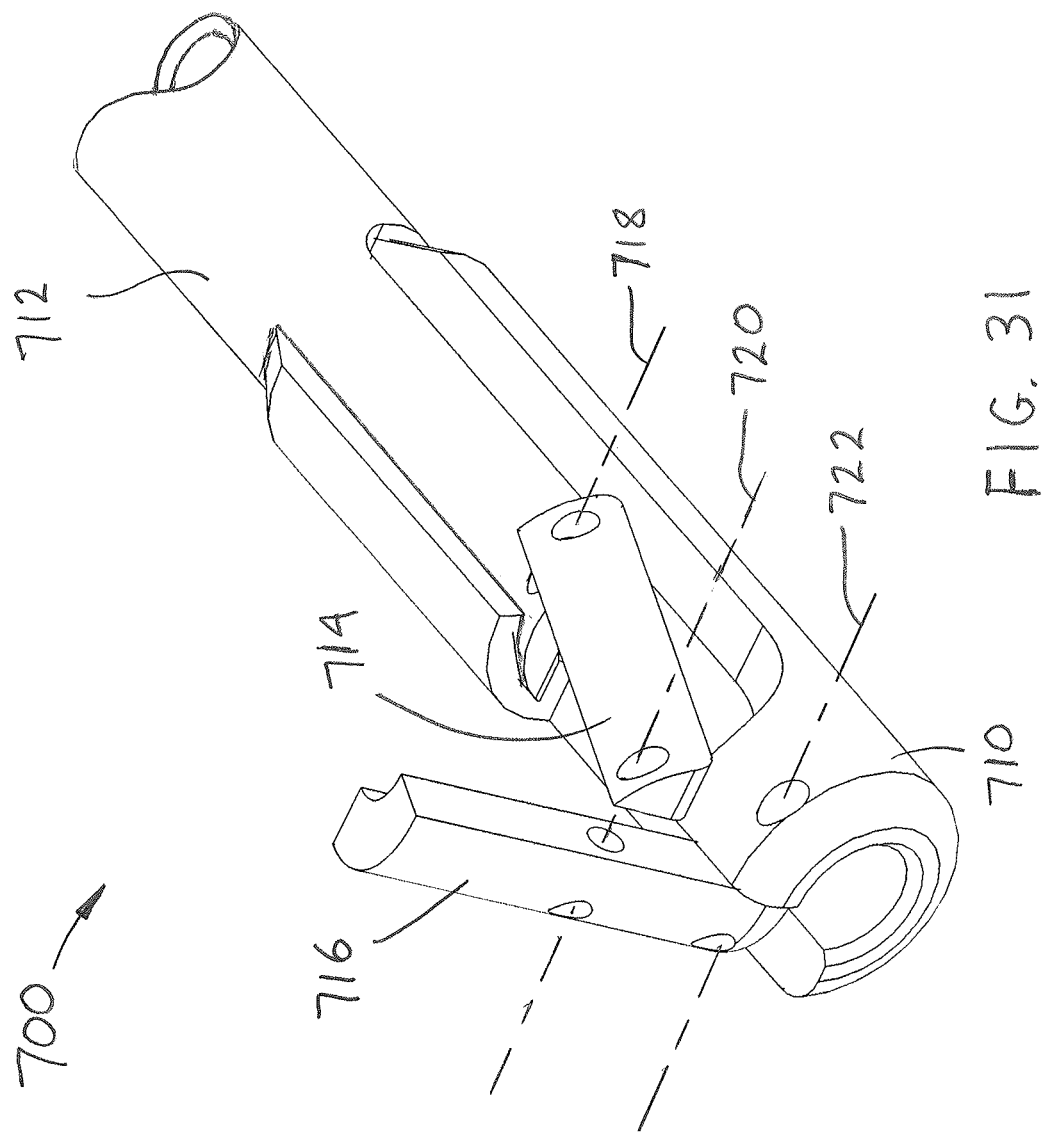
FIG. 31 is an enlarged perspective view showing the distal end of the system of FIG. 30.

Referring now to FIGS. 30-31, another exemplary embodiment of a decorticating system and method is shown. FIG. 30 is a perspective view showing cutting instrument 700 in an expanded state, and FIG. 31 is an enlarged view showing the distal end of the instrument in the expanded state. Cutting instrument 700 is similar in construction and use to the previously described instruments. Cutting instrument 700 may be provided with a main body 710, inner body 712, connecting arm 714 and cutting arm 716. Inner body 712 may be partially received in a bore in main body 710, and may slidably move distally and proximally with respect to main body 710, as depicted by Arrow A in FIG. 30.

As best seen in FIG. 31, the proximal end of connecting arm 714 may be pivotally connected to the distal end of inner body 712 by a first pin (not shown) located on axis 718. The distal end of connecting arm 714 may be pivotally connected to a mid-portion of cutting arm 716 by a second pin (not shown) located on axis 720. The distal end of cutting arm 716 may be pivotally connected to a distal portion of main body 710 by a third pin (not shown) located on axis 722. With this arrangement, the first pin on axis 718 and the third in on axis 722 are both constrained from translating in a radial direction, whereas the second pin on axis 720 is not. As such, when inner body 712 is moved distally, the distal end of connecting arm 714 moves radially outward to the position shown as the proximal end rotates about axis 718. This drives the proximal portion of cutting arm 716 radially outward to the positions shown as the distal end pivots about axis 722. When inner body 712 is moved proximally, connecting arm 714 and cutting arm 716 move radially inward to a retracted position (not shown.) When connecting arm 714 and cutting arm 716 are in the retracted position, they fit into complementary shaped recesses in the distal end of main body 710 such that the assembly generally forms a cylindrical shape. In some embodiments, this cylindrical shape does not exceed 7 mm, allowing the distal end of instrument 700 to fit within a 7 mm bore in the bone.

In operation, when cutting arm 716 is extended as just described, cutting instrument 700 may be rotated to allow cutting arm 716 to decorticate the bone joint. In some embodiments, connecting arm 714 may serve as a cutter as well, or instead of arm 716.

Figure 32:
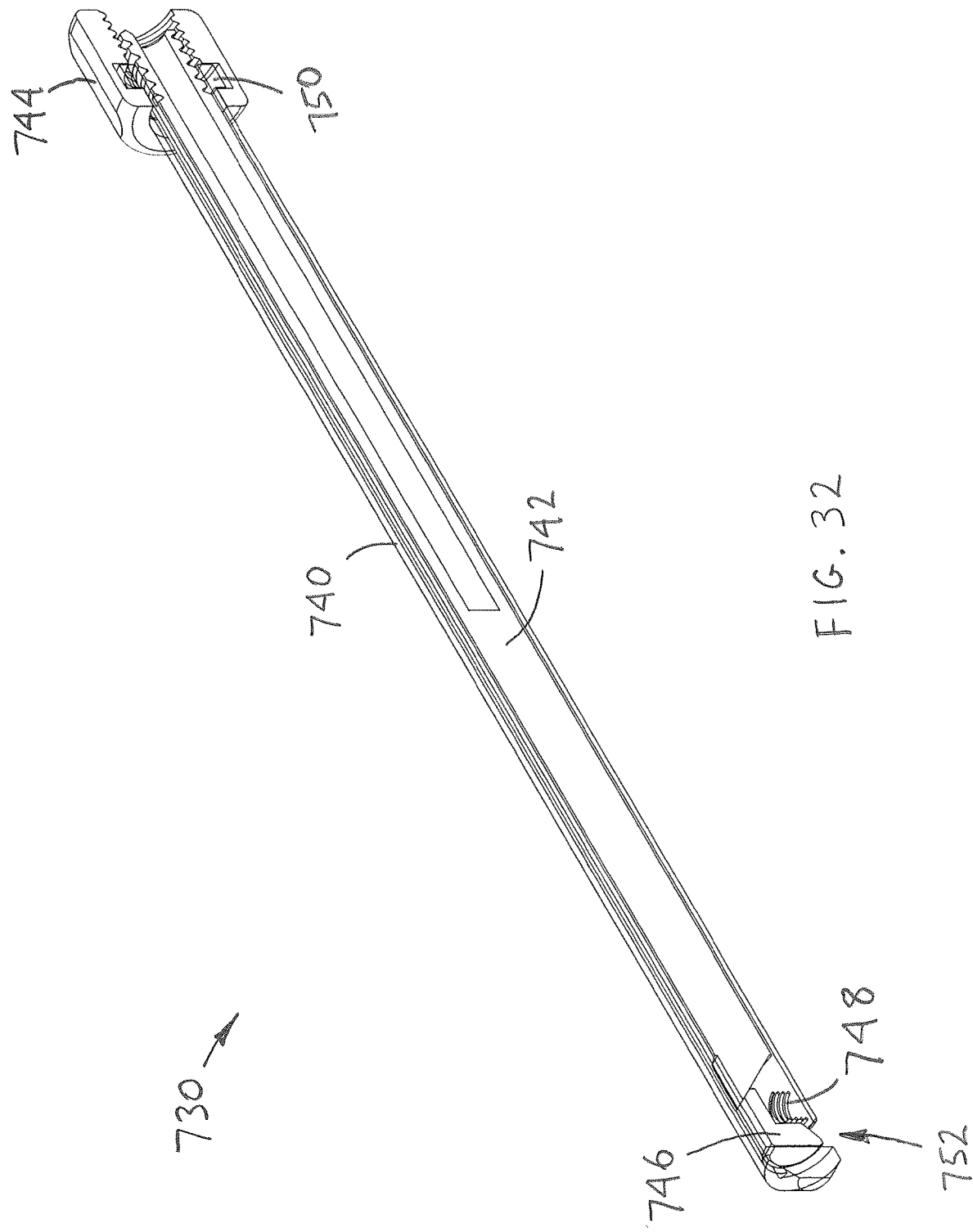
FIG. 32 is a perspective view showing a longitudinal cross-section of another exemplary embodiment of a decorticating system in a retracted state.
Figure 33:
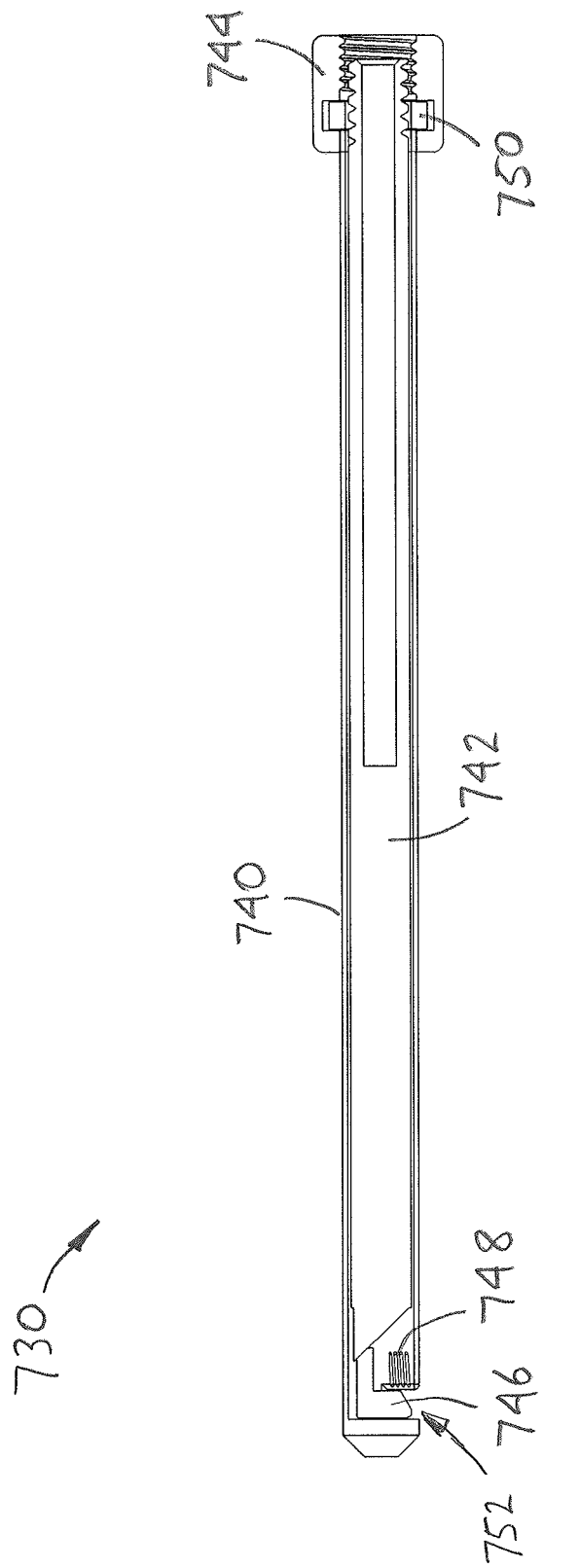
FIG. 33 is a side view showing a longitudinal cross-section of the system of FIG. 32 in a retracted state.

Referring now to FIGS. 32-33, another exemplary embodiment of a decorticating system and method is shown. FIG. 32 is a perspective view and FIG. 33 is a side view, both showing longitudinal cross-sections of cutting instrument 730 in a retracted state. Cutting instrument 730 is similar in construction and use to the previously described instruments. Cutting instrument 730 may be provided with a main tube 740, a wedge 742, an actuation knob 744, a cutting piece 746, and a compression spring 748.

In this embodiment, wedge 742 is an elongated rod with a ramp formed on its distal end and external threads formed on its proximal end. Wedge 742 may be received within a central bore of main tube 740. Inter-engaging features (not shown) may be provided on main tube 740 and wedge 742 to allow longitudinal movement but prevent rotational movement with respect to one another. The proximal end of main tube 740 may be provided with an outwardly protruding ring 750 or similar feature to captivate actuation knob 744 on main tube 740, prevent it from moving longitudinally but allow it to rotate with respect to main tube 740 and wedge 742. The proximal end of wedge 742 may be provided with external threads that mate with the internal threads of actuation knob 744, such that when knob 744 is turned in one direction wedge 742 is driven distally, and when turned in the opposite direction knob 744 drives wedge 742 proximally.

The distal end of main tube 740 may be provided with a window 752 which permits cutting piece 746 to move radially outward from a retracted position (as shown) to an extended position (not shown), in which a portion of cutting piece 746 extends beyond the outer diameter of main tube 740. Cutting piece 746 may be provided with a portion that engages with the ramp formed on the distal end of wedge 742. With this arrangement, when actuation knob 744 drives wedge 742 distally, wedge 742 in turn drives a portion of cutting piece 746 radially outward through window 752 against the force of compression spring 748. With cutting piece 746 extended, instrument 730 may be rotated to decorticate a bone joint. When wedge 742 is driven proximally by knob 744, spring 748 returns cutting piece 746 to the retracted position.

Figure 34:
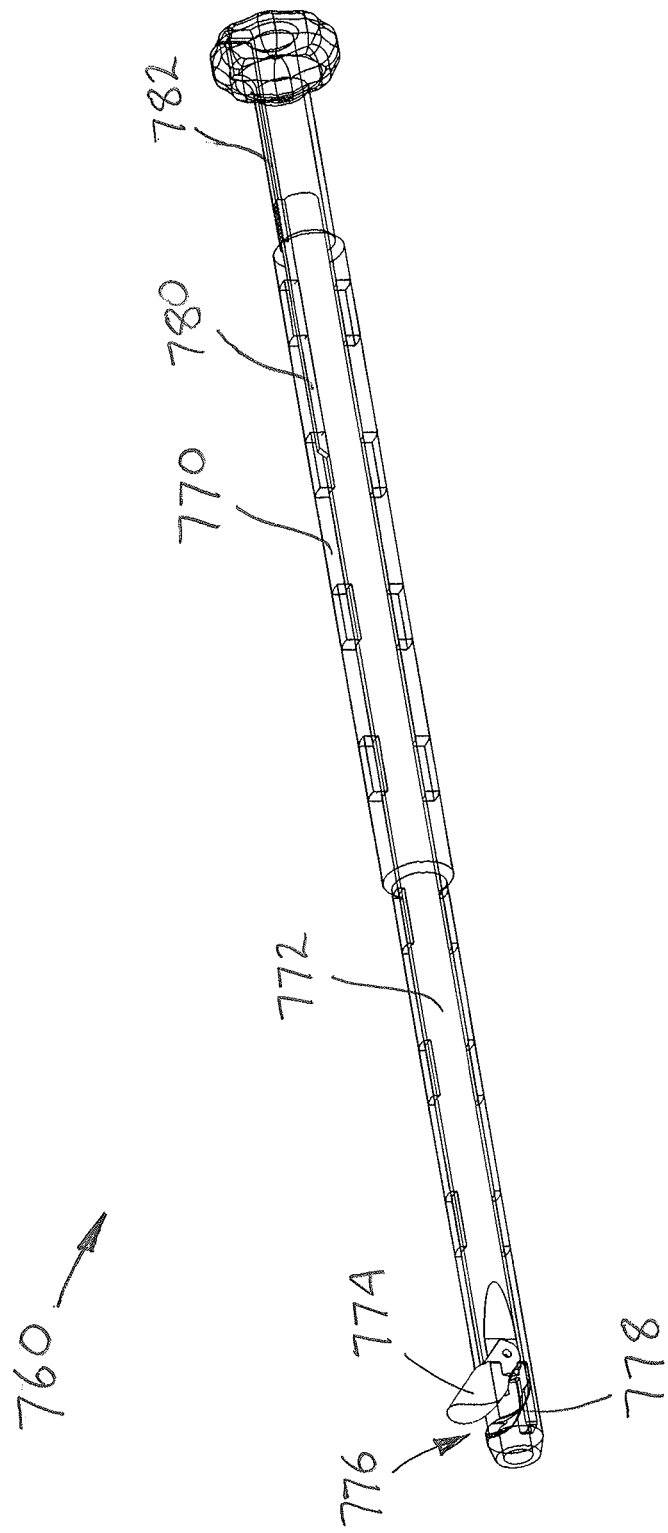
FIG. 34 is a perspective view showing another exemplary embodiment of a decorticating system, with the outer components shown in a transparent fashion so that inner features may be seen.
Figure 35:
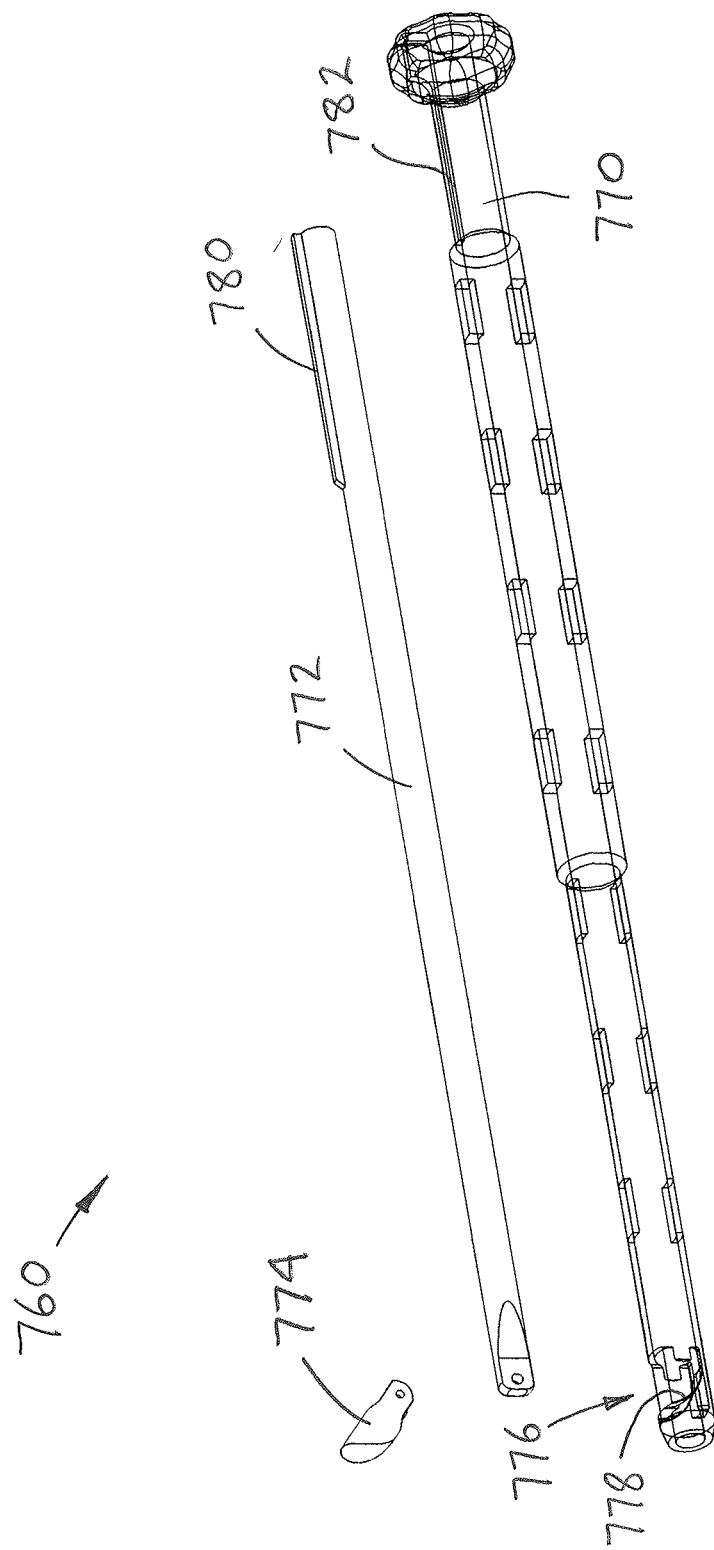
FIG. 35 is an exploded view showing the components of the system of FIG. 34, with the outer components shown in a transparent fashion so that inner features may be seen.

Referring now to FIGS. 34-35, another exemplary embodiment of a decorticating system and method is shown. FIG. 34 is a perspective view showing cutting instrument 760, and FIG. 35 is an exploded view showing components of the instrument, with both figures showing the outer components in a transparent fashion so that inner features may be seen. Cutting instrument 760 is similar in construction and use to the previously described instruments. Cutting instrument 760 may be provided with a main body 770, a drive rod 772 and a cutter arm 774.

Drive rod 772 may be slidably received within a central bore in main body 770. Cutter arm 774 may be pivotably attached to the distal end of drive rod 772 with a pin (not shown.) The distal end of main body 770 may be provided with a window 776 radially connecting the central bore of main body 770 with the exterior. An outwardly extending ramp 778 may be provided at the distal end of the central bore such that when drive rod 772 and cutter arm 774 are urged in a distal direction, a distal, curved portion of cutter arm 774 engages with ramp 778 and cutter arm 774 is pivoted radially outward through window 776. Once cutter arm 774 is radially extended, instrument 760 may be rotated to decorticate the bone joint. Pulling proximally on drive rod 772 causes the proximal side of cutter arm 774 to contact the proximal side of window 776, causing cutter arm 774 to retract within main body 770.

A longitudinally extending spline 780 or similar feature may be provided on the exterior of drive rod 772 for mating with a groove 782 located on the interior of main body 770. This arrangement allows drive rod 772 to slide longitudinally but not rotate inside main body 770, to preserve the correct orientation of cutter arm 774 with respect to window 776. In some embodiments, the main body may be provided with telescoping features to allow its length to be adjusted.

Figure 36:
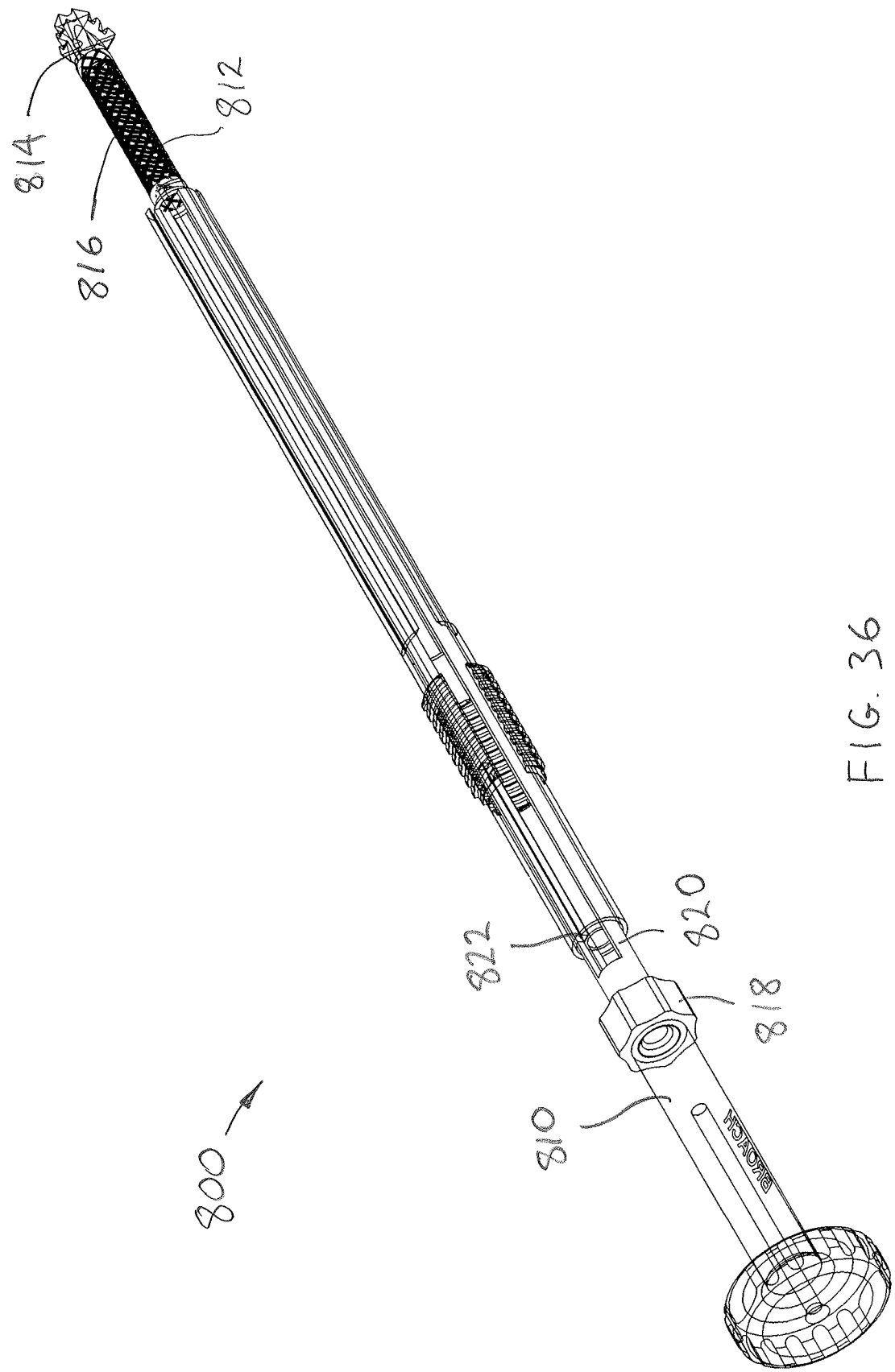
FIG. 36 is a perspective view showing another exemplary embodiment of a decorticating system, with the outer components shown in a transparent fashion so that inner features may be seen.
Figure 37:
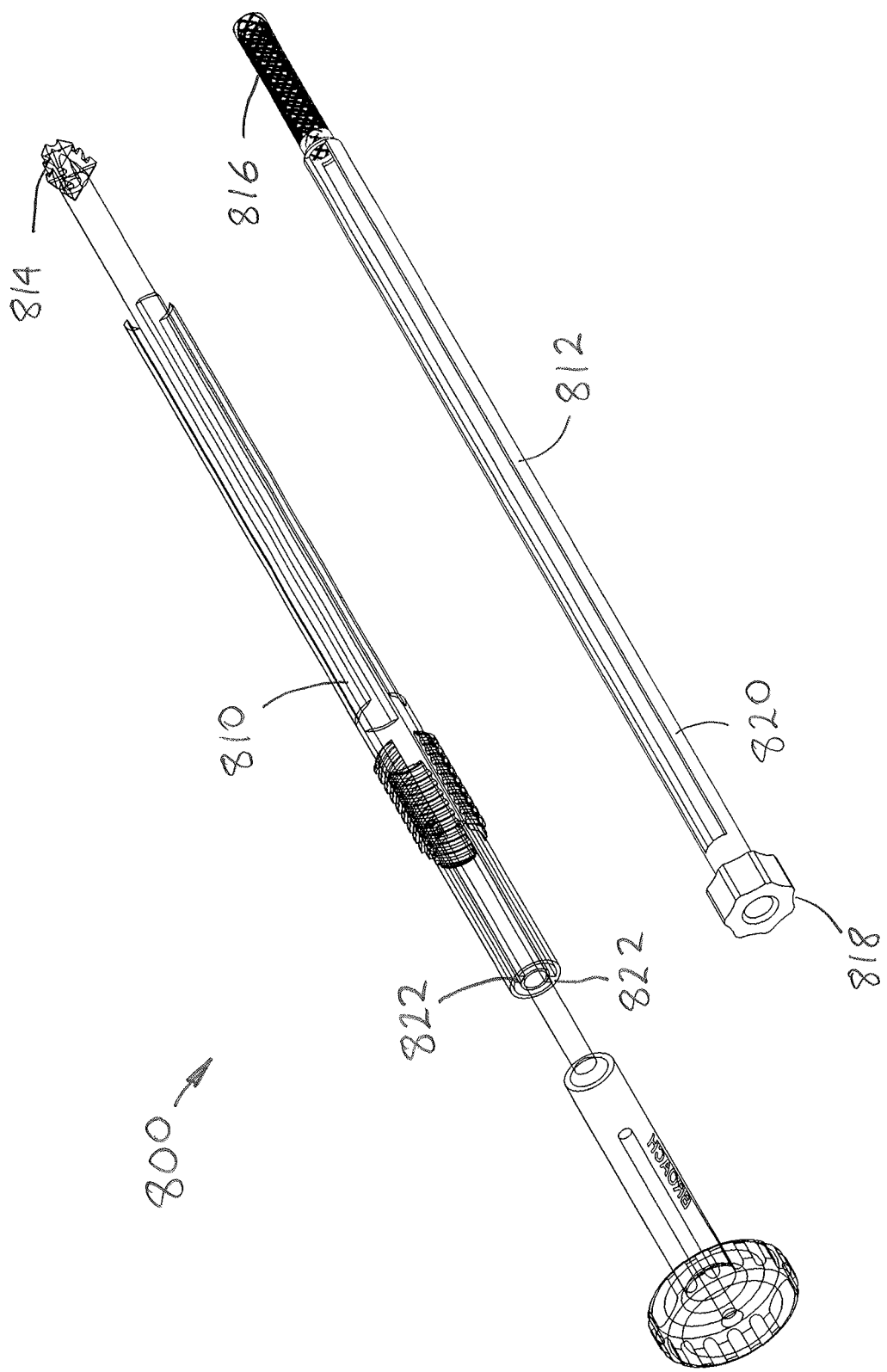
FIG. 37 is an exploded view showing the components of the system of FIG. 36, with the outer components shown in a transparent fashion so that inner features may be seen.

Referring now to FIGS. 36-37, another exemplary embodiment of a decorticating system and method is shown. FIG. 36 is a perspective view showing cutting instrument 800, and FIG. 37 is an exploded view showing components of the instrument, with both figures showing the outer components in a transparent fashion so that inner features may be seen. Cutting instrument 800 is similar in construction and use to the previously described instruments. Cutting instrument 800 may be provided with a main assembly 810 and a rasp assembly 812 that fits over the distal portion of main assembly 810.

In this embodiment, the distal tip of main assembly 810 is provided with a broach 814. Broach 814 may have a triangular cross-section as shown, for forming a channel across a bone joint for receiving a triangular implant. The distal end of rasp assembly 812 may be provided with a flexible, tubular-shaped wire rasp 816. Both FIGS. 36 and 37 show rasp 816 in a radially retracted state. Rasp 816 may be connected to an actuation handle 818 by a slotted tube 820. When rasp assembly 812 is assembled with main assembly 810, longitudinal rails 822 project radially inward from the inside diameter of a main tubular portion of main assembly 810 and through the elongated slots of slotted tube 820. This arrangement allows rasp assembly 812 to move axially but not rotate with respect to main assembly 810.

In operation, the distal end of instrument 800 is tapped across a bone joint as broach 814 forms or further forms an implant bore in the bone segments on either side of the bone joint. Rasp 816 is positioned such that its center generally resides in the joint space. Actuation handle 818 is then pushed distally, causing tubular rasp 816 to be pushed against the proximal side of broach 814, foreshorten and expand into the joint space. Once expanded (not shown), the central portion of rasp 816 will generally take on a disc shape having a larger diameter, and a thickness generally equal to the width of the joint space. The proximal and distal portions of rasp 816 may maintain their original cylindrical shape. Instrument 800 may then be rotated, causing rasp 816 to decorticate bone face(s) of the joint. By urging instrument 800 in the proximal and or distal direction(s), more force may be applied to one bone face as rasp 816 is rotated. In some embodiments, because of the braided wire structure of rasp 816, it is able to provide a more resilient force against the bone surfaces of the joint than a fixed cutting blade, resulting in a more uniform decortication of the joint. After the joint has been decorticated, actuation handle 818 may be pulled proximally to retract rasp 816 toward its original shape so that it may be removed from the bone joint.

Figure 38:
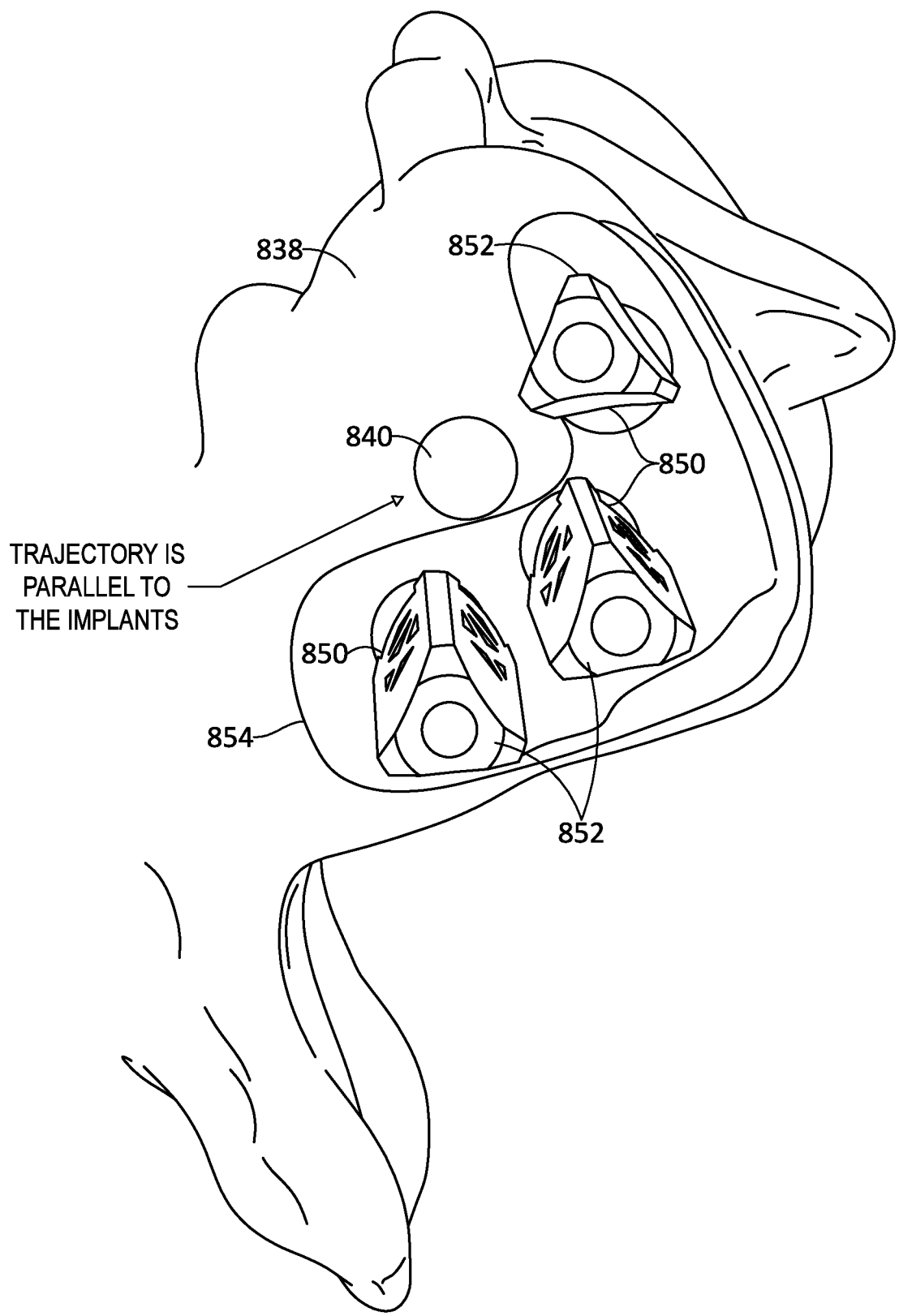
FIG. 38 is a side view showing the right side of a sacrum with the ilium removed for clarity, with an extra channel formed across the SI-Joint according to aspects of the disclosure to aid in decorticating the bone joint.

Referring to FIG. 38, a further aspect of the disclosure will be described. FIG. 38 shows the right lateral side of a sacrum 838, with the ilium removed for clarity. In some embodiments, one or more extra channels may be formed in the bone to aid in decorticating the bone joint. These channels may have a circular, triangular, or other shape. For example, an extra triangular channel (not shown) may be formed through the right ilium and into and/or across an SI-Joint. The extra channel may be formed parallel to one or more implant bores 850. This extra channel is not used to receive an implant 852 as are the other three channels 850 shown in FIG. 38. Instead, it is formed to receive a decortication instrument (not shown), such as those described herein. The decortication instrument may be used to decorticate or aid in decorticating the area(s) around the implant bore(s) 850, and or it may be used to decorticate an area 840 around the extra bore. In the example shown in FIG. 38, three implant bores 850 are created across the SI-Joint, each for receiving an implant 852. Before the implants 852 are placed in bores 850, bores 850 and the extra bore are used to decorticate the bone joint adjacent to each bore, such as previously described. Bone graft chips or other filler material may be placed into the extra channel after it is used for decortication. In some embodiments, the typical spacing between implants is about 15 mm. In some embodiments, some or all of the boomerang shaped articular region 854 of the SI-Joint is decorticated. In some embodiments, decortication is performed posterior or dorsal to the articular region.

Figure 39:
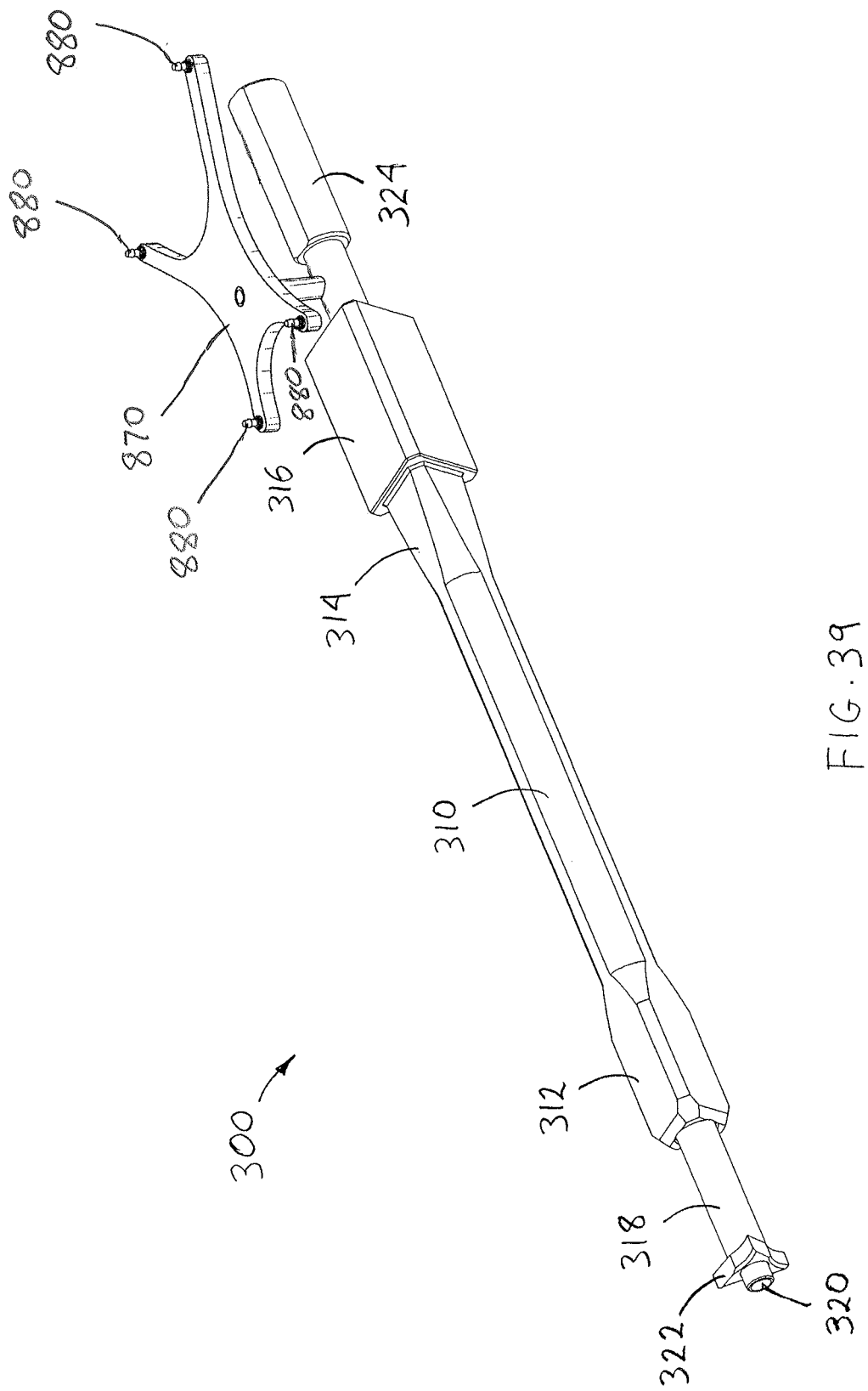
FIG. 39 is a perspective view showing an exemplary embodiment of a decorticating decortication system having navigational features.

Referring to FIG. 39, features may be provided on or added to the decortication instruments described herein to aid in navigation of the instrument, particularly with regard to a reference frame associated with a patient on an imaging system. For example, navigation array 870 may be permanently or removably mounted near the proximal end of drive shaft 318 of decortication system 300. In the exemplary embodiment shown, four emitters or reflectors 880 are located at predetermined and unique distances from one another on array 870 to generate a signal representing the trajectory, depth and or orientation of cutter 322 relative to a portion of a patient's anatomy. In some embodiments, navigation array 870 may include tracking devices capable of being tracked by a corresponding sensor array, such as, for example, a tracking device that actively generates light signals, acoustic signals, magnetic signals, electromagnetic signals and or radiologic signals. Array 870 may passively reflect such signals that are then received by a corresponding sensor array. For example, four reflectors 880 may be provided in the form of reflective spheres of a predetermined diameter whose positions are tracked by navigation system cameras. Further details on how such navigation systems may be implemented can be found in the following references: U.S. Pat. No. RE45,484 to Foley et al., U.S. Pat. No. 8,467,851 to Mire et al., U.S. Pat. No. 6,556,857 to Estes et al., and U.S. Pat. No. 9,451,999 to Simpson et al. Medtronic currently provides a navigation array under the product name SureTrak® for use with their StealthStation® surgical imaging and navigation system.

Figure 40:
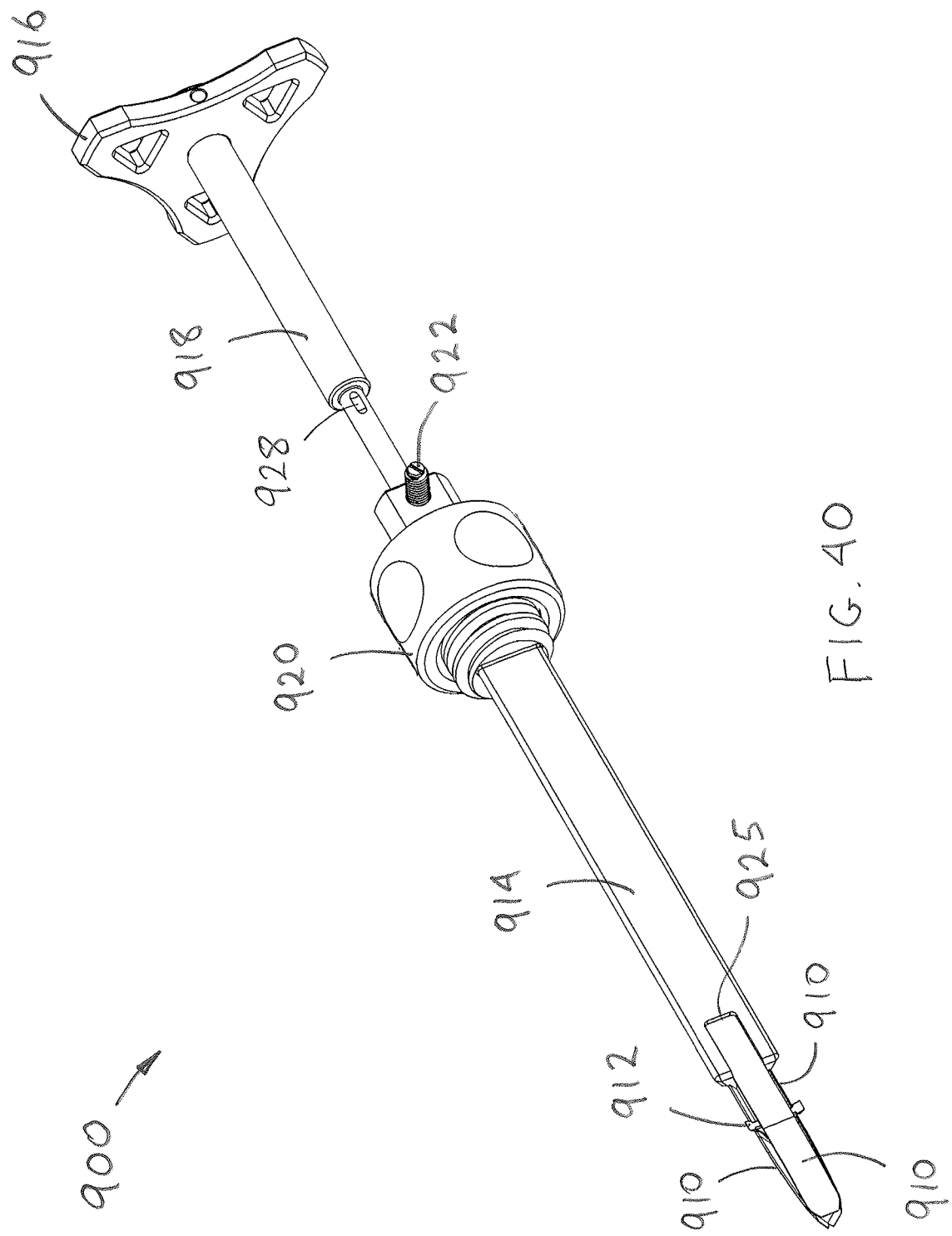
FIG. 40 is a perspective view showing another exemplary embodiment of a decorticating system in a closed state.
Figure 41:
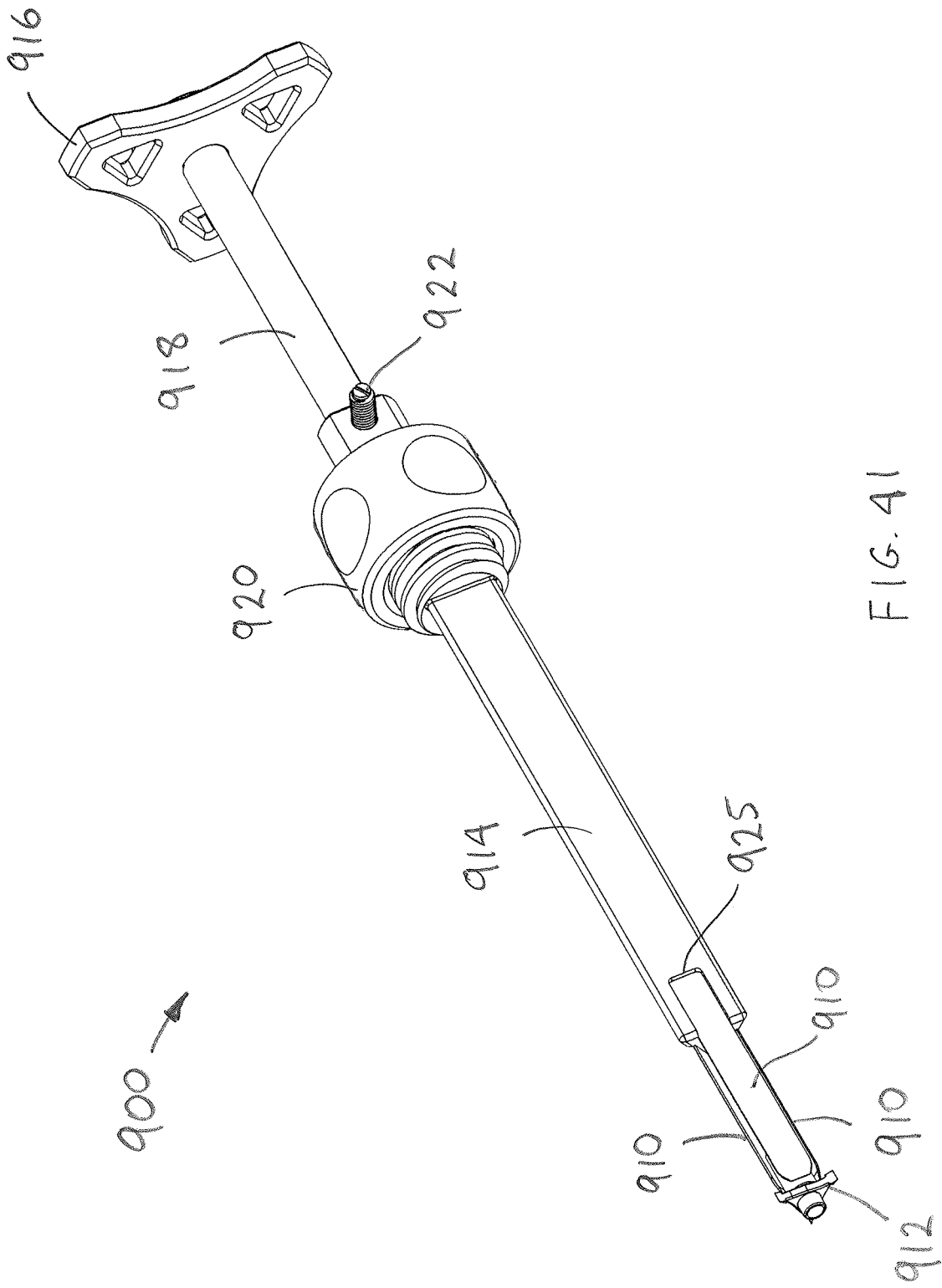
FIG. 41 is a perspective view showing the decorticating system of FIG. 40 in an open state.
Figure 42:
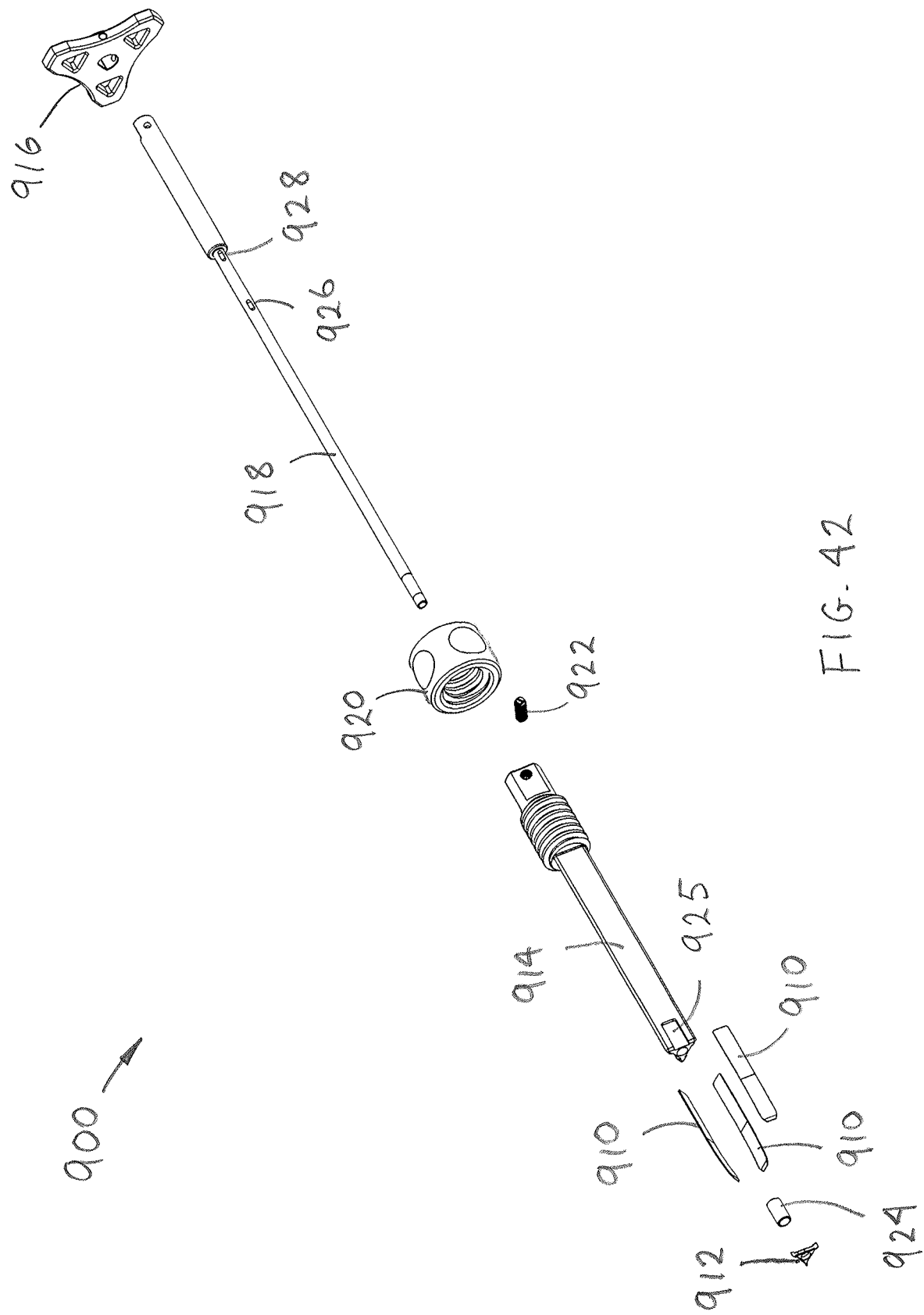
FIG. 42 is an exploded view showing the components of the decorticating system of FIG. 40.

Referring to FIGS. 40-42, another exemplary embodiment of a decorticating system and method is shown. FIG. 40 shows cutting instrument 900 in a closed state, FIG. 41 shows the instrument in an open state, and FIG. 42 is an exploded view showing components of the instrument. System 900 includes three thin blades 910 to help align the cutter 912 with the instrument body 914 as it's being advanced and removed from the pelvis and soft tissue protector. Instrument 900 further includes handle 916, drive shaft 918, adjustable stop 920, ball-nose spring plunger 922, and washer stop 924 (shown only in FIG. 42.) The proximal ends of blades 910 may be rigidly attached to recesses 925 located at the distal end of body 914.

As shown in FIG. 42, drive shaft 918 may be provided with two detents 926 and 928. Each detent is configured to alternately engage with ball-nose spring plunger 922 when it is threaded into the proximal end of body 914. Handle 916 may be used to pull drive shaft 918 proximally so that plunger 922 engages with distal detent 926 and cutter 912 is retracted into blades 910 as shown in FIG. 40, or to push drive shaft 918 distally so that plunger 922 engages with proximal detent 928 and cutter 912 is extended from blades 910 as shown in FIG. 41. Cutter 912 may be placed in the retracted state as shown in FIG. 40 when instrument 900 is being moved into and out of the patient, and may be placed in the extended state as shown in FIG. 41 when being used to decorticate a bone joint.

Figure 43:
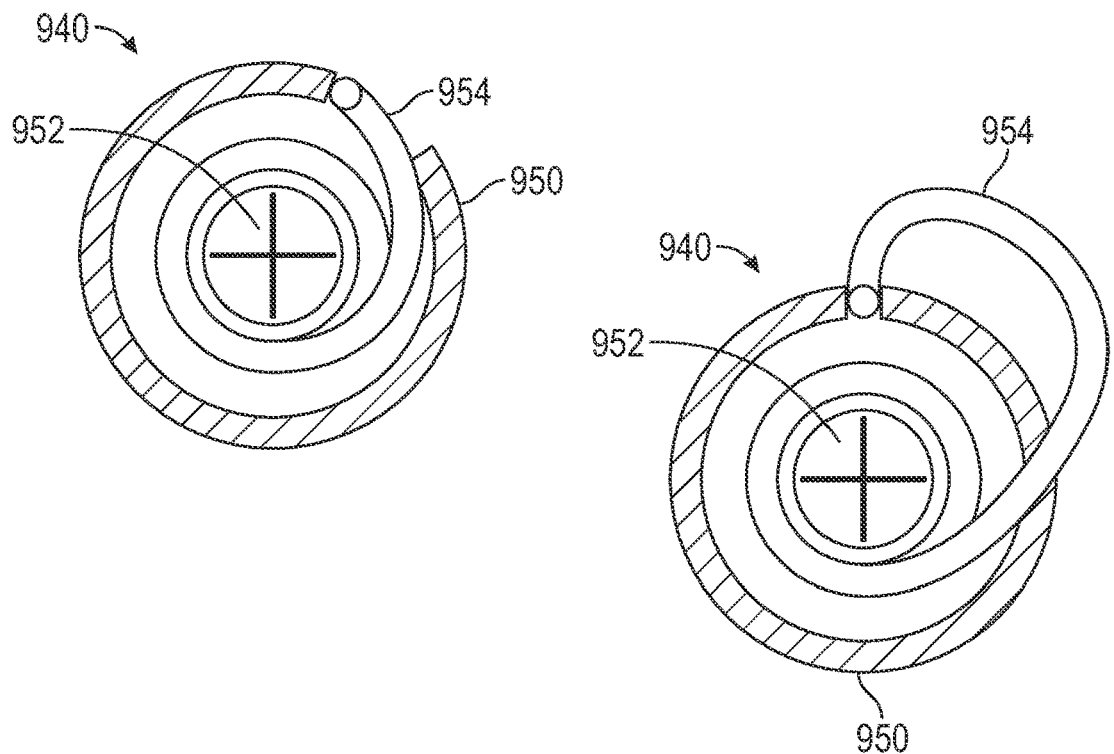
FIG. 43 is a pair of distal tip end views showing another exemplary embodiment of a decorticating system in both a closed state (upper inset) and an open state (lower inset.)

Referring to FIG. 43, another exemplary embodiment of a decorticating system and method is shown. FIG. 43 shows a distal tip end view of instrument 940, both in a closed position (upper inset figure) and an open position (lower inset figure.) Instrument 940 has a tubular body 950, a drive shaft 952 located within the body 950, and a decorticating wire 954 having ends attached to both the drive shaft 952 and tubular body 950. When drive shaft 952 is turned in one direction relative to the body (clockwise in FIG. 43), wire 954 is wound around drive shaft 952 and retracted within body 950, as shown in the upper inset. When drive shaft 952 is turned in the opposite direction, wire 954 at least partially unwinds from drive shaft 952 and extends radially outward through an opening in body 950, as shown in the lower inset.

In operation, the distal tip of instrument 940 may be advanced into the bone joint of a patient when the instrument is in the closed position. The instrument may then be moved into its open position as described above to extend the cutting wire 954, and the entire instrument may then be rotated about its longitudinal axis to decorticate the bone joint with wire 954. The wire 954 may then be retracted again to remove the instrument from the patient.

In some embodiments, wire 954 of instrument 940 may be coated with an abrasive. Wire 954 may include attached cutters, barbs, sharp edges, a square cross-section, twisted filaments, lines/slots cut therein, etc. (not shown.)

Figure 44:
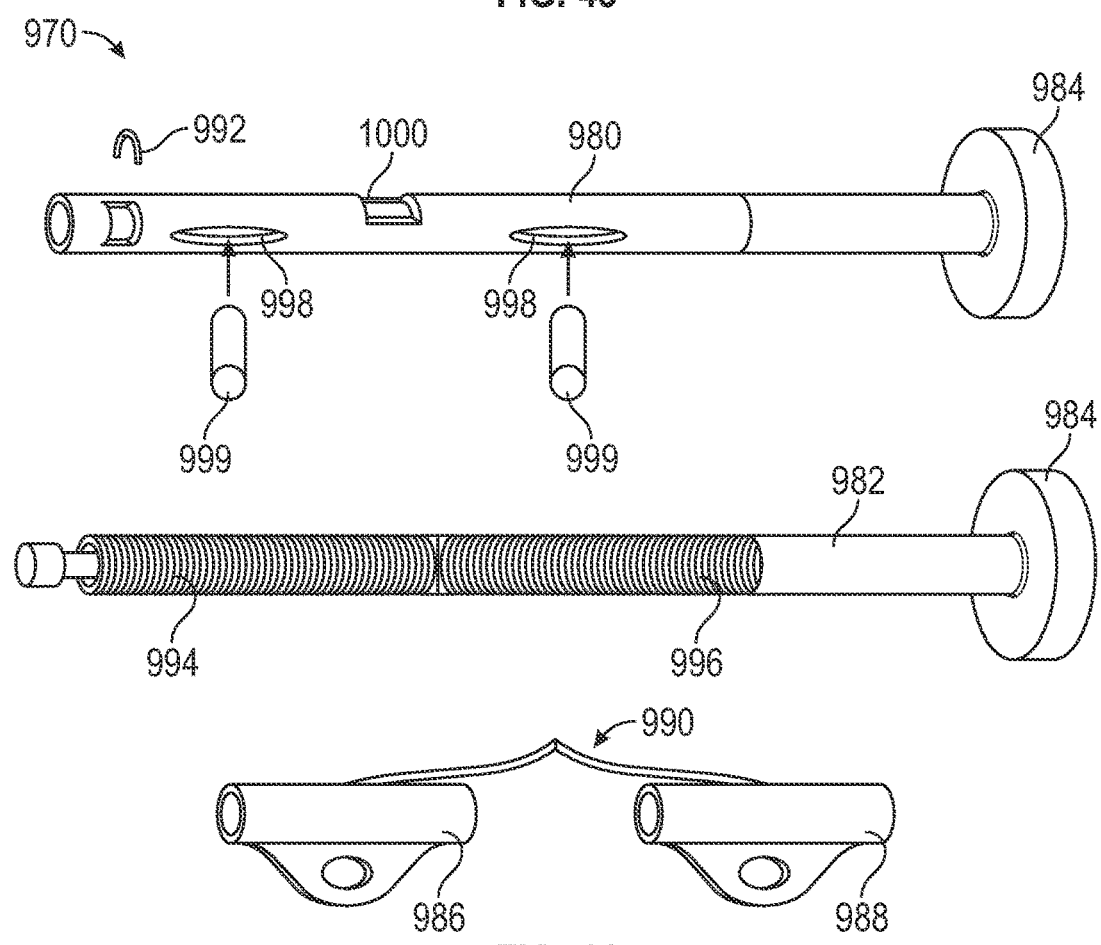
FIG. 44 is an exploded view showing the components of another exemplary embodiment of a decorticating system

Referring to FIG. 44, another exemplary embodiment of a decorticating system and method is shown. FIG. 44 is an exploded view showing components of system 970. System 970 includes an outer tube 980, an inner drive shaft 982, a handle 984 attached to the proximal end of drive shaft 982, a right-hand threaded tube 986, a left-hand threaded tube 988, and a cutting band 990 spanning between tubes 986 and 988 as shown. Inner drive shaft 982 is received within a central bore of outer tube 980 and retained there by a retainer clip 992. The distal end of drive shaft 982 is provided with a right-hand threaded section 994 and a left-hand threaded section 996 for receiving right-hand threaded tube 986 and left-hand threaded tube 988, respectively. Slots 998 are provided in outer tube 980 to receive radially extending tabs on threaded tubes 986 and 988, to prevent tubes 986 and 988 from rotating but allowing them to translate axially with respect to outer tube 980 and inner drive shaft 982. Alternatively, pins 999 may pass through slots 998 and be connected to tubes 986 and 988, as depicted in FIG. 44.

In operation, inner drive shaft 982 may be rotated with respect to outer tube 980 by using handle 984. With the previously described arrangement of right and left-hand threaded tubes on drive shaft 982, turning drive shaft 982 in one direction causes threaded tubes 986 and 988 to move closer together, and turning drive shaft 982 in the opposite direction causes threaded tubes 986 and 988 to move farther apart. When threaded tubes 986 and 988 move closer together, a middle portion of band 990 extends radially outward from inner drive shaft 982 and through a window 1000 in outer tube 980. The farther handle 984 is rotated, the farther band 990 extends outwardly through window. However, in some embodiments, regardless of the distance that band 990 extends through window 1000, the distance between its two extending portions (in the axial direction of the instrument) remains essentially the same, controlled by the axial width of window 1000.

With band 990 retracted within outer tube 980, the distal end of instrument 970 may be inserted into a bone joint in a manner similar to previously described embodiments. Band 990 may then be extended through window 1000 in outer tube 980 and the instrument rotated to decorticate the bone joint. In some embodiments, the center tip of band 990 is extended about 10 to 15 mm outside of window 1000. In some embodiments, band 990 is extended to a first radius to decorticate a first inner region of the joint, and then further extended to at least a second radius to decorticate a second outer region of the joint. After the joint has been sufficiently decorticated, band 990 may be retracted into outer tube 980 by turning handle 984 in an opposite direction and instrument 970 may be withdrawn from the patient.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present disclosure.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the disclosure as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the disclosure as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for decorticating at least one bone surface, the system comprising:
    an elongated soft tissue protector having a bore extending therethrough, the bore having a non-circular lateral cross-section, a maximum lateral extent and a minimum lateral extent;
    an elongated drive shaft having a proximal and a distal end; and
    a cutter located on or near the distal end of the drive shaft, the cutter having a non-circular lateral cross-section, a maximum lateral extent and a minimum lateral extent, the maximum lateral extent of the cutter being greater than the minimum lateral extent of the bore but no greater than the maximum lateral extent of the bore,
    wherein the bore of the soft tissue protector is configured to slidably receive the cutter therethrough, wherein the minimum lateral extent of the bore prevents the maximum lateral extent of the cutter from rotating when inside the bore but allows the drive shaft to rotate when the cutter is extended from a distal end of the bore.

2. The system of claim 1, wherein the bore of the soft tissue protector has a rectilinear lateral cross-sectional profile.

3. The system of claim 2, wherein the rectilinear lateral cross-sectional profile is generally triangular in shape.

4. The system of claim 1, wherein the system further comprises a body that is provided with a cylindrical bore therethrough, wherein the cylindrical bore is configured to slidably and rotatably receive the drive shaft, and wherein the body is configured to be slidably received within the bore of soft tissue protector.

5. The system of claim 1, wherein the drive shaft and cutter are provided with a longitudinal bore sized to slide over a guide pin.

6. The system of claim 1, wherein the proximal end of the drive shaft is provided with a handle configured to allow the drive shaft to be manually rotated and moved longitudinally relative to the soft tissue protector.

7. The system of claim 1, wherein the proximal end of the drive shaft is provided with an indexing feature configured to show a rotational orientation of the drive shaft and the cutter relative to the soft tissue protector so that the cutter can be aligned with and retracted into the soft tissue protector.

8. The system of claim 1, further comprising a navigation array mounted near the proximal end of the drive shaft, the array including a plurality of emitters or reflectors located at predetermined and unique distances from one another to generate a signal to aid in navigation of the cutter with regard to a reference frame associated with a patient on an imaging system.

9. A system for decorticating at least one bone surface, the system comprising:
- an elongated drive shaft;
- an elongated body having a central longitudinal axis, the body having a bore extending therethrough, wherein the bore is parallel to and laterally offset from the central longitudinal axis, wherein the bore is configured to slidably and rotatably receive the drive shaft therethrough; and
- a non-symmetrical offset cutter located on or near a distal end of the drive shaft, the cutter having a profile that fits within a lateral cross-section of the elongated body in at least one orientation and extends laterally outside of the cross-section when the drive shaft and cutter are rotated.

10. The system of claim 9, wherein the lateral cross-section of the elongated body has a rectilinear profile.

11. The system of claim 10, wherein the rectilinear profile is generally triangular in shape.

12. The system of claim 9, further comprising a navigation array mounted near a proximal end of the drive shaft, the array including a plurality of emitters or reflectors located at predetermined and unique distances from one another to generate a signal to aid in navigation of the cutter with regard to a reference frame associated with a patient on an imaging system.

13. A method of decorticating at least one bone surface, the method comprising:
- forming an implant bore across a first bone into a space between the first bone and an adjacent second bone, the implant bore having a non-circular lateral cross-section, a maximum lateral extent and a minimum lateral extent;
- inserting a cutter of a decorticating device through the non-circular implant bore and into the space between the first and second bones, the cutter having a non-circular lateral cross-section, a maximum lateral extent and a minimum lateral extent, the maximum lateral extent of the cutter being greater than the minimum lateral extent of the implant bore but no greater than the maximum lateral extent of the implant bore; and
- rotating the cutter of the decorticating device such that the maximum lateral extent of the cutter extends laterally beyond the implant bore and decorticates a surface of at least one of the first and second bones.

* * * * *